United States Patent
Knerr et al.

(10) Patent No.: US 11,840,560 B2
(45) Date of Patent: Dec. 12, 2023

(54) PRODRUGS AND USES THEREOF

(71) Applicant: Novo Nordisk A/S, Bagsvaerd (DK)

(72) Inventors: Patrick James Knerr, Plainfield, IN (US); Brian Patrick Finan, Indianapolis, IN (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 18/099,282

(22) Filed: Jan. 20, 2023

(65) Prior Publication Data

US 2023/0227521 A1    Jul. 20, 2023

Related U.S. Application Data

(60) Provisional application No. 63/301,311, filed on Jan. 20, 2022.

(30) Foreign Application Priority Data

Jan. 31, 2022  (EP) .................................... 22154309

(51) Int. Cl.
C07K 14/605    (2006.01)

(52) U.S. Cl.
CPC ................................. C07K 14/605 (2013.01)

(58) Field of Classification Search
CPC .................................................. C07K 14/605
See application file for complete search history.

(56) References Cited

U.S. PATENT DOCUMENTS

| | | |
|---|---|---|
| 8,507,428 B2 | 8/2013 | Dimarchi et al. |
| 9,745,360 B2 | 8/2017 | Haack et al. |
| 9,758,561 B2 | 9/2017 | Bossart et al. |
| 9,868,772 B2 | 1/2018 | Dimarchi et al. |
| 10,604,555 B2 | 3/2020 | Hogendorf et al. |
| 2014/0162945 A1 | 6/2014 | Ma et al. |
| 2014/0357552 A1 | 12/2014 | Asami et al. |
| 2015/0031606 A1 | 1/2015 | Vilhelmsen |
| 2016/0015788 A1 | 1/2016 | Holscher |
| 2016/0280754 A1 | 9/2016 | Shelton et al. |
| 2017/0112897 A1 | 4/2017 | Talbot et al. |
| 2019/0202883 A1 | 7/2019 | Asami et al. |
| 2020/0023040 A1 | 1/2020 | Benson et al. |
| 2020/0079832 A1 | 3/2020 | Holscher |
| 2022/0125940 A1 | 4/2022 | Knerr et al. |
| 2022/0168396 A1 | 6/2022 | Wu et al. |
| 2022/0177538 A1 | 6/2022 | Knerr et al. |
| 2022/0251163 A1 | 8/2022 | Zhao et al. |
| 2023/0120597 A1 | 4/2023 | Knerr et al. |
| 2023/0272029 A1 | 8/2023 | Knerr et al. |

FOREIGN PATENT DOCUMENTS

| | | | |
|---|---|---|---|
| CN | 110642935 | | 1/2020 |
| CN | 110684082 | | 1/2020 |
| EP | 0442724 | * | 8/1991 |
| WO | 2010011439 A2 | | 1/2010 |
| WO | 2010071807 A1 | | 6/2010 |
| WO | 10080605 A1 | | 7/2010 |
| WO | 2010148089 A1 | | 12/2010 |
| WO | 2011080103 A1 | | 7/2011 |
| WO | 11162968 A1 | | 12/2011 |
| WO | 11163012 A2 | | 12/2011 |
| WO | 2012080471 A1 | | 6/2012 |
| WO | 2012088379 A2 | | 6/2012 |
| WO | 2013164483 A1 | | 11/2013 |
| WO | 2013189988 A1 | | 12/2013 |
| WO | 2014152460 A2 | | 9/2014 |
| WO | 2014177683 A1 | | 11/2014 |
| WO | 2014192284 A1 | | 12/2014 |
| WO | 2015022420 A1 | | 2/2015 |
| WO | 2015035419 | | 3/2015 |
| WO | 2015067715 A2 | | 5/2015 |
| WO | 2015086728 | | 6/2015 |
| WO | 2015086729 A1 | | 6/2015 |
| WO | 2016049174 A1 | | 3/2016 |
| WO | 2016077220 | | 5/2016 |
| WO | 2016084826 | | 6/2016 |
| WO | 2016111971 | | 7/2016 |
| WO | 2016131893 | | 8/2016 |
| WO | 2018181864 | | 10/2018 |
| WO | 2019149880 A1 | | 8/2019 |
| WO | 2020023386 | | 1/2020 |
| WO | 2020023388 | | 1/2020 |
| WO | 2020207477 A1 | | 10/2020 |
| WO | 2022018186 A1 | | 1/2022 |

OTHER PUBLICATIONS

Bowie et al., 1990, Science 247: 1306-1310.*
Wells, 1990, Biochemistry 29:8509-8517.*
Bastin et al. "Dual GIP-GLP1-Receptor Agonists in the Treatment of Type 2 Diabetes: A Short Review on Emerging Data and Therapeutic Potential." Diabetes, metabolic syndrome and obesity: targets and therapy, Sep. 2019, vol. 12, pp. 1973-1985.
Buckley, Stephen T. et al., "Transcellular stomach absorption of a derivatized glucagon-like peptide-1 receptor agonist" Science Translational Medicine, Nov. 14, 2018, vol. 10, No. 467, eaar7047 pp. 1-13.
Feng et al., Two novel dual GLP-1/GIP receptor agonists are neuroprotective in the MPTP mouse model of Parkinson's disease. Neuropharmacology, Feb. 2018, vol. 133, pp. 385-394.
Finan et al., "Unimolecular Dual Incretins Maximize Metabolic Benefits in Rodents, Monkeys, and Humans." Sci Transl Med, Oct. 2013, vol. 5, No. 209, p. 209ra151.

(Continued)

*Primary Examiner* — Gyan Chandra
(74) *Attorney, Agent, or Firm* — Leon Y. Lum

(57) ABSTRACT

Prodrug compounds of GLP-1/GIP receptor co-agonists are provided wherein the GLP-1/GIP receptor co-agonists have been modified by the linkage of a dipeptide to the GLP-1/GIP receptor co-agonist through an amide bond. The prodrugs disclosed herein have extended half-lives and are converted to the active GLP-1/GIP receptor co-agonist at physiological conditions through a non-enzymatic reaction driven by chemical instability.

1 Claim, No Drawings

Specification includes a Sequence Listing.

(56) References Cited

OTHER PUBLICATIONS

Finan et al., "Reappraisal of GIP Pharmacology for Metabolic Diseases," Feature Review. Trends in Molecular Medicine, May 2016, vol. 22, No. 5, pp. 359-376.
Frias et al., "Efficacy and safety of LY3298176, a novel dual GIP and GLP-1 receptor agonist, in patients with type 2 diabetes: a randomised, placebo-controlled and active comparator-controlled phase 2 trial." Lancet, Nov. 2018, vol. 392, No. 10160, pp. 2180-2193.
Frias et al., "The Sustained Effects of a Dual GIP/GLP-1 Receptor Agonist, NNC0090-2746, in Patients with Type 2 Diabetes." Cell Metab. Aug. 2017, vol. 26, No. 2, pp. 343-352.e2.
Hedrington et al., "Oral semaglutide for the treatment of type 2 diabetes" Expert Opin Pharmacother, Nov. 2018, vol. 20, No. 2, pp. 133-141.
Killion et al. "Glucose-dependent insulinotropic polypeptide receptor therapies for the treatment of obesity, do agonists=antagonists?." Endocrine reviews, Feb. 2020, vol. 41, No. 1, pp. 1-21.
Knerr et al. "Selection and progression of unimolecular agonists at the GIP, GLP-1, and glucagon receptors as drug candidates." Peptides, Mar. 2020, vol. 125, No. 170225, p. 1-12.
Mroz et al., "Optimized GIP analogs promote body weight lowering in mice through GIPR agonism not antagonism," Feb. 2019, vol. 20, pp. 51-62.
Norregaard et al., "A novel GIP analogue, ZP4165, enhances glucagon-like peptide-1-induced body weight loss and improves glycaemic control in rodents." Diabetes Obes Metab., Jan. 2018, vol. 20, No. 1, pp. 60-68.
Schmitt et al. "Pharmacodynamics, pharmacokinetics and safety of multiple ascending doses of the novel dual glucose?dependent insulinotropic polypeptide/glucagon?like peptide?1 agonist RG 7697 in people with type 2 diabetes mellitus." Diabetes, Obesity and Metabolism, Jul. 2017, vol. 19, No. 10 , pp. 1436-1445.
Arnab et al., ""Synthesis and Characterization of Ester-Based Prodrugs of Glucagon-Like Peptide 1"", Peptide Science, Jun. 2010, vol. 94, No. 4, Special Issue SI, pp. 448-456.
Baggio et al., "Glucagon-like peptide-1 receptor co-agonists for treating metabolic disease", Molecular Metabolism, Sep. 2020, vol. 46, pp. 1-14.
Coskun et al., "LY3298176, a novel dual GIP and GLP-1 receptor agonist for the treatment of type 2 diabetes mellitus: From discovery to clinical proof of concept," Molecular Metabolism, Oct. 2018, vol. 18, pp. 3-14.
Frias et al., "Tirzepatide versus Semaglutide Once Weekly in Patients with Type 2 Diabetes", The New England Journal of Medicine, Aug. 5, 2021, vol. 385, pp. 503-515.
Gault et al., "Administration of an acylated GLP-1 and GIP preparation provides added beneficial glucose-lowering and insulinotropic actions over single incretins in mice with Type 2 diabetes and obesity", Clinical Science, Apr. 2011, vol. 121, No. 3, pp. 107-117.
Hornigold et al., "A GLP-1:CCK fusion peptide harnesses the synergistic effects on metabolism of CCK-1 and GLP-1 receptor agonism in mice", Appetite, May 2018, vol. 127, pp. 334-340.
Afferty et al., "Proglucagon-Derived Peptides as Therapeutics", Frontiers in Endocrinology, May 18, 2021, vol. 12, pp. 1-29.
Nauck et al., "Additive insulinotropic effects of exogenous synthetic human gastric inhibitory polypeptide and glucagon-like peptide-1-(7-36) amide infused at near-physiological insulinotropic hormone and glucose concentrations", J Clin Endocrinol Metab, Apr. 1993, vol. 76, No. 4, pp. 912-917.
Nauck et al., "The evolving story of incretins (GIP and GLP-1) in metabolic and cardiovascular disease: A pathophysiological update", Diabetes, Obesity & Metabolism, Jul. 2021, vol. 23, No. S3, pp. 5-29.
PCT Application No. PCT/EP2021/068985, filed Jul. 8, 2021.
Rosenstock et al., "Efficacy and safety of a novel dual GIP and GLP-1 receptor agonist tirzepatide in patients with type 2 diabetes (SURPASS-1): a double-blind, randomised, phase 3 trial", Lancet, Jul. 2021, vol. 398, No. 10295, pp. 143-155.
Salama et al., "The Impact of ?G on the Oral Bioavailability of Low Bioavailable Therapeutic Agents", Journal of Pharmacology and Experimental Therapeutics, Feb. 2005, vol. 312, pp. 199-205.
Testa et al., "Introduction: Metabolic Hydrolysis and Prodrug Design", 2003, pp. 1-9.
Thomas et al., "Dual GIP and GLP-1 Receptor Agonist Tirzepatide Improves Beta-cell Function and Insulin Sensitivity in Type 2 Diabetes", JCEM, Feb. 2021, vol. 106, No. 2, pp. 388-396.
Yu et al., "The effect of food on the relative bioavailability of rapidly dissolving immediate-release solid oral products containing highly soluble drugs", Molecular Pharmaceutics, Aug. 2004, vol. 1, No. 5, pp. 357-362.
Gomes et al., "Cyclization-activated Prodrugs", Molecules, Nov. 2007, vol. 12, No. 11, pp. 2484-2506.

\* cited by examiner

PRODRUGS AND USES THEREOF

TECHNICAL FIELD

The invention relates to 2,5-diketopiperazine (DKP) based prodrugs of compounds that are co-agonists of the glucagon-like peptide 1 (GLP-1) receptor and the glucose-dependent insulinotropic polypeptide (GIP) receptor with a protracted profile of action, suitable for oral administration to humans as well as the therapeutic use thereof.

CROSS-REFERENCE TO RELATED APPLICATIONS

This application claims priority to European Patent Application 22154309.3, filed Jan. 31, 2022; this application claims priority under 35 U.S.C. § 119 to U.S. Provisional Application 63/301,311, filed Jan. 20, 2022; the contents of which are incorporated by reference in their entirety.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Dec. 20, 2022, is named 220001 US02.xml and is 27 kilobytes in size.

BACKGROUND

Many therapeutically active agents experience low bioavailability after oral administration due to poor absorption or susceptibility to first pass metabolism (e.g. Salama N. N., Fasano A., Thakar M., Eddington N. D., The impact of ΔG on the oral bioavailability of low bioavailable therapeutic agents, *J. Pharmacol. Exp. Ther.*, 2005, 312, 199-205).

Prodrugs are therapeutic agents that are almost inactive per se but are predictably transformed into active molecular entities (e.g. Testa B., Mayer J. M, Hydrolysis in Drug and Prodrug Metabolism, Wiley-VCH, 2003, page 4). Prodrug chemistry offers the opportunity to precisely control the onset and duration of drug action after clearance from the site of administration and equilibration in the plasma at a highly defined concentration. Most of the prodrugs in clinical use today require enzymatic catalysis in order to be converted into the active drug. A prodrug approach via enzymatic catalysis is often used for drugs that need to be liberated in the blood stream following gastro-intestinal absorption. A common prodrug approach is the use of ester derivatives of the drug which are readily converted into the active drug by esterase-catalysed hydrolysis (e.g. Yu L. X., Straughn A. B., Faustion P. J., Yang Y., Parekh A., Ciavarella A. B., Asafu-Adjaye E., Mehta M. U., Conner D. P., Lesko L. J., Hussain A. S. The effect of food on the relative bioavailability of rapidly dissolving immediate-release solid oral products containing highly soluble drugs. *Mol. Pharm.* 2004, 1, 357-362.) A drawback of predominantly enzymatic cleavage is interpatient variability. Enzyme levels may differ significantly between individuals, resulting in biological variation of prodrug activation by the enzymatic cleavage. The enzyme levels may also vary depending on the site of administration. For instance, it is known that in the case of subcutaneous injection, certain areas of the body yield more predicable therapeutic effects than others. To reduce this unpredictable effect, non-enzymatic cleavage or intramolecular catalysis is of particular interest (e.g. Testa B., Mayer J. M, Hydrolysis in Drug and Prodrug Metabolism, Wiley-VCH, 2003, page 5).

DKP-based prodrug technology is based on a chemical conversion where a moiety consisting of two alpha-amino acids cyclizes to form a six-membered ring and concurrently liberates the active drug. DKP-based prodrug technology has previously been described. For instance, WO2010/071807, WO2010080605, WO2011/163012, and WO 2011/162968 describe various peptide-based prodrugs linked via amide bonds to e.g. glucagon superfamily peptides or other known medicinal agents. WO2014152460 and WO2016049174 describe peptide-based prodrugs of glucagon superfamily peptides and insulin having extended half-lives.

It has been described that dual activation of the GLP-1 and GIP receptors, e.g. by combining the actions of GLP-1 and GIP in one preparation, leads to a therapeutic principle with significantly better reduction of blood glucose levels, increased insulin secretion and reduced body weight in mice with type 2 diabetes (T2D) and obesity compared to the marketed GLP-1 agonist liraglutide (e.g. V A Gault et al., Clin Sci (Lond), 121, 107-117, 2011). Native GLP-1 and GIP were proven in humans following co-infusion to interact in an additive manner with a significantly increased insulinotropic effect compared to GLP-1 alone (M A Nauck et al., J. Clin. Endocrinol. Metab., 76, 912-917, 1993).

GLP-1/GIP receptor co-agonists and their potential medical uses are described in several patent applications such as WO 2010/011439, WO 2013/164483, WO 2014/192284, WO 2015/067715, WO 2015/022420, WO 2015/086728, WO 2015/086729, WO 2016/111971, WO 2020/023386, U.S. Pat. No. 9,745,360, US 2014/162945, and US 2014/0357552. Patent applications disclosing oral delivery of GLP-1 derivatives are described in e.g. WO 2011/080103, WO 2012/080471, WO 2013/189988, and WO 2019/149880.

However, there is still a desire for compounds having agonist activity at the GIP and GLP-1 receptors that are suitable for oral administration. Compounds with extended duration of action at both the GIP and GLP-1 receptors are desirable to allow for less frequent dosing of such a compound. Accordingly, there is a need for longer-acting GLP-1/GIP receptor co-agonists to realise their full potential in the treatment of diseases such as T2D.

SUMMARY

Peptide-based drugs are highly effective medicines with relatively short duration of action and variable therapeutic index. Prodrug technology may be employed to optimise the properties of a drug in a manner that makes it suitable for a specific dosing regimen, e.g. for once weekly dosing. Prodrugs undergo conversion by an enzymatic or a non-enzymatic chemical process resulting in slow liberation of a biologically-active drug molecule (referred to herein as the active drug) in vivo.

The present disclosure is directed to GLP-1/GIP receptor co-agonist prodrugs with desirable properties, e.g. for once weekly oral dosing. The prodrugs described herein are designed to delay onset of action and extend the half-life of the active drug, i.e. the GLP-1/GIP receptor co-agonist. The delayed onset of action is advantageous in that it allows a systematic distribution of the prodrug prior to its activation. Accordingly, the administration of prodrugs may eliminate complications caused by peak activities upon administration and increases the therapeutic index of the active drug. The intact prodrug is not exerting the biological activity to a significant extent compared to the active drug. The biological activity is derived from the active drug once it is liberated upon conversion of the prodrug. The reduced biological activity of the prodrug as compared to the liberated active drug is an advantage since it allows for a relatively large amount of prodrug to be administered without concomitant side effects and the risk of overdosing.

The present invention relates to GLP-1/GIP receptor co-agonist prodrugs. Also, or alternatively, the present invention relates to GLP-1/GIP receptor co-agonist prodrugs having extended terminal half-life in vivo.

In a first aspect, the invention relates to a compound that is a prodrug of a GLP-1/GIP receptor co-agonist. In some embodiments, the compound comprises Formula I: B-Z, wherein Z is a GLP-1/GIP receptor co-agonist (active drug), B is a dipeptide ("dipeptide B"), and wherein the N-terminal amino group of the GLP-1/GIP receptor co-agonist is linked to B via a peptide bond. In some embodiments, the dipeptide B comprises a covalently linked moiety such as a substituent that is capable of forming non-covalent binding interactions with a mammalian plasma protein such a mammalian serum albumin. In some embodiments, the dipeptide B is capable of being cleaved from the active drug Z via an intramolecular reaction releasing the active drug (i.e. the GLP-1/GIP receptor co-agonist) and forming 2,5-diketopiperazine (DKP) as a by-product. In some embodiments, the intramolecular reaction occurs under physiological conditions. Also, or alternatively in some embodiments, the intramolecular reaction occurs in the absence of enzymatic activity.

In a second aspect the invention relates to pharmaceutical compositions comprising the compounds as described herein.

In a third aspect the invention relates to compounds as described herein or pharmaceutical compositions comprising the compounds as described herein for use as a medicament.

In one functional aspect the invention provides for a prodrug (e.g. compounds as described herein) that has a conversion half-life suitable for once-weekly dosing. Also, or alternatively, in another functional aspect the invention provides for a prodrug that has an observed terminal half-life suitable for once-weekly dosing. Also, or alternatively, in another functional aspect the invention provides for a prodrug that has a surprisingly high oral bioavailability.

A further aspect of the invention relates to medical use of the compound described herein. Also, or alternatively, the invention relates to use of the compound described herein for prevention and/or treatment of type 2 diabetes. Also, or alternatively, the invention relates to use of the compound described herein for prevention and/or treatment of obesity. Also, or alternatively, the invention relates to use of the compound described herein for prevention and/or treatment of liver diseases.

A further aspect of the invention relates to methods of treating a disease by administering the compounds as described herein to a patient in need thereof. In some embodiments, the disease is type 2 diabetes. In some embodiments, the disease is overweight. In some embodiments, the disease is obesity.

The invention may also solve further problems that will be apparent from the disclosure of the exemplary embodiments.

DESCRIPTION

In what follows, Greek letters may be represented by their symbol or the corresponding written name, e.g.: α=alpha; β=beta; ε=epsilon; γ=gamma; ω=omega; etc. Also, the Greek letter of μ may be represented by "u", e.g. in μl=ul, or in μM=uM. The symbol

in a chemical drawing designates a point of attachment to a neighboring moiety. In what follows, unless otherwise indicated in the specification, terms presented in singular form also include the plural situation, e.g. when referring to the "compound", it is to be understood that this embraces all individual variants falling within a broad definition of said compound. As used herein "a" means "one or more". The present invention relates to compounds that are prodrugs of GLP-1/GIP receptor co-agonists such as prodrugs of GLP-1/GIP receptor co-agonists with desirable properties, e.g. for once weekly oral dosing. The compounds convert in a controlled fashion under physiological conditions to the active GLP-1/GIP receptor co-agonists (active drug).

In a first aspect the invention relates to a compound that is a prodrug of GLP-1/GIP receptor co-agonist, said compound comprising Formula I: B-Z, wherein Z is a GLP-1/GIP receptor co-agonist (active drug) that is liberated from B upon conversion of the prodrug. In a second aspect the invention relates to pharmaceutical compositions comprising the compounds described herein. A further aspect of the invention relates to medical use of the compound described herein. Also, or alternatively, the invention relates to use of the compound described herein for prevention and/or treatment of type 2 diabetes. Also, or alternatively, the invention relates to use of the compound described herein for prevention and/or treatment of obesity. Also, or alternatively, the invention relates to use of the compound described herein for prevention and/or treatment of liver diseases.

General Definitions

The term "compound" relates to a prodrug of a GLP-1/GIP receptor co-agonist. The compounds of the invention may be referred to as "compound", and the term "compound" is also meant to cover pharmaceutically relevant forms hereof, i.e., a pharmaceutically acceptable salt, amide, or ester thereof.

The term "polypeptide" or "polypeptide sequence", as used herein refers to a series of two or more amino acids interconnected via amide bonds (e.g. peptide bond). The term polypeptide is used interchangeably with the term "peptide" and the term "protein."

The term "derivative" generally refers to a chemically modified polypeptide (e.g. a GLP-1/GIP receptor co-agonist) or dipeptide in which one or more substituents are covalently linked to the amino acid sequence of the polypeptide or the dipeptide, e.g. via a bond to the ε-amino group of a Lys. In some embodiments, the compound of the invention comprises a derivative (e.g. a derivative of a GLP-1/GIP receptor co-agonist and/or a derivative of a dipeptide), which has been modified so that one or more substituents with protracting properties are covalently linked to the amino acid sequence of the polypeptide or the dipeptide.

The term "dipeptide derivative" means that the dipeptide is chemically modified so that it carries at least one substituent (e.g. substituent b, as described herein). In some embodiments, the may carry two or more substituents.

The term "GLP-1/GIP receptor co-agonist derivative" means a GLP-1/GIP receptor co-agonist is chemically modified so that it carries a substituent. For instance, such a GLP-1/GIP receptor co-agonist derivative may comprise one or more substituents that are covalently linked to the amino acid sequence of the polypeptide, e.g. via a bond to the ε-amino group of a Lys.

The term "amino acid conjugated to a fatty acid" refers to any proteinogenic or non-proteinogenic amino acid with a functional group that has been chemically modified to conjugate to a fatty acid by way of a covalent bond to the fatty acid or preferably, by way of a linker. Examples of such functional groups include amino (e.g. Lys), thiol (e.g. Cys), and carboxyl (e.g. Glu or Asp). In some embodiments the conjugated amino acid is Lys. When conjugating a fatty acid to said proteinogenic or non-proteinogenic amino acid with a functional group, a fatty acid precursor may be used such as a di-carboxylic acid (e.g. $CO_2H-(CH_2)-CO_2H$, wherein n=10-22).

The term "fatty acid" refers to an optionally substituted carboxylic acid with an aliphatic or a cyclic hydrocarbon chain, wherein the aliphatic chain is saturated or unsaturated. In some embodiments, the fatty acid is a $C_{12}$-$C_{24}$ saturated carboxylic acid such as a $C_{16}$-$C_{22}$ saturated carboxylic acid. In some embodiments, the fatty acid comprises additional functional groups.

The term "lipophilic moiety" as used herein refers to a moiety that comprises an aliphatic and/or a cyclic hydrocarbon moiety with a total of more than 6 and less than 30 carbon atoms, preferably more than 8 and less than 20 carbon atoms. In some embodiment, the lipophilic moiety comprises a carbon chain which contains at least 8 consecutive —$CH_2$— groups. In some embodiment, the lipophilic moiety comprises at least 10 consecutive —$CH_2$— groups, such as least 12 consecutive —$CH_2$— groups, at least 14 consecutive —$CH_2$— groups, at least 16 consecutive —$CH_2$— groups, or at least 18 consecutive —$CH_2$— groups. In some embodiments, the lipophilic moiety can comprise any number between 6 and 30 consecutive —$CH_2$— groups (e.g. 6, 7, 8, 9 etc.)

The term "distal carboxylic acid" as used herein in context of the lipophilic moiety, refers to a carboxylic acid attached to the most remote (terminal) point of the lipophilic moiety relative to the lipophilic moiety's point of attachment to adjacent moieties, e.g. in the compounds as described herein, the lipophilic moiety with distal carboxylic acid (e.g. Chem. 1) is a protracting moiety, and the carboxylic acid is attached to the most remote (terminal) point of the lipophilic moiety relative to the lipophilic moiety's point of attachment to the adjacent linker elements (e.g. Chem. 2, Chem. 3, Chem. 4, or Chem. 5). A non-limiting example of a lipophilic moiety with distal carboxylic acid is Chem. 1.

The term "therapeutic index" describes a ratio that compares the blood concentration at which a drug becomes toxic and the concentration at which the drug is effective. The larger the therapeutic index (TI), the safer the drug is. If the TI is small (the difference between the two concentrations is very small), the drug must be dosed carefully and the person receiving the drug should be monitored closely for any signs of drug toxicity.

Amino Acids

The term "amino acid" as used herein refers to any amino acid, i.e. both proteinogenic amino acids and non-proteinogenic amino acids. The term "proteinogenic amino acids" as used herein refers to the 20 standard amino acids encoded by the genetic code in humans. The term "non-proteinogenic amino acids" as used herein refers to any amino acid which does not qualify as a proteinogenic amino acid. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid, or 2-aminoisobutyric acid), norleucine, norvaline as well as the D-isomers of the proteinogenic amino acids.

In general, amino acid residues, e.g. in context of a polypeptide sequence, as used herein may be identified by their full name, their one-letter code, and/or their three-letter code. These three ways are fully equivalent and used interchangeably. In what follows, each amino acid of the peptides as described herein for which the optical isomer is not stated is to be understood to mean the L-isomer (unless otherwise specified). Examples of non-proteinogenic amino acids that may be incorporated into the compounds of the invention are listed in Table 1.

TABLE 1

Non-limiting examples of non-proteinogenic amino acids that may be incorporated into the compounds of the invention.

| Amino acid name | Amino acid short name | Structure |
|---|---|---|
| N-Methylglycine, sarcosine | Sar | 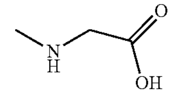 |
| N-Ethylglycine | N-Et-Gly | 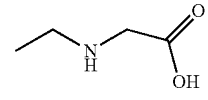 |
| N-Propylglycine | N-Pr-Gly | 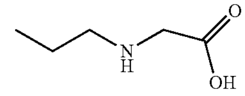 |

TABLE 1-continued

Non-limiting examples of non-proteinogenic amino acids that may
be incorporated into the compounds of the invention.

| Amino acid name | Amino acid short name | Structure |
| --- | --- | --- |
| N-sec-Butylglycine | N-sBu-Gly | 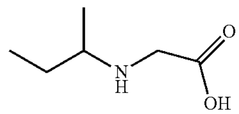 |
| Trans-4-hydroxy-L-proline | Pro(4-OH) | 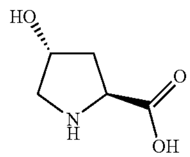 |
| N-methyl-L-norleucine | N-Me-Nle | 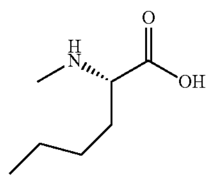 |
| N-Methyl-L-homoalanine | N-Me-homoAla | 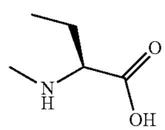 |
| N-Methyl-L-alanine | N-Me-Ala | 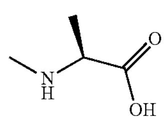 |
| N-Propyl-L-alanine | N-Pr-Ala | 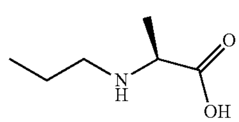 |
| N-Methyl-L-leucine | N-Me-Leu | 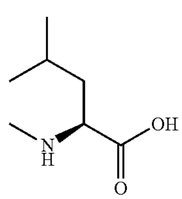 |
| N-Methyl-L-valine | N-Me-Val | 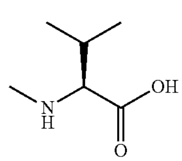 |
| N-Methyl-D-valine | N-Me-D-Val | 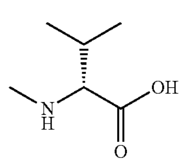 |

TABLE 1-continued

Non-limiting examples of non-proteinogenic amino acids that may be incorporated into the compounds of the invention.

| Amino acid name | Amino acid short name | Structure |
| --- | --- | --- |
| N-Methyl-L-lysine | N-Me-Lys | 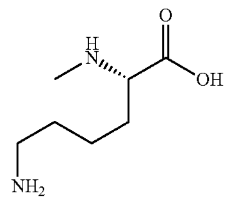 |
| N-Methyl-L-histidine | N-Me-His | 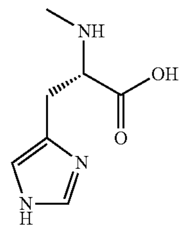 |
| N-(2-aminoethyl)Glycine | Aeg | 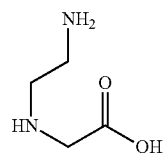 |
| N-hexyl-L-homoAlanine | N-Hex-homoAla | 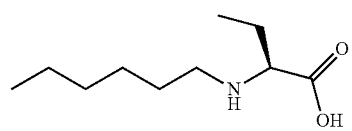 |
| L-Homoproline | homoPro | 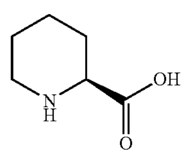 |
| D-Homoproline | D-homoPro | 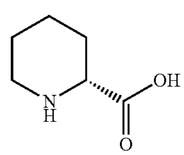 |
| (S)-Azetidine-2-carboxylic acid | Aze | 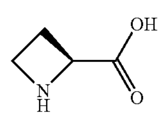 |
| N-Methyl-L-glutamic acid | N-Me-Glu | 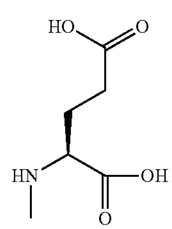 |

TABLE 1-continued

Non-limiting examples of non-proteinogenic amino acids that may
be incorporated into the compounds of the invention.

| Amino acid name | Amino acid short name | Structure |
| --- | --- | --- |
| N-Methyl-L-phenylalanine | N-Me-Phe | 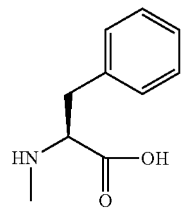 |
| 4-Amino-L-phenylalanine | Phe(4-NH$_2$) | 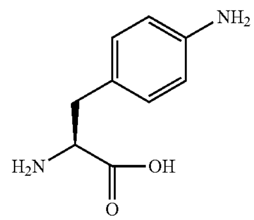 [SMILES: Nc1ccc(C[C@H](N)C(=O)O)cc1] |
| 2-Naphthyl-D-alanine | D-2-Nal | 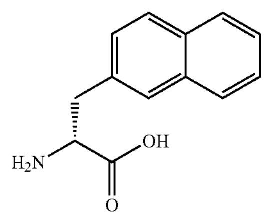 [SMILES: N[C@H](Cc1ccc2ccccc2c1)C(=O)O] |

Prodrug

The term "prodrug" as used herein refers to a compound that undergoes chemical conversion by an enzymatic or a non-enzymatic chemical process in vivo resulting in liberation of an active drug. The term "active drug" as used herein refers to a pharmacologically active compound which is liberated from a prodrug upon conversion of the prodrug. Non-limiting examples of active drugs are parent compounds 1-5 as described herein. The term "conversion" as used herein in context of a prodrug refers to a process wherein the prodrug is converted in an enzymatic or a non-enzymatic manner resulting in the liberation of an active drug. The rate with which the conversion takes place may be quantified by the "conversion half-life". The "conversion half-life" is the length of time required for the concentration of the prodrug to be reduced to half as a consequence of conversion. The "conversion half-life" may also be referred to as the "prodrug to drug conversion half-life" or as the "prodrug to active drug conversion half-life".

A prodrug is not exerting the intended pharmacological activity to a significant extent, e.g. it is not exerting the intended pharmacological activity to an extent that makes it incompatible with the treatment regime it is intended for. The pharmacological activity associated with the intended treatment of the prodrug is derived from the active drug once it is liberated. When the active drug is liberated from the prodrug it is said to be in its "free form". The prodrug may achieve the desired conversion upon intramolecular cyclization of a terminal dipeptide-based amide extension, whereupon the extension is cleaved from the active drug, resulting in the liberation of the active drug in its free form. Such an intramolecular cyclization may take place as an enzyme-independent processes under physiological conditions, e.g. via 2,5-diketopiperazine (DKP) formation. In a prodrug which is converted into an active drug via said intramolecular cyclization forming DKP, the moiety from which the active drug is liberated upon conversion is referred to as the "DKP moiety". The "DKP moiety" comprises a dipeptide moiety (e.g. a dipeptide or a dipeptide derivative). In some embodiments, the prodrug may have a temporary amide linkage such as a peptide bond between a dipeptide moiety of the DKP moiety, and an aliphatic amine group of the active drug. In some embodiment, the DKP moiety is attached to the GLP-1/GIP receptor co-agonist via an alpha-amino group of the amino acid in position 1 of the GLP-1/GIP receptor co-agonist backbone, i.e. an amide bond formed between the carboxylic acid group of the DKP moiety and the alpha-amino group of Tyr in position 1 of the GLP-1/GIP receptor co-agonist backbone. In some embodiment, the DKP moiety is attached to the amino group of Tyr1 in the GLP-1/GIP receptor co-agonist backbone via acylation, i.e. via an amide bond formed between a carboxylic acid group of the DKP moiety and the alpha-amino group of Tyr1 in the GLP-1/GIP receptor co-agonist backbone.

The conversion half-life may be influenced by the structural nature of the DKP moiety. For instance, a desirable conversion half-life may be obtained by using dipeptide B as exemplified in this application. The conversion half-life may be influenced by the structural nature of the amino acid of the active drug to which the DKP moiety is linked. In some embodiments, a desirable conversion half-life may be obtained by using the N-terminal amino acid residue of the active drug exemplified in this application. In some embodiments, the DKP moiety is a dipeptide-based extension attached to the active drug. In some embodiments, the DKP moiety comprises further structural elements, e.g. a substituent covalently linked to the dipeptide (also referred to as "dipeptide derivative" herein. Upon conversion of the prodrug and release of the active drug, DKP is formed as a by-product. DKP may be inactive or may be associated with pharmacological activity. In some embodiments, conversion of the prodrug as described herein takes place predominantly in a non-enzymatic manner. In some embodiments, conversion of the prodrugs as described herein takes place solely in a non-enzymatic manner.

In some embodiment, the compounds as described herein are prodrugs or pharmaceutical acceptable salts, esters or amides thereof. In some embodiments the prodrug is a compound according to Formula I, wherein B is a dipeptide optionally comprising a substituent b, wherein the substituent b comprises or consists of a protractor and optionally a linker. In some embodiments, Z is a GLP-1/GIP receptor co-agonist carrying a substituent z; and wherein the N-terminal amino group of the GLP-1/GIP receptor co-agonist is linked to B via a peptide bond. In some embodiments of the invention B is a DKP moiety.

In some embodiments the compounds as described herein comprise a DKP moiety. In some embodiments, the compound as described herein comprises a prodrug which comprises a DKP moiety and an active drug. In some embodiment, the active drug is a GLP-1/GIP receptor co-agonist (e.g. active drug Z). In some embodiment, the DKP moiety comprises a dipeptide (e.g. dipeptide B), optionally carrying one or more substituents.

An example of the nomenclature used for the compounds as described herein, also referred herein as "prodrugs", comprising a DKP moiety and a GLP-1/GIP receptor co-agonist as the active drug, is provided in the following: K[(4S)-4-carboxy-4-(15-carboxypentadecanoylamino)butanoyl]-Sar-Y-Aib-EGTFTSDYSILLEEQAAREFIEWL-LAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH. In this compound the DKP moiety comprises a Lys residue and a Sar residue interconnected via an amide bond. The moiety (4S)-4-carboxy-4-(15-carboxypentadecanoylamino)butanoyl is covalently linked to the ε-nitrogen atom of the Lys residue of the dipeptide via an amide bond, and the moiety 2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl is covalently linked to the ε-nitrogen atom of the Lys residue of the GLP-1/GIP receptor co-agonist via an amide bond. The carboxyl group of the Sar residue is covalently linked to the N-terminal amino group of the amino acid sequence of GLP-1/GIP receptor co-agonist via an amide bond. The full structure of the compound is depicted below:

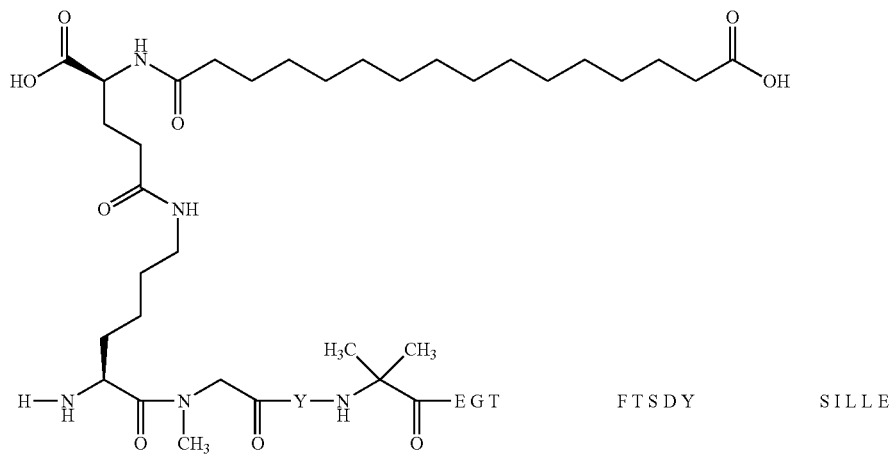

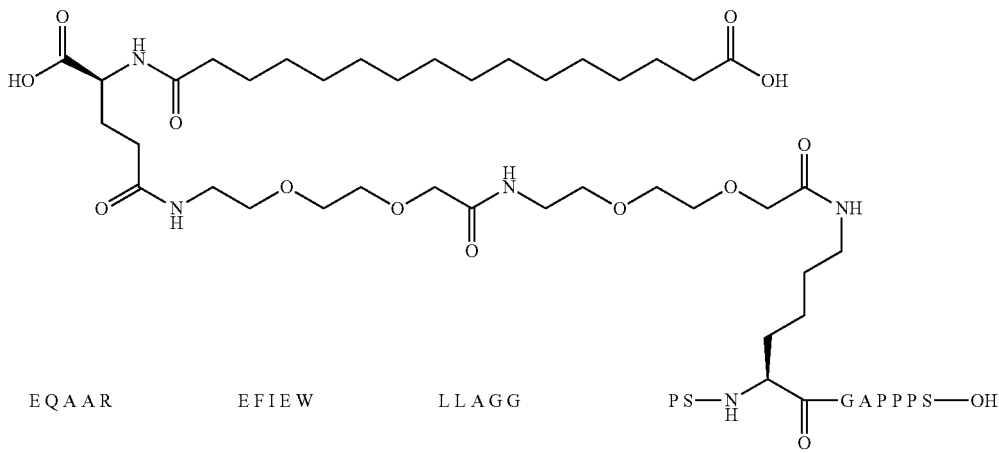

Substituent

The term "substituent", as used herein, refers to a moiety that is covalently attached to an amino acid of a dipeptide or a polypeptide (e.g. a GLP-1/GIP receptor co-agonist). In some embodiments, a substituent z is attached to a GLP-1/GIP receptor co-agonist via a Lys. In some embodiments, a substituent b is attached to an amino acid residue of the DKP moiety of a GLP-1/GIP receptor co-agonist such as the dipeptide moiety (e.g. dipeptide B) that is present in the compounds of the invention, thus forming part of a DKP moiety. If a substituent is attached to a polypeptide or a dipeptide, the polypeptide or the dipeptide is said to be "substituted". When a substituent is covalently attached to a polypeptide or to an amino acid residue, said polypeptide or amino acid is said to "carry" a substituent. The substituent may comprise a series of individually defined moieties; these moieties may be referred to as "substituent elements". Non-limiting examples of "substituent elements" are a "protractor" and a "linker".

The substituent may be capable of forming non-covalent binding interactions with albumin, thereby promoting the circulation of the compound in the blood stream, and thus having the effect of protracting the time of which the compound is present in the blood stream, since the aggregate of the substituent-carrying compound and albumin is only slowly disintegrated to release the free form of the compound; thus, the substituent, as a whole, may also be referred to as an "albumin-binding moiety", and the substituent may be said to have a "protracting effect". The substituent may comprise a portion which is particularly relevant for the albumin binding and thereby the protraction, which portion may be referred to as a "protractor" or a "protracting moiety". The term "protractor" and "protracting moiety" are used interchangeably herein. The "protractor" may be a lipophilic moiety (e.g. a fatty acid). The "protractor" may be a fatty acid (e.g. a $C_{16}$-$C_{22}$ carboxylic acid). A non-limiting example of a "protractor" is shown in Table 2. In the chemical formula Chem. 1,

is used to describe an attachment point to the linker or the polypeptide via a covalent bond.

TABLE 2

Non-limiting example of a "protractor".

| Reference | Structure |
|---|---|
| Chem. 1 | HO—C(=O)—(CH₂)ₙ—C(=O)— wherein n = 12, 14, 16, 18 or 20 |

The substituent may comprise a portion between the protracting moiety and the point of attachment to the amino acid residue of the polypeptide, which portion may be referred to as a "linker". The linker may comprise several "linker elements". The linker elements may be selected so that they improve the overall properties of the molecule, e.g. so that they improve the oral bioavailability, the conversion half-life or the protracting effect, thus improving the overall exposure profile upon oral administration of the compound.

Non-limiting examples of linker elements are listed in Table 3. In the chemical formulae Chem. 2-5,

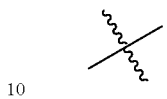

is used to describe an attachment point to the protractor or to the polypeptide.

TABLE 3

Non-limiting examples of linker elements

| Reference | Structure | Abbreviation |
|---|---|---|
| Chem. 2 | 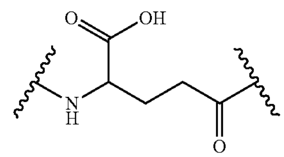 [SMILES: *NC(CCC(*)=O)C(=O)O] | γGlu |
| Chem. 3 | 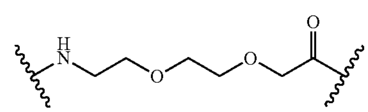 [SMILES: *NCCOCCOCC(*)=O] | Ado |
| Chem. 4 | 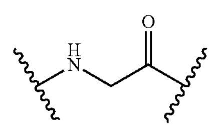 [SMILES: *NCC(*)=O] | Gly |
| Chem. 5 | 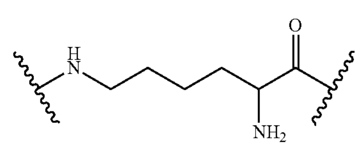 [SMILES: *NCCCCC(N)C(*)=O] | εLys; |

In some embodiments, the substituent is L-P (Formula III), wherein P comprises or consists of a lipophilic moiety with a distal carboxylic acid and P has protracting properties. In some embodiments, P is Chem. 1. In some embodiment, P is Chem. 1 and L is a linker comprising linker elements $A_1$-$A_5$:

$$L\text{-}P \quad \text{(Formula III)},$$

wherein P is Chem. 1, and wherein L is of Formula IV:

$$A_1\text{-}A_2\text{-}A_3\text{-}A_4\text{-}A_5 \quad \text{(Formula IV)},$$

wherein $A_1$ is covalently bound to an amino acid of the dipeptide or the GLP-1/GIP receptor co-agonist and is selected from a group consisting of Chem. 2, Chem. 3, Chem. 4, and Chem. 5; wherein $A_5$ is covalently bound to P and is Chem. 2; wherein each of $A_2$, $A_3$, and $A_4$, are individually selected from the group consisting of Chem. 2, Chem. 3, Chem. 4, and Chem. 5, or is absent, with the proviso that if $A_2$, $A_3$, $A_4$, and $A_5$ are absent then $A_1$ is also covalently bound to P.

Non-limiting examples of substituents comprising a lipophilic moiety are listed in Table 4. In some embodiments, the substituent is selected from Table 4.

TABLE 4
Non-limiting examples of substituents.
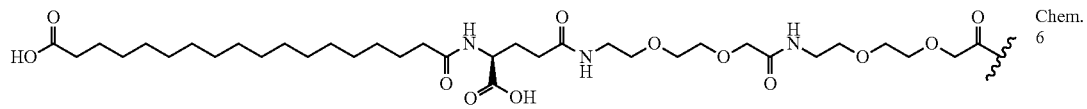
Chem. 6
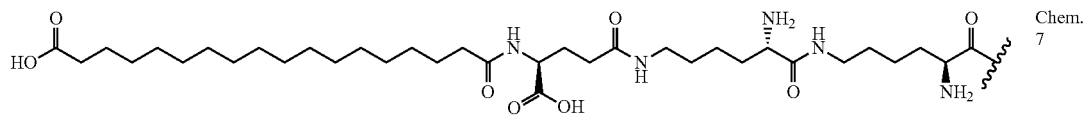
Chem. 7
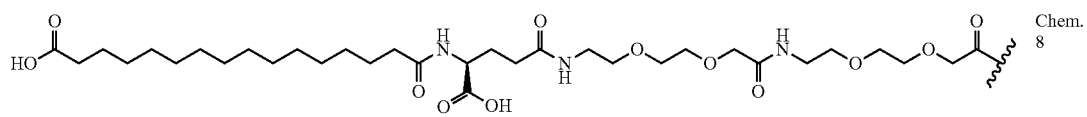
Chem. 8
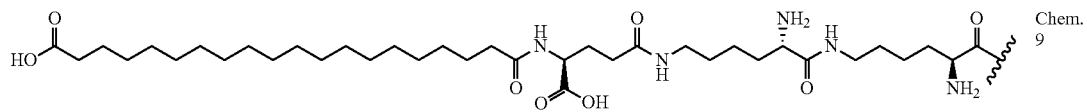
Chem. 9
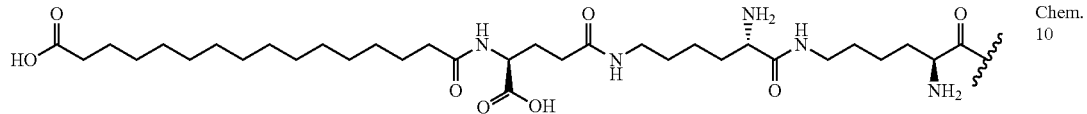
Chem. 10
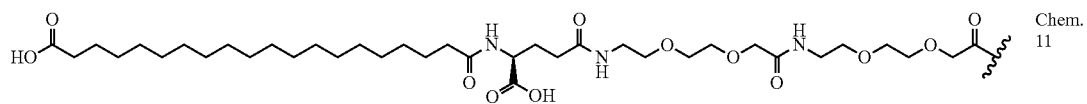
Chem. 11
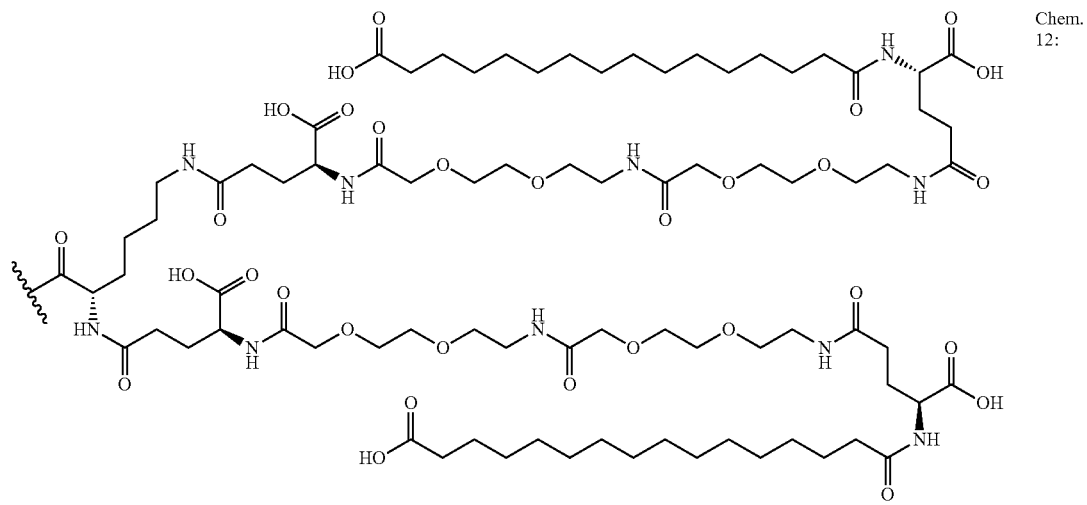
Chem. 12:

TABLE 4-continued
Non-limiting examples of substituents.
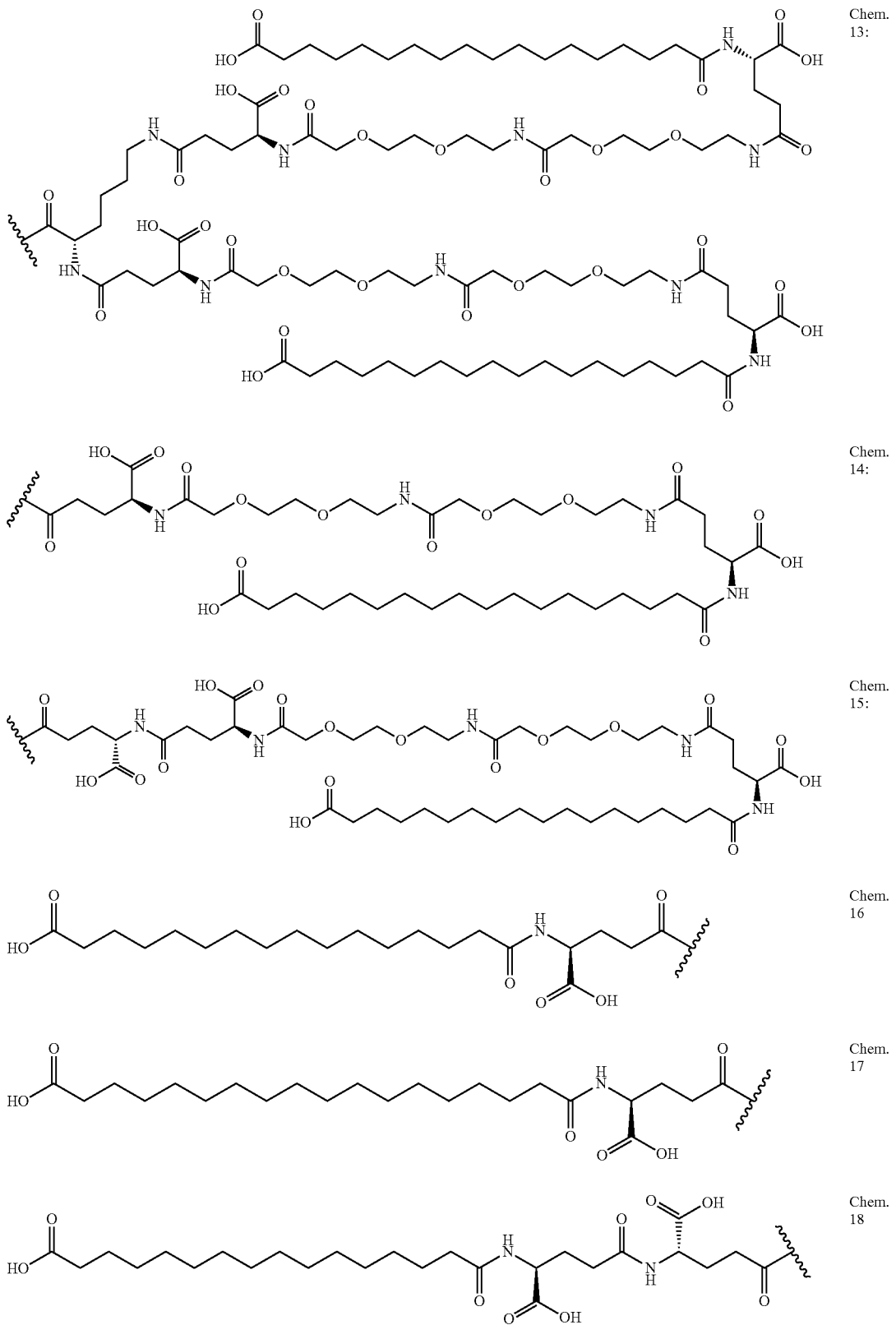

TABLE 4-continued

Non-limiting examples of substituents.

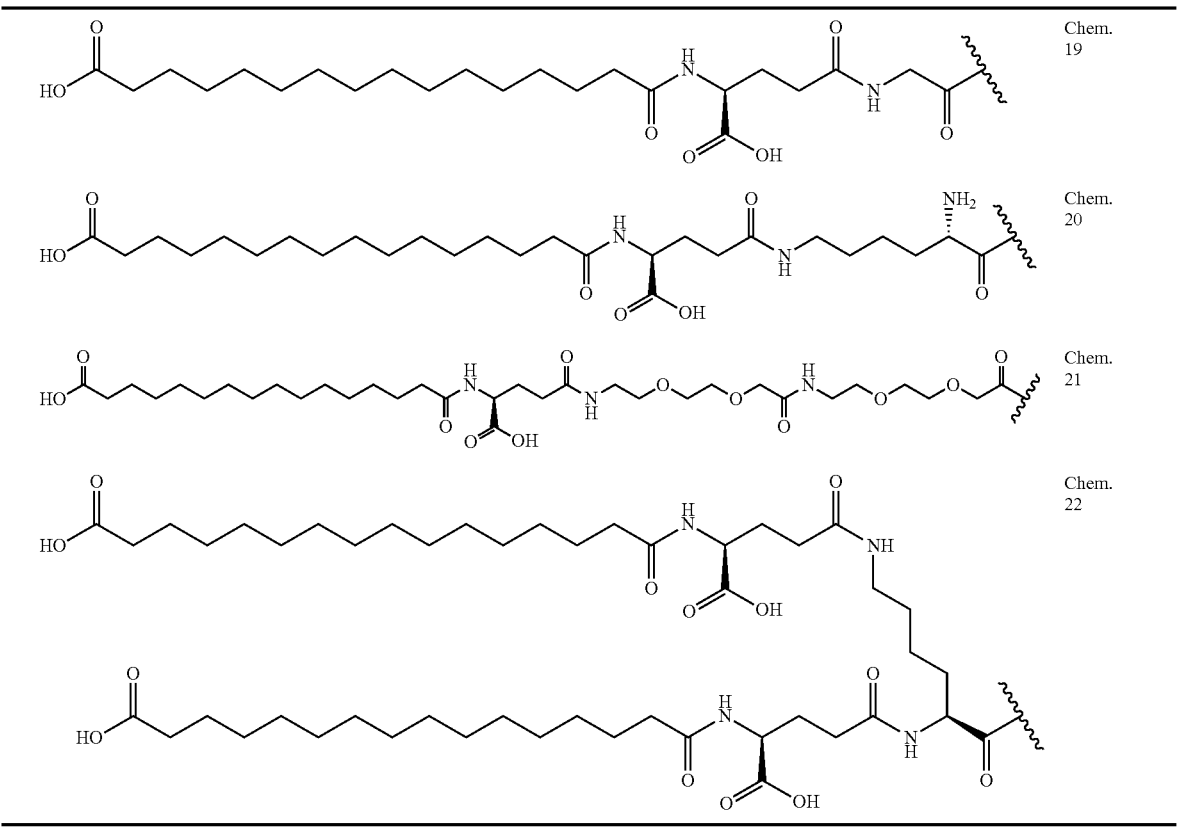

Chem. 19

Chem. 20

Chem. 21

Chem. 22

If the substituent is attached to the dipeptide moiety of the compounds as described herein (e.g. dipeptide B), then the substituent is referred herein as "substituent b". In some embodiments, substituent b comprises a protractor according to Chem. 1, wherein n is 14, 16 or 18; and optionally a linker, wherein the linker comprises one or more γGlu (Chem. 2), and/or one or more Ado (Chem. 3) and/or one or more Gly (Chem. 4) and/or one or more εLys (Chem. 5). In some embodiments, substituent b is selected from the group consisting of Chem. 16, Chem. 17, Chem. 18, Chem. 19, Chem. 20, Chem. 21, and Chem. 22.

If the substituent is attached to the GLP-1/GIP receptor co-agonist of the compounds as described herein (e.g. active drug Z), then the substituent is referred herein as "substituent z". In some embodiments, substituent z comprises or consists of a protractor according to Chem. 1, wherein n is 14, 16 or 18 and a linker, wherein the linker comprises or consists of one or more γGlu (Chem. 2) and/or one or more Ado (Chem. 3) and/or one or more εLys (Chem. 5). In some embodiments, substituent z is selected from the group consisting of Chem. 7, Chem. 8, Chem. 10, and Chem. 11.

In some embodiments the compound of the invention comprises a substituent b and/or a substituent z.

GLP-1/GIP Receptor Co-Agonist

As used herein, "GLP-1/GIP receptor co-agonists" are compounds that are GLP-1 receptor agonists and GIP receptor agonists. The GLP-1/GIP receptor co-agonists described herein comprise or consist of a polypeptide and optionally a substituent z as defined. In some embodiments, the GLP-1/GIP receptor co-agonists display an extended half-life gained by an amino acid residue of the co-agonist conjugated to a $C_{16}$-$C_{22}$ fatty acid, optionally via a linker, as explained above.

In some embodiments, the carboxy terminus of a peptide holds a —$CO_2H$ group. In some embodiments, the compounds may optionally include an amide group (C(=O)—$NH_2$) at the C-terminus, which is a modification substituting —OH with —$NH_2$, such as seen with Parent compound No. 5.

In some embodiments the GLP-1/GIP receptor co-agonist is
$YX_2EGTX_6TSDYSX_{12}X_{13}LX_{15}X_{16}X_{17}AX_{19}X_{20}X_{21}FX_{23}X_{24}WLX_{27}X_{28}GX_3X_{31}X_{32}X_{33}X_{34}X_{35}X_{36}X_{37}X_{38}X_{39}$ (SEQ ID NO.: 1)
with an optional amide modification of the C-terminus, wherein
$X_2$ is Aib or A
$X_6$ is F or V
$X_{12}$ is I or Y
$X_{13}$ is Y, A, L, I or Aib
$X_{15}$ is D or E
$X_{16}$ is K or E
$X_{17}$ is Q or I
$X_{19}$ is A or Q
$X_{20}$ is Q, R, E, H, or K
$X_{21}$ is A or E
$X_{23}$ is I or V
$X_{24}$ is E, Q or N
$X_{27}$ is L or I
$X_{28}$ is A or R
$X_{30}$ is G or absent
$X_{31}$ is P or absent $X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;
and optionally wherein a substituent z comprising a lipophilic moiety such as a fatty acid (e.g. a $C_{16}$-$C_{22}$ carboxylic acid is attached to the GLP-1/GIP receptor co-agonist via a Lysine (K) at position 16, 20, or 33.

In some embodiments, substituent z comprises or consists of a protractor according to Chem. 1, wherein n is 14, 16 or 18 and optionally a linker, wherein the linker comprises or consists of one or more γGlu (Chem. 2) and/or one or more Ado (Chem. 3) and/or one or more Gly (Chem. 4) and/or one or more εLys (Chem. 5). In some embodiments, the substituent z is selected from the group consisting of Chem. 7, Chem. 8, Chem. 10, and Chem. 11.

Dipeptide B

In some embodiments, the dipeptide B is a DKP moiety. In some embodiments, the dipeptide B may be referred to as X-Y (Formula II), wherein X and Y are alpha-amino acids. In some embodiments, the conformation of the amide bond between X and Y is preferably cis to facilitate DKP formation by positioning the alpha-amino group of X in suitable proximity to the alpha-carbonyl group of Y for nucleophilic attack. In some embodiments, the dipeptide B carries a substituent b. In some embodiments, Y is an N-alkylated alpha-amino acid. In some embodiments, Y is an N-alkylated alpha-amino acid linked to B via an amide bond formed between the alpha-carboxylic acid group of Y and an amine of the active drug Z. An "N-alkylated alpha-amino acid" is any alpha-amino acid that is substituted with an alkyl group, such as a $C_1$-$C_{12}$ alkyl or such as a $C_1$-$C_6$ alkyl, at the alpha-amino group of the amino acid, wherein said alkyl group may be linear or cyclic and may be unsubstituted or substituted with additional functional groups, e.g. an amino group (such as in N-(2-aminoethyl)glycine). In some embodiments, the alkyl group is selected from the group consisting of methyl, ethyl, 2-aminoethyl, n-propyl, isopropyl, n-butyl, sec-butyl, isobutyl, tert-butyl, pentyl, n-hexyl. In some embodiment, the alkyl group is selected from methyl, ethyl, 2-aminoethyl, n-propyl, sec-butyl, and n-hexyl. In some embodiment, the alkyl group is methyl. In some embodiments, Y is selected from the group consisting of Sar, N-secBu-Gly, Pro, Pro(4-OH), N-Me-Glu, N-Me-Nor, N-Me-homoAla, N-Me-Ala, N-Me-Lys, Aeg, N-Hex-homoAla, N—Pr-Ala, homoPro, N-Et-Gly, N—Pr-Gly, and N-Me-Phe. In some embodiments, Y is Aeg or Sar.

In some embodiments, X is any alpha-amino acid. In some embodiments, X is any alpha-amino acid linked to Y via an amide bond formed between the alpha-carboxylic acid group of X and the alpha-amino group of Y. In some embodiments, X is selected from the group consisting of Lys, Phe(4-NH$_2$), D-Lys, Ala, Gly, Pro, D-Val, homoPro, D-Pro, D-homoPro, D-Ala, and Aze. In some embodiments, X is selected from the group consisting of Gly, Asp, Leu, Lys, D-Lys, and Pro.

In some embodiments, Y is selected from the group consisting of Sar, N-sBu-Gly, Pro, Pro(4-OH), N-Me-Glu, N-Me-Nor, N-Me-homoAla, N-Me-Ala, N-Me-Lys, N-Hex-homoAla, N—Pr-Ala, homoPro, N—Pr-Gly, N-Et-Gly, and N-Me-Phe, and X is selected from the group consisting of Lys, Phe(4-NH$_2$), and D-Lys. Also or alternatively, In some embodiments, Y is selected from Sar and Aeg, and X is selected from Ala, Gly, D-Lys, Pro, D-Val, homoPro, D-Pro, D-homoPro, D-Ala, and Aze.

In some embodiment the dipeptide, which optionally comprises a substituent b, is selected from Table 5a.

In some embodiments the dipeptide derivative is selected from Table 5b.

TABLE 5a

Non-limiting examples of dipeptides derivatives of DKP moiety.

| X | Y |
|---|---|
| Lys | Sar |
| Lys | N-sBu-Gly |
| Lys | Pro |
| Phe(4-NH$_2$) | Pro |
| Lys | Pro(4-OH) |
| D-Lys | N-Me-Glu |
| Lys | N-Me-Nle |
| Lys | N-Me-homo-Ala |
| D-Lys | Sar |
| D-Lys | N-Me-Ala |
| Lys | N-Me-Glu |
| Lys | N-Me-Lys |
| Ala | N-Me-Lys |
| Gly | Aeg |
| Lys | N-Hex-homoAla |
| D-Lys | Aeg |
| D-Lys | N-Pr-Ala |
| Pro | Aeg |
| D-Val | Aeg |
| Lys | homoPro |
| homoPro | Aeg |
| D-Pro | Aeg |
| D-homoPro | Aeg |
| D-Lys | homoPro |
| D-Ala | Aeg |
| Ala | Aeg |
| Aze | Aeg |
| D-Lys | N-sBu-Gly |
| Lys | N-Me-Ala |
| Lys | N-Pr-Gly |
| Lys | N-Et-Gly |
| Lys | N-Me-Phe |
| D-Lys | N-Pr-Gly |
| Asp | Aeg |
| Leu | Aeg |

TABLE 5b
Non-limiting examples of substituted dipeptides of DKP moiety.
| Substituted dipeptide | dipeptide | substituent b |
|---|---|---|
| 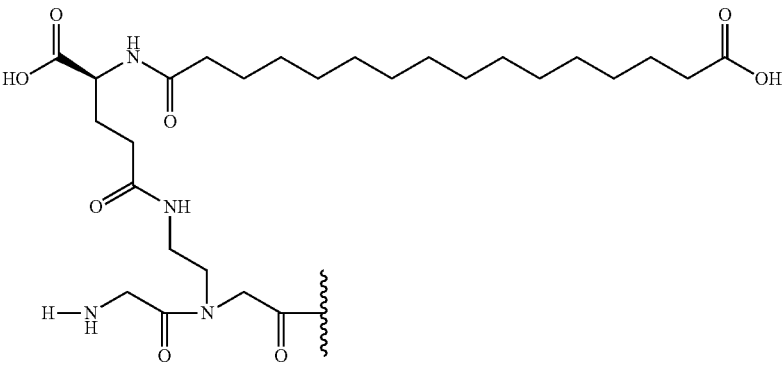 [SMILES: *C(=O)CN(CCNC(=O)CC[C@H](NC(=O)CCCCCCCCCCCCCCC(=O)O)C(=O)O)C(=O)CN] | Gly-Aeg | Chem. 16 |
| 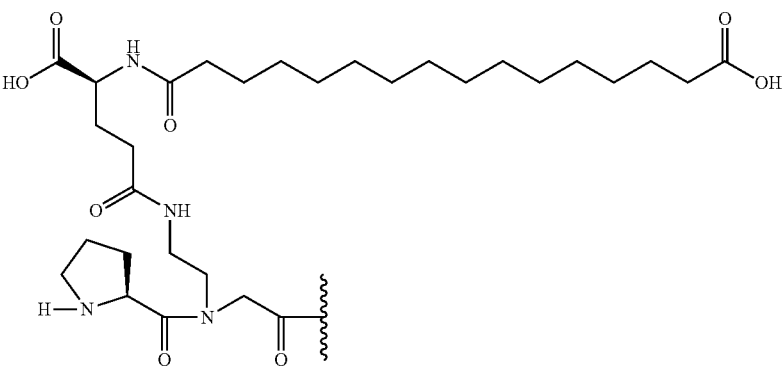 [SMILES: *C(=O)CN(CCNC(=O)CC[C@H](NC(=O)CCCCCCCCCCCCCCC(=O)O)C(=O)O)C(=O)[C@@H]1CCCN1] | Pro-Aeg | Chem. 16 |
| 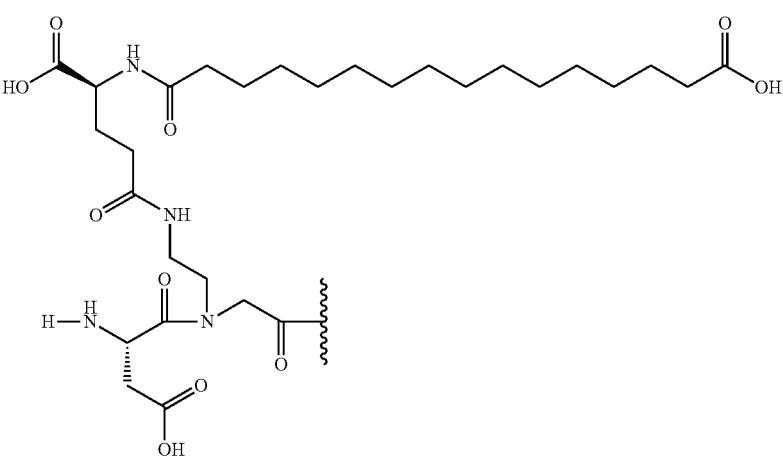 [SMILES: *C(=O)CN(CCNC(=O)CC[C@H](NC(=O)CCCCCCCCCCCCCCC(=O)O)C(=O)O)C(=O)[C@@H](N)CC(=O)O] | Asp-Aeg | Chem. 16 |

TABLE 5b-continued

Non-limiting examples of substituted dipeptides of DKP moiety.

| Substituted dipeptide | dipeptide | substituent b |
|---|---|---|
| | Leu-Aeg | Chem. 16 |
| | Ala-Aeg | Chem. 16 |
| | Lys-Sar | Chem. 16 |

TABLE 5b-continued
Non-limiting examples of substituted dipeptides of DKP moiety.
| Substituted dipeptide | dipeptide | substituent b |
|---|---|---|
| 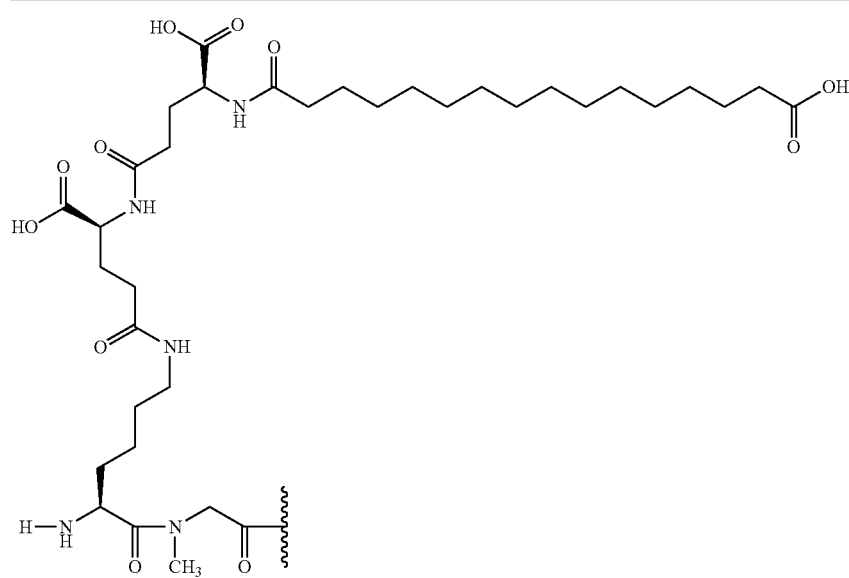 [SMILES: *C(=O)CN(C)C(=O)[C@@H](N)CCCCNC(=O)CC[C@H](NC(=O)CC[C@H](NC(=O)CCCCCCCCCCCCCCC(=O)O)C(=O)O)C(=O)O] | Lys-Sar | Chem. 18 |
| 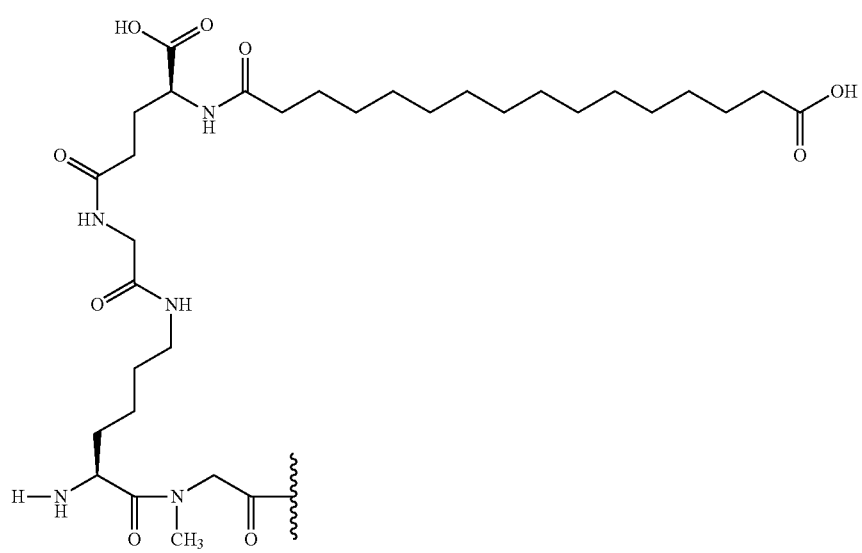 [SMILES: *C(=O)CN(C)C(=O)[C@@H](N)CCCCNC(=O)CNC(=O)CC[C@H](NC(=O)CCCCCCCCCCCCCCC(=O)O)C(=O)O] | Lys-Sar | Chem. 19 |

TABLE 5b-continued

Non-limiting examples of substituted dipeptides of DKP moiety.

| Substituted dipeptide | dipeptide | substituent b |
|---|---|---|
| (structure) | Lys-Sar | Chem 22 |
| (structure) | Lys-Sar | Chem. 17 |

TABLE 5b-continued
Non-limiting examples of substituted dipeptides of DKP moiety.
| Substituted dipeptide | dipeptide | substituent b |
|---|---|---|
| 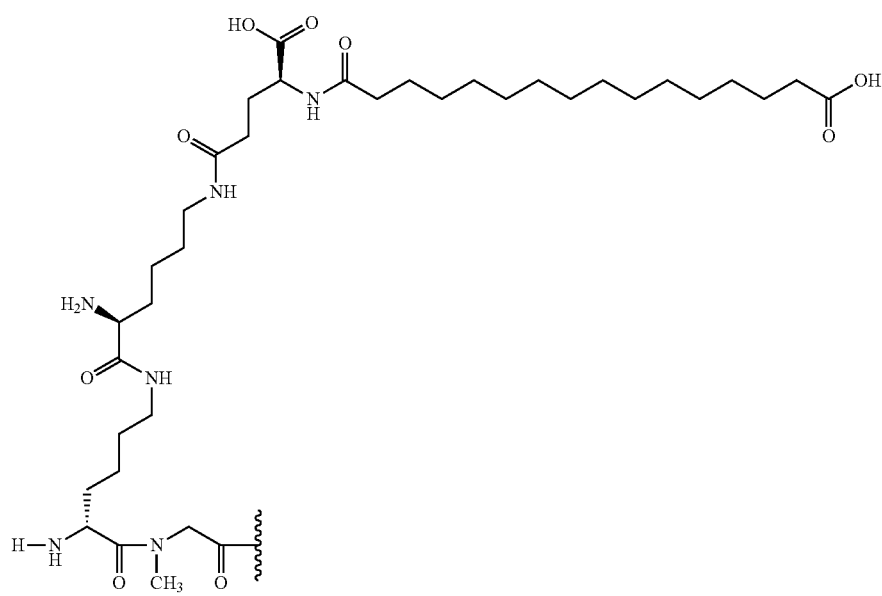 [SMILES: *C(=O)CN(C)C(=O)[C@H](N)CCCCNC(=O)[C@@H](N)CCCCNC(=O)CC[C@H](NC(=O)CCCCCCCCCCCCCCC(=O)O)C(=O)O] | D-Lys-Sar | Chem. 20 |
| 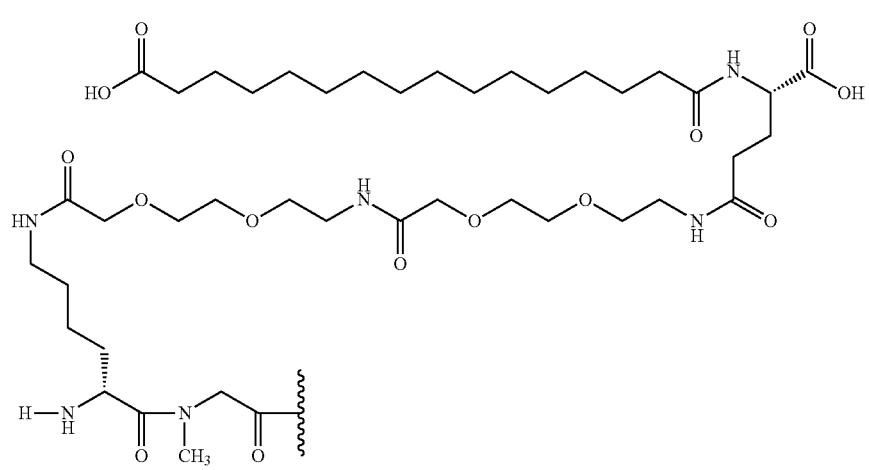 [SMILES: *C(=O)CN(C)C(=O)[C@H](N)CCCCNC(=O)COCCOCCNC(=O)COCCOCCNC(=O)CC[C@H](NC(=O)CCCCCCCCCCCCCCC(=O)O)C(=O)O] | D-Lys-Sar | Chem. 21 |
| 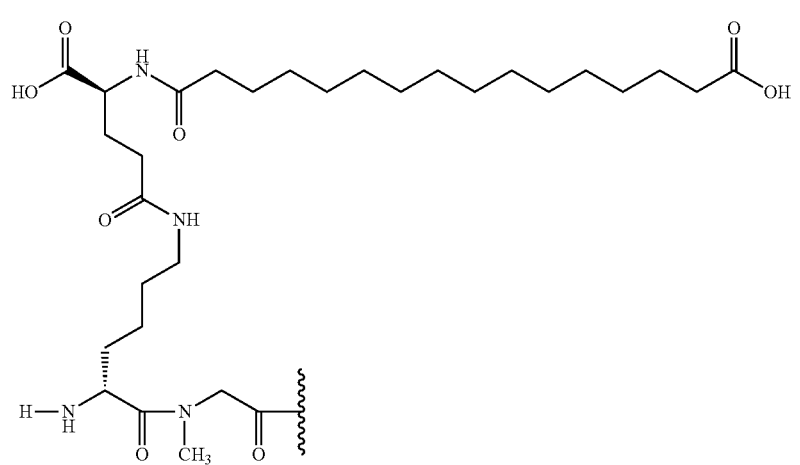 [SMILES: *C(=O)CN(C)C(=O)[C@H](N)CCCCNC(=O)CC[C@H](NC(=O)CCCCCCCCCCCCCCC(=O)O)C(=O)O] | D-Lys-Sar | Chem. 16 |

Active Drug Z

The active drug Z described herein is a GLP-1/GIP receptor co-agonist comprising a substituent z as defined above, in which the substituent z is attached to the GLP-1/GIP receptor co-agonists via an amino acid residue.

Functional Properties

Therapeutic use of pharmacologically active compounds may be hampered by unsuitable pharmacokinetic properties, e.g. because the pharmacokinetic properties are not suitable to reach a desired exposure following administration of the compound. Prodrug technology may be used to improve the pharmacokinetic properties, e.g. to make it suitable for once weekly oral dosing. The exposure level of an active drug following administration of a prodrug relies on the prodrug to drug conversion half-life, and thus obtaining a suitable conversion half-life may render a compound suitable for a specific dosing regimen (e.g. once weekly administration). The exposure level of an active drug following administration of a prodrug relies on the observed terminal half-life of the active drug, and thus obtaining a suitable terminal half-life may render a compound suitable for a specific dosing regimen (e.g. for once weekly administration). The suitability of prodrugs to be administered orally relies on their ability to reach systemic circulation following absorption in the gastrointestinal tract, and thus obtaining a suitable oral bioavailability may render a compound suitable for oral administration (e.g. for once weekly oral administration).

According to a first functional aspect, the compounds as described herein do not exert the intended potency to any significant extent at the human GLP-1 and/or GIP receptor compared to the active drug. Also, or alternatively, in a second functional aspect, the prodrugs as described herein are converted to the active drug under physiological conditions. Also, or alternatively, in a third functional aspect, the prodrugs as described herein have improved pharmacokinetic properties, such as extended terminal half-life following i.v., s.c. and/or p.o. administration.

Functional Receptor Activation Activity

According to the first functional aspect, the prodrugs of the invention do not activate the human GIP-1 receptor and/or human GIP receptor to any significant extent compared to the active drug. The functional activity of the GLP-1/GIP receptor agonists as described herein can be tested in vitro as described herein in General methods for measuring in vitro functional potency.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of compounds may thus be determined as described herein and the $EC_{50}$ determined. The lower the $EC_{50}$ value, the better the potency.

In order to characterise such compounds, it may further be relevant to consider the in vitro potencies relative to the native hormones of each receptor.

The in vitro potency may, e.g., be determined in a medium containing membranes expressing the appropriate GLP-1 and/or GIP receptor, and/or in an assay with whole cells expressing the appropriate GLP-1 and/or GIP receptor.

For example, the functional response of the human GLP-1 and/or GIP receptor may be measured in a reporter gene assay, e.g. in a stably transfected BHK cell line that expresses the human GLP-1 and/or GIP receptor and contains the DNA for the cAMP response element (CRE) coupled to a promoter and the gene for firefly luciferase (CRE luciferase). When cAMP is produced as a result of activation of the GLP-1 and/or GIP receptor, this in turn results in luciferase being expressed. Luciferase may be determined by adding luciferin, which by the enzyme is converted to oxyluciferin and produces bioluminescence, which is measured as a reporter of the in vitro potency. One example of such an assay is described in Example 5 as described herein. Since the compounds may include one or more substituent designed to bind albumin, it is also important to note that the receptor activity may be affected by the presence or absence of human serum albumin (HSA) in the assay medium. A decrease in potency of the compound in the presence of HSA, indicated by an increase in $EC_{50}$ compared to the $EC_{50}$ in the absence of HSA, indicates interaction of the compounds with HSA and predicts a protracted time of action in vivo.

In one embodiment, the active drugs have potent in vitro effects to activate the human GLP-1 and GIP receptors.

In one embodiment, the parent compounds are capable of activating the human GLP-1 and GIP receptors in vitro with an $EC_{50}$ of less than 20 pM in CRE luciferase reporter assays as described in Example 2 herein, when performed without HSA.

In one embodiment, the parent compounds have an in vitro potency at the human GLP-1 and GIP receptors determined using the method of Example 2 corresponding to an $EC_{50}$ at or below 100 pM, more preferably below 50 pM, or most preferably below 20 pM.

In one embodiment, the $EC_{50}$ in human GLP-1 and GIP receptors assays are both 1-25 pM, such as 1-20 pM, such as 1-15 pM or such as 1-10 pM.

Conversion Half-Life

According to the second functional aspect, the prodrugs of the invention have a surprisingly good conversion half-lives.

The rate with which the conversion of the prodrug to the active drug takes place may be quantified by the conversion half-life. The term "conversion half-life" as used herein refers to the length of time required for the concentration of the prodrug to be reduced to half by conversion.

A desirable conversion half-life for a prodrug intended for once weekly oral dosing in human may be 24-500 hours, such as 50-400 hours, such as 75-300 hours, or such as 100-200 hours, when measured at pH 7.4 and 37° C. as described herein in 'General Methods for Measuring Conversion Half-life'.

The prodrug may achieve the desired conversion upon intramolecular cyclization of DKP moiety whereupon the moiety is cleaved from the active drug, resulting in the liberation of the active drug. Such an intramolecular cyclization may take place as an enzyme-independent processes under physiological conditions, e.g. via 2,5-diketopiperazine (DKP) formation. In a prodrug which is capable of being converted to the active drug via DKP formation, the moiety from which the active drug is liberated upon conversion, is referred to as the DKP moiety. The conversion half-life relies, inter alia, on the nature of the DKP moiety, and thus the conversion half-life can be improved (e.g. to make it suitable for once weekly oral administration), e.g. by means of molecular design of the DKP moiety, to make the properties of the prodrug suitable for a certain dosing regimen (e.g. for once weekly oral administration).

In some embodiments, the conversion half-life is suitable for once daily administration. In some embodiments, the conversion half-life is suitable for once weekly administration. In some embodiments, the conversion half-life is >24 hours. In some embodiments, the conversion half-life is >50 hours. In some embodiments, the conversion half-life is >75 hours. In some embodiments, the conversion half-life is >100 hours. In some embodiments, the conversion half-life is <500 hours. In some embodiments, the conversion half-life is <400 hours. In some embodiments, the conversion half-life is <300 hours. In some embodiments, the conversion half-life is <200 hours.

In some embodiments, the conversion half-life is 24-500 hours. In some embodiments, the conversion half-life is 50-400 hours. In some embodiments, the conversion half-life is 75-300 hours. In some embodiments, the conversion half-life is 100-200 hours.

Observed Terminal Half-Life

Many drugs display a biphasic plasma disposition curve, which initially follows a steep slope and subsequently follows a shallow slope. The phase which follows a shallow slope may be referred to as the "terminal phase". The term "terminal half-life" as used herein refers to the time required for the plasma concentration of a compound to be reduced to half during the terminal phase. The terminal half-life of a drug when administered in its free form is different from that of the drug when administered as a prodrug since when administered as a prodrug a continuous liberation of the drug in its free form takes place upon conversion of the prodrug in vivo.

The plasma concentration of an active drug administered as a prodrug is a result of, inter alia, the elimination of the active drug from the blood stream as well as the gradual conversion of the prodrug to the active drug. The gradual conversion of prodrug ensures a continued supply of active drug, thus reducing the number of required administrations needed for desired exposure levels as compared to when a drug is administered in its free form. The continued supply of active drug to the blood stream is reflected in the observed terminal half-life (i.e. the measurable terminal half-life), which is higher for an active drug when administered as a prodrug as compared to when administered in its free form.

The pharmacokinetic properties of the prodrugs or the active drugs of the prodrugs of the invention may suitably be determined by in vivo pharmacokinetic studies. Such studies are conducted to evaluate how pharmaceutical compounds are absorbed, distributed, and eliminated in the body, and how these processes affect the concentration of the compound in the body, over the course of time. In the discovery and preclinical phase of pharmaceutical drug development, animal models such as the mouse, rat, monkey, dog, minipig or pig, may be used to perform this characterisation. Any of these models can be used to test the pharmacokinetic properties of the prodrugs of the invention. In such studies, animals are typically administered with a single dose of the drug, either intravenously (i.v.), subcutaneously (s.c.), or orally (p.o.), in a relevant formulation. Blood samples are drawn at predefined time points after dosing, and samples are analysed for concentration of drug with a relevant quantitative assay. Based on these measurements, plasma concentration profiles for the compound of study are plotted and a so-called non-compartmental pharmacokinetic analysis of the data is performed. For most compounds, the terminal part of the plasma concentration profiles will be linear when drawn in a semi-logarithmic plot, reflecting that the drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

When investigating an active drug administered as a prodrug, the terminal half-life of the active drug is influenced by the continuous supply of the active drug resulting from gradual conversion of the prodrug, because the prodrug acts as a depot from which the drug is slowly released. Analysis of the terminal half-life of an active drug administered as a prodrug is thus most conveniently referred to as the "observed terminal half-life" since it will not be the same as when the active drug is administered in its free form.

In some embodiments, the terminal half-life of the prodrugs of the invention are determined as described herein in 'General Methods for Measuring Terminal Half-Life in Minipigs'. An observed terminal half-life suitable for once weekly oral administration in humans, when determined in mini-pigs, may be >50 hours, or preferably be >70 hours, or most preferably >90 hours. An observed terminal half-life suitable for once weekly oral administration in humans, when determined in mini-pigs, may be <250 hours, or may preferably be <180 hours. An observed terminal half-life suitable for once weekly oral administration in humans, when determined in mini-pigs, may be in the range of 50-250 hours, or may preferably be in the range of 90-180 hours.

Oral Bioavailability

Oral treatment with pharmacological active compounds may be hampered by poor bioavailability. The term "bioavailability" refers to the capability of a compound to reach systemic circulation following administration, and it may be quantified as the fractional extent of the compound dosage that reaches systemic circulation upon administration. It is desirable that a drug intended for oral administration has a high oral absorption (i.e. a high absorption form the gastrointestinal tract following oral administration) since it may reduce the dosage required to reach the intended systemic concentration of the drug, and thus e.g. reduce tablet size and manufacturing costs.

The term "oral bioavailability" as used herein refers to the capability of a compound to reach systemic circulation following oral administration. The oral bioavailability reflects the extent to which a compound is absorbed in the gastrointestinal tract following oral administration. In other words, a high oral bioavailability is associated with a high oral absorption. A high oral bioavailability of a drug is associated with a high drug exposure following oral administration. The oral bioavailability may be measured in a co-formulation with the absorption enhancer sodium N-(8-[2-hydroxybenzoyl] amino) caprylate (SNAC) in beagle dogs as described in WO2019/149880.

The oral bioavailability may be measured as described herein in General Methods for Measuring Oral Bioavailability in Beagle Dogs. In some embodiments, the compounds as described herein have a high oral bioavailability. In some embodiments, the compounds as described herein have an oral bioavailability that is similar to that of active drug. In some embodiments, the compounds as described herein have an oral bioavailability that is not inferior to that of active drug. In some embodiments, the compounds as described herein have an oral bioavailability that is as least as high as that of active drug. In some embodiments, the compounds as described herein have an oral bioavailability which is suitable for once weekly oral dosing in humans. In some embodiments, the compounds as described herein have an oral bioavailability which is determined in Beagle dogs and measured as $C_{max}$/Dose [kg/L]. In some embodiments, the compounds as described herein have an oral bioavailability which is measured as $C_{max}$/Dose [kg/L] in Beagle dogs; wherein the $C_{max}$/Dose [kg/L] is >0.10, preferably is >0.15, and most preferably is >0.20. In some embodiments, the compounds as described herein have an oral bioavailability which is determined in Beagle dogs and measured as AUC/Dose [kg*hr/L]. In some embodiments, the compounds as described herein have an oral bioavailability which is determined in Beagle dogs and measured as AUC/Dose [kg*hr/L]; wherein the AUC/Dose [kg*hr/L] is >2.0, preferably is >5.0, and most preferably is >10.0.

Pharmaceutical Compositions

Pharmaceutical compositions comprising a prodrug as described herein or a pharmaceutically acceptable salt thereof, and optionally one or more a pharmaceutically acceptable excipients may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, filler, binder, lubricant, glidant, disintegrant, flow control agent, crystallization inhibitor, solubilizer, stabilizer, coloring agent, flavouring agent, surfactant, emulsifier or combinations thereof and/or to improve administration, and/or to improve absorption of the active substance. The amount of each excipient used may vary within ranges conventional in the art. Techniques and excipients which may be used to formulate oral dosage forms are described in Handbook of Pharmaceutical Excipients (e.g. $8^{th}$ edition, Sheskey et al., Eds., American Pharmaceuticals Association and Pharmaceutical Press, publications department of the Royal Pharmaceutical Society of Great Britain (2017), and any later editions); and Remington: The Science and Practice of Pharmacy (e.g. 22nd edition, Remington and Allen, Eds., Pharmaceutical Press (2013), and any later editions).

The pharmaceutical composition comprising compounds as described herein may be of several dosage forms, e.g. a solution, a suspension, a tablet, and a capsule. The pharmaceutical composition comprising the prodrug of the invention may be administered to a patient in need thereof at several sites, e.g. at topical sites such as skin or mucosal sites; at sites which bypass absorption such as in an artery, in a vein, or in the heart; and at sites which involve absorption, such as in the skin, under the skin, in a muscle, orally, or in the abdomen. An administered dose may contain from 0.1 ug/kg to 100 mg/kg of the compound of the invention.

In some embodiments, the pharmaceutical composition may be a solid formulation, e.g. a freeze-dried or spray-dried composition, which may be used as is, or whereto the physician or the patient adds solvents, and/or diluents prior to use. In one embodiment, the pharmaceutical composition is in the form of a tablet. In a further embodiment, the pharmaceutical composition may be a solid formulation comprising or consisting of the prodrug of the invention, a salt of N-[8-(2-hydroxybenzoyl)amino]caprylate, such as sodium N-[8-(2-hydroxybenzoyl)amino]caprylate (SNAC), and one or more further excipients as is known in the art, e.g. using any one or more of the formulations described in WO 2012/080471, WO 2013/189988, or WO 2019/149880. In one embodiment, the pharmaceutical formulation is a tablet comprising the prodrug of the invention, SNAC and one or more further excipients.

Alternatively, the pharmaceutical composition is a liquid formulation, such as an aqueous formulation. Liquid compositions, suitable for injection, can be prepared using conventional techniques of the pharmaceutical industry which involve dissolving and mixing the ingredients as appropriate to give the desired end product. Thus, according to one procedure, a compound according to the invention is dissolved in a suitable buffer at a suitable pH. The composition may be sterilised, for example, by sterile filtration.

Pharmaceutically Acceptable Salts

In some embodiments, the prodrugs as described herein are in the form of a pharmaceutically acceptable salt. Salts are e.g. formed by a chemical reaction between a base and an acid, e.g.: $2NH_3 + H_2SO_4 \rightarrow (NH_4)_2SO_4$. The salt may be a basic salt, an acid salt, or it may be neither (i.e. a neutral salt). Basic salts produce hydroxide ions and acid salts hydronium ions in water. The salts of the prodrugs may be formed with added cations or anions between anionic or cationic groups, respectively. These groups may be situated in the peptide and/or in the substituent of the derivatives.

Non-limiting examples of anionic groups include any free carboxylic acid groups in the substituent, if any, as well as in the peptide. The peptide may include a free carboxylic acid group at the C-terminus, if present, as well as any free carboxylic acid group of amino acid residues such as aspartic acid and glutamic acid.

Non-limiting examples of cationic groups include any free amino groups in the substituent, if any, as well as in the peptide. The peptide may include a free amino group at the N-terminus, if present, as well as any free imidazole, guanidine, or amino group of amino acid residues such as histidine, arginine, and lysine.

In a particular embodiment, the prodrug of the invention is in the form of a pharmaceutically acceptable salt.

Pharmaceutical Indications

A further aspect of the invention relates to the compounds as described herein for use as a medicament. The term "treatment", as used herein, refers to the medical treatment of any human subject in need thereof. The treatment may be preventive, prophylactic, palliative, symptomatic and/or curative. The timing and purpose of said treatment may vary from one individual to another, according to the status of the subject's health.

In some embodiments, the compounds described herein are for use in the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) prevention and/or treatment of eating disorders, such as overweight or obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(iv) weight maintenance after successful weight loss (either drug induced or by diet and exercise)—i.e. prevention of weight gain after successful weight loss.

(v) prevention and/or treatment of liver disorders, such as hepatic steatosis, non-alcoholic fatty liver disease (NAFLD), non-alcoholic steatohepatitis (NASH), liver inflammation or fatty liver.

In some embodiments, the compounds are for use in a method for prevention and/or treatment of diabetes and/or obesity. In some embodiments, the compounds are for use in a method for treatment of diabetes and/or obesity.

In some embodiments, the compounds are for use in a method for treatment or prevention of type 2 diabetes. In some embodiments, the compounds are for use in a method for treatment of type 2 diabetes. In some embodiments, the compounds are for use in a method for treatment or prevention of obesity. In some embodiments, the compounds are for use in a method for treatment of obesity. In some embodiments, the compounds are for use in a method for weight management. In some embodiments, the compounds are for use in a method for reduction of appetite. In some embodiments, the compounds are for use in a method for reduction of food intake.

Production Processes

The prodrugs of the invention (or fragments thereof) may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999; Florencio Zaragoza Dörwald, "Organic Synthesis on Solid Phase", Wiley-VCH Verlag GmbH, 2000; and "Fmoc Solid Phase Peptide Synthesis", Edited by W. C. Chan and P. D. White, Oxford University Press, 2000.

Specific examples of methods of preparing the prodrugs are included in the experimental part.

In some embodiments, the method for preparing a compound as described herein comprises a step of solid phase peptide synthesis. The dipeptide moiety and/or substituent may be built sequentially as part of the solid phase peptide synthesis or produced separately and attached via an appropriate functional group of the peptide after peptide synthesis.

In one embodiment, the compounds are produced by a two-step process whereby two peptide fragments are ligated after attachment of the substituent to one of the peptide fragments.

EMBODIMENTS

The invention is further described by the following non-limiting embodiments:

1. A compound of Formula I:

B-Z    (Formula I)

or a pharmaceutical acceptable salt, ester or amide thereof, wherein B is a dipeptide, said dipeptide optionally comprising a substituent b;
wherein Z is a GLP-1/GIP receptor co-agonist, said GLP-1/GIP receptor co-agonist optionally comprising a substituent z; and
wherein the N-terminal amino group of the GLP-1/GIP receptor co-agonist is linked to B via a peptide bond.

2. The compound according to embodiment 1, or a pharmaceutically acceptable salt, ester or amide thereof, wherein the amino acid sequence of the GLP-1/GIP receptor co-agonist is
YX$_2$EGTX$_6$TSDYSX$_{12}$X$_{13}$LX$_{15}$X$_{16}$X$_{17}$AX$_{19}$X$_{20}$X$_{21}$FX$_{23}$X$_{24}$WLX$_{27}$X$_{28}$GX$_3$X$_{31}$X$_{32}$X$_{33}$X$_{34}$X$_{35}$X$_{36}$X$_{37}$X$_{38}$X$_{39}$ (SEQ ID NO.: 1), wherein
X$_2$ is Aib or A
X$_6$ is F or V
X$_{12}$ is I or Y
X$_{13}$ is Y, A, L, I or Aib
X$_{15}$ is D or E
X$_{16}$ is K or E
X$_{17}$ is Q or I
X$_{19}$ is A or Q
X$_{20}$ is Q, R, E, H, or K
X$_{21}$ is A or E
X$_{23}$ is I or V
X$_{24}$ is E, Q or N
X$_{27}$ is L or I
X$_{28}$ is A or R
X$_{30}$ is G or absent
X$_{31}$ is P or absent
X$_{32}$ is E, S or absent
X$_{33}$ is S, K or absent
X$_{34}$ is G or absent
X$_{35}$ is A or absent
X$_{36}$ is P or absent
X$_{37}$ is P or absent
X$_{38}$ is P or absent
X$_{39}$ is S or absent.

3. The compound according to embodiment 1, or a pharmaceutically acceptable salt, ester or amide thereof, wherein the amino acid sequence of the GLP-1/GIP receptor co-agonist is
Y-Aib-EGTFTSDYSIX$_{13}$LX$_{15}$X$_{16}$X$_{17}$AX$_{19}$X$_{20}$X$_{21}$FX$_{23}$X$_{24}$WLX$_{27}$AGGPSX$_{33}$GAPPPS (SEQ ID NO.: 2), wherein
X$_{13}$ is L or Aib,
X$_{15}$ is D or E,
X$_{16}$ is K or E,
X$_{17}$ is Q or I,
X$_{19}$ is A or Q,
X$_{20}$ is R or K
X$_{21}$ is A or E
X$_{23}$ is I or V
X$_{24}$ is E or Q
X$_{27}$ is L or I;
X$_{33}$ is S or K.

4. The compound according to embodiment 1, or a pharmaceutically acceptable salt, ester or amide thereof, wherein the amino acid sequence of the GLP-1/GIP receptor co-agonist is
Y-Aib-EGTFTSDYSILLEX$_{16}$QAAREFIEWLLAGGPSX33GAPPPS (SEQ ID NO.: 3), wherein
X$_{16}$ is K or E,
X$_{33}$ is S or K.

5. The compound according to any one of embodiments 2 to 4, or a pharmaceutically acceptable salt, ester or amide thereof, wherein X$_{16}$ is E and X$_{33}$ is K.

6. The compound according to any one of embodiments 2 to 4, or a pharmaceutically acceptable salt, ester or amide thereof, wherein X$_{16}$ is K and X$_{33}$ is S.

7. The compound according to any one of the preceding embodiments, or a pharmaceutically acceptable salt, ester or amide thereof, wherein the amino acid sequence of the GLP-1/GIP receptor co-agonist is Y-Aib-EGTFTSDYSI-Aib-LDKIAQKAFVQWLIAGGPSSGAPPPS (SEQ ID NO.: 4).

8. The compound according to any one of the preceding embodiments, or a pharmaceutically acceptable salt, ester or amide thereof, wherein the amino acid sequence of the GLP-1/GIP receptor co-agonist is selected from the group consisting of Y-Aib-EGTFTSDYSI-Aib-LDKIAQKAFVQWLIAGGPSGAPPPS (SEQ ID NO.: 4), Y-Aib-EGTFTSDYSILLEEQAAREFIEWLLAGGPSKGAPPPS (SEQ ID NO.: 5), and Y-Aib-EGTFTSDYSILLEKQAAREFIEWLLAGGPSSGAPPPS (SEQ ID NO.: 6).

9. The compound according to any one of the preceding embodiments, or a pharmaceutically acceptable salt, ester or amide thereof, wherein the amino acid sequence of the GLP-1/GIP receptor co-agonist is Y-Aib-EGTFTSDYSILLEEQAAREFIEWLLAGGP SKGAPPPS (SEQ ID NO.: 5) or Y-Aib-EGTFTSD YSILLEKQAAREFIEWLLAGGPSSGAPPPS (SEQ ID NO.: 6).

10. The compound according to any one of embodiments 1 to 9, or a pharmaceutically acceptable salt, ester or amide thereof, wherein the GLP-1/GIP receptor co-agonist comprises a substituent z, and wherein the substituent z is attached to the GLP-1/GIP receptor co-agonist via a lysine (K).

11. The compound according to any one of embodiments 2 to 10, or a pharmaceutically acceptable salt, ester or amide thereof, wherein $X_{16}$ and/or $X_{20}$ and/or $X_{33}$ is lysine.

12. The compound according to any one of embodiments 2, 3, 11, or 6, or a pharmaceutically acceptable salt, ester or amide thereof, wherein $X_{16}$ is lysine.

13. The compound according to any one of embodiments 2, 11, or 7, or a pharmaceutically acceptable salt, ester or amide thereof, wherein $X_{20}$ is lysine.

14. The compound according to any one of embodiments 2, 3, 11, or 5, or a pharmaceutically acceptable salt, ester or amide thereof, wherein $X_{33}$ is lysine.

15. The compound according to any one of embodiments 1 to 14, or a pharmaceutically acceptable salt, ester or amide thereof, wherein the substituent z is attached to the GLP-1/GIP receptor co-agonist via a lysine (K) at position 16, 20 or 33.

16. The compound according to any one of embodiments 1 to 15, or a pharmaceutically acceptable salt, ester or amide thereof, wherein GLP-1/GIP receptor co-agonist has the amide modification of the C-terminus.

17. The compound according to any one of embodiments 5, 8 or 9, or a pharmaceutically acceptable salt, ester or amide thereof, wherein the lysine at position 33 is chemically modified through conjugation to the epsilon-amino group of the lysine side-chain with Chem. 8, Chem. 7 or Chem. 10.

18. The compound according to any one of embodiments 6, 8 or 9, or a pharmaceutically acceptable salt, ester or amide thereof, wherein the lysine at position 16 is chemically modified through conjugation to the epsilon-amino group of the lysine side-chain with Chem. 7.

19. The compound according to embodiment 7 or embodiment 8, or a pharmaceutically acceptable salt, ester or amide thereof, wherein the lysine at position 20 is chemically modified through conjugation to the epsilon-amino group of the lysine side-chain with Chem. 11.

20. The compound according to any one of embodiments 1 to 19, or a pharmaceutically acceptable salt, ester or amide thereof, wherein the dipeptide B is of Formula II:

$$X-Y \quad \text{(Formula II)},$$

wherein X is any alpha-amino acid linked to Y via an amide bond formed between the alpha-carboxylic acid group of X and the alpha-amino group of Y,
wherein Y is an N-alkylated alpha-amino acid linked to Z via a peptide bond formed between the alpha-carboxylic acid group of Y and the N-terminal amino group of the GLP-1/GIP receptor co-agonist.

21. The compound according to any one of embodiments 1 to 16, or a pharmaceutically acceptable salt, ester or amide thereof, wherein the dipeptide B is of Formula II:

$$X-Y \quad \text{(Formula II)},$$

wherein X is any alpha-amino acid linked to Y via an amide bond formed between the alpha-carboxylic acid group of X and the alpha-amino group of Y,
wherein Y is an N-alkylated alpha-amino acid linked to Z via a peptide bond formed between the alpha carboxylic acid group of Y and an N-terminal amino group of Z.

22. The compound according to embodiment 20 or embodiment 21, or a pharmaceutically acceptable salt, ester or amide thereof, wherein Y is selected from the group consisting of sarcosine, N-sec-butylglycine, proline, trans-4-hydroxyproline, N-methylglutamate, N-methylnorleucine, N-methylhomoalanine, N-methylalanine, N-methyllysine, N-(2-aminoethyl)glycine, N-hexylhomoalanine, N-propylalanine, homoproline, N-propylglycine, N-ethylglycine, and N-methylphenylalanine.

23. The compound according to any one of embodiments 20 to 22, or a pharmaceutically acceptable salt, ester or amide thereof, wherein X is selected from the group consisting of lysine, 4-aminophenylalanine, D-lysine, alanine, glycine, proline, D-valine, homoproline, D-proline, D-homoproline, D-alanine, and azetidine-2-carboxylic acid.

24. The compound according to any one of embodiments 20 to 23, or a pharmaceutically acceptable salt, ester or amide thereof, wherein, wherein Y is selected from the group consisting of sarcosine, N-sec-butylglycine, proline, trans-4-hydroxyproline, N-methylglutamate, N-methylnorleucine, N-methylhomoalanine, N-methylalanine, N-methyllysine, N-hexylhomoalanine, N-propylalanine, homoproline, N-propylglycine, N-ethylglycine, and N-methylphenylalanine.

25. The compound according to any one of embodiments 20 to 24, or a pharmaceutically acceptable salt, ester or amide thereof, wherein Y is sarcosine or N-(2-aminoethyl)glycine.

26. The compound according to any one of embodiments 20 to 25, or a pharmaceutically acceptable salt, ester or amide thereof, wherein X is selected from the group consisting of lysine, D-lysine, alanine, leucine, glycine, proline, and aspartic acid.

27. The compound according to any one of embodiments 20 to 26, or a pharmaceutically acceptable salt, ester or amide thereof, wherein X is selected from the group consisting of lysine, D-lysine, and glycine.

28. The compound according to any one of embodiments 1 to 27, or a pharmaceutically acceptable salt, ester or amide thereof, wherein dipeptide is capable of undergoing an intramolecular cyclisation to form a 2,5-diketopiperazine (DKP) such that the amide bond between A and Z is cleaved.

29. The compound according to any one of embodiments 1 to 27, or a pharmaceutically acceptable salt, ester or amide thereof, wherein dipeptide is capable of undergoing an intramolecular cyclization to form a 2,5-diketopiperazine (DKP) such that the peptide bond between A and Z is cleaved.

30. The compound according to any one of embodiments 1 to 29, or a pharmaceutically acceptable salt, ester or amide thereof, wherein the dipeptide comprises a substituent b.

31. The compound according to any one of embodiments 1 to 29, or a pharmaceutically acceptable salt, ester or amide thereof, wherein the dipeptide carries a substituent b.

32. The compound according to any one of embodiments 1 to 29, or a pharmaceutically acceptable salt, ester or amide thereof, wherein the dipeptide has a substituent b.

33. The compound according to any one of embodiments 21 to 30, or a pharmaceutically acceptable salt, ester or amide thereof, wherein a substituent b is covalently attached to X optionally via an amide bond.

34. The compound according to any one of embodiments 21 to 30, or a pharmaceutically acceptable salt, ester or amide thereof, wherein a substituent b is covalently attached to Y optionally via an amide bond.

35. The compound according to any one of embodiments 1 to 34, or a pharmaceutically acceptable salt, ester or amide thereof, wherein the substituent b is an albumin binding moiety.

36. The compound according to any one of embodiments 1 to 35, or a pharmaceutically acceptable salt, ester or amide thereof, wherein the substituent b comprises or consists of a protractor and optionally a linker.

37. The compound according to embodiment 36, or a pharmaceutically acceptable salt, ester or amide thereof, wherein the protractor is a fatty acid such as a $C_{16}$-$C_{22}$ carboxylic acid.

38. The compound according to embodiment 36 or embodiment 37, or a pharmaceutically acceptable salt, ester or amide thereof, wherein the protractor is Chem. 1.

39. The compound according to any one of embodiments 1 to 38, or a pharmaceutically acceptable salt, ester or amide thereof, wherein the substituent comprises a linker and optionally wherein the linker comprises or consists of linker elements.

40. The compound according to any one of embodiments 38 to 39, or a pharmaceutically acceptable salt, ester or amide thereof, wherein the linker is of formula IV $$A_1\text{-}A_2\text{-}A_3\text{-}A_4\text{-}A_5 \qquad \text{(Formula IV)},$$

wherein $A_1$ is covalently bound to an amino acid of the dipeptide via an amide bond and optionally also covalently bound to the protractor via an amide bond and is selected from a group consisting of Chem. 2, Chem. 3, Chem. 4, and Chem. 5; wherein $A_5$ is covalently bound to Chem. 1 and is Chem. 2 or absent; wherein each of $A_2$, $A_3$, and $A_4$, are individually selected from the group consisting of Chem. 2, Chem. 3, Chem. 4, and Chem. 5, or is absent.

41. The compound according to any one of embodiments 1 to 40, or a pharmaceutically acceptable salt, ester or amide thereof, wherein the substituent b is selected from the group consisting of Chem. 16, Chem. 17, Chem. 18, Chem 19, Chem. 20, Chem 21, and Chem. 22.

42. The compound according to any one of embodiments 1 to 41, or a pharmaceutically acceptable salt, ester or amide thereof, wherein the compound is selected from the group consisting of:

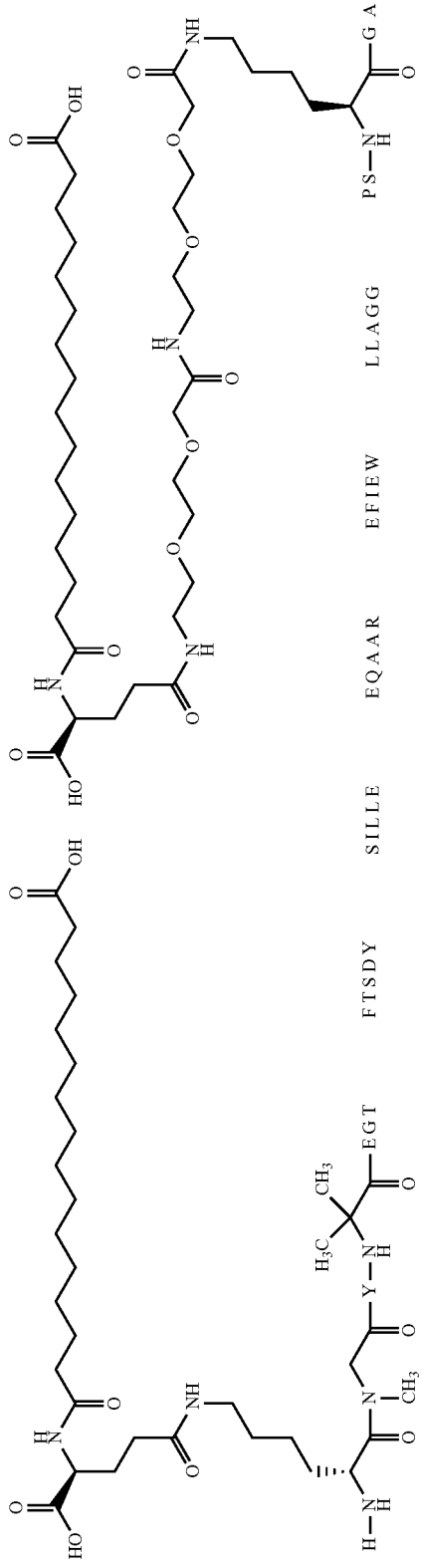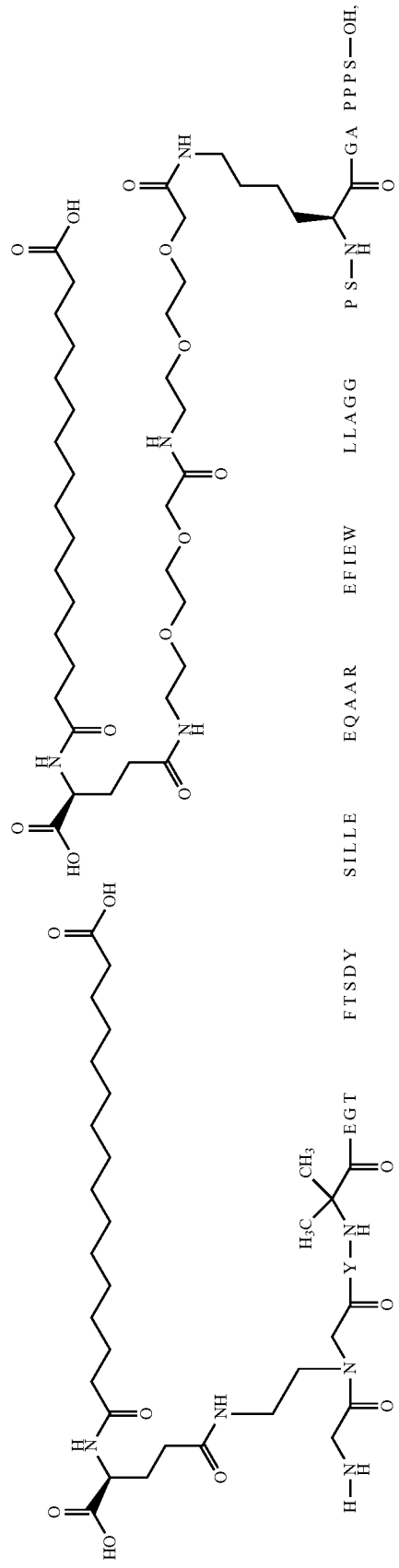

-continued
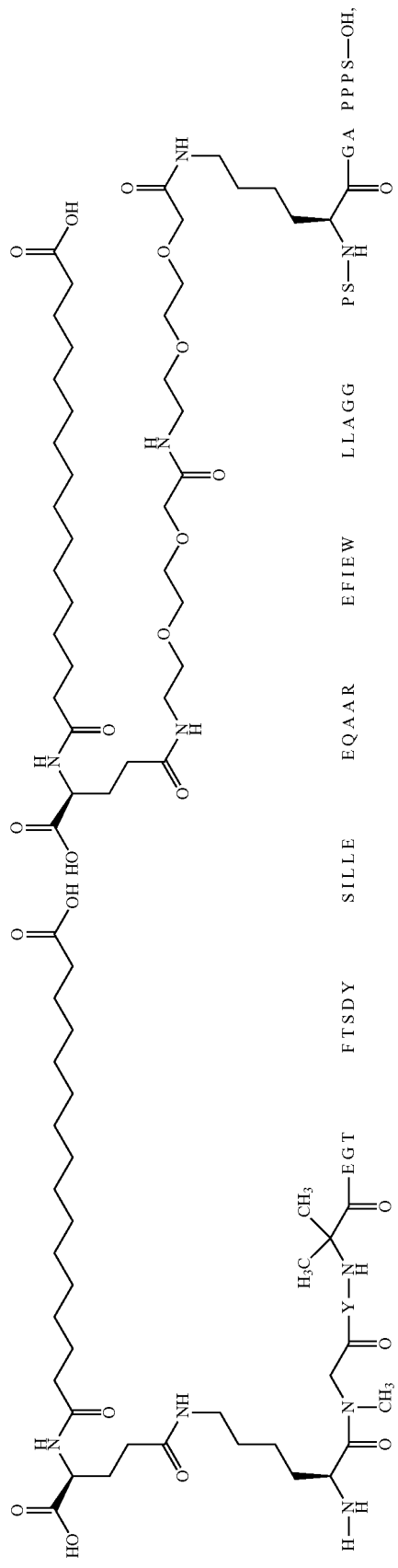
Compound No. 3
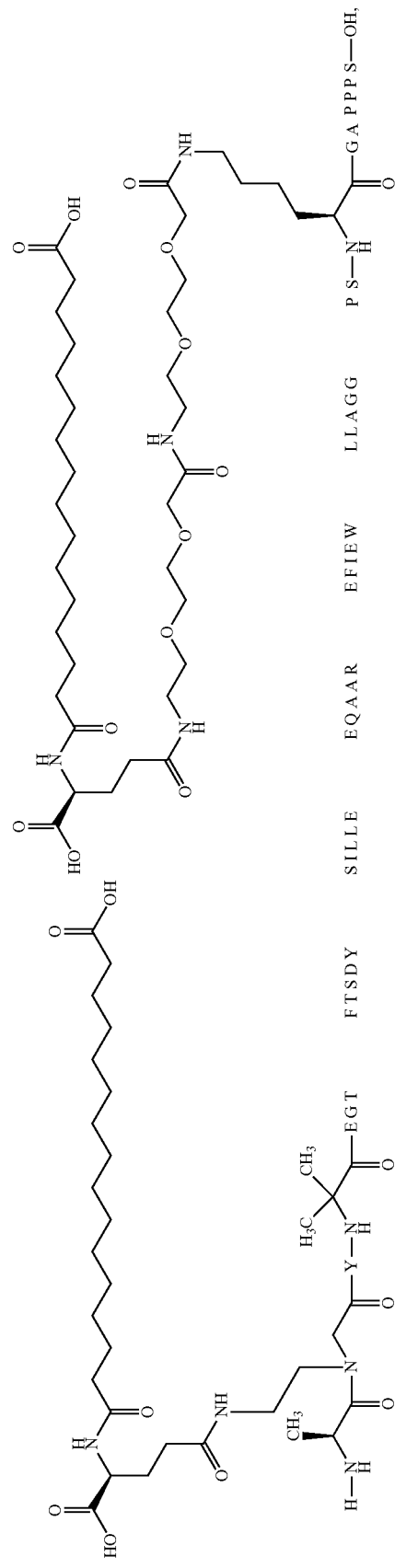
Compound No. 4

-continued
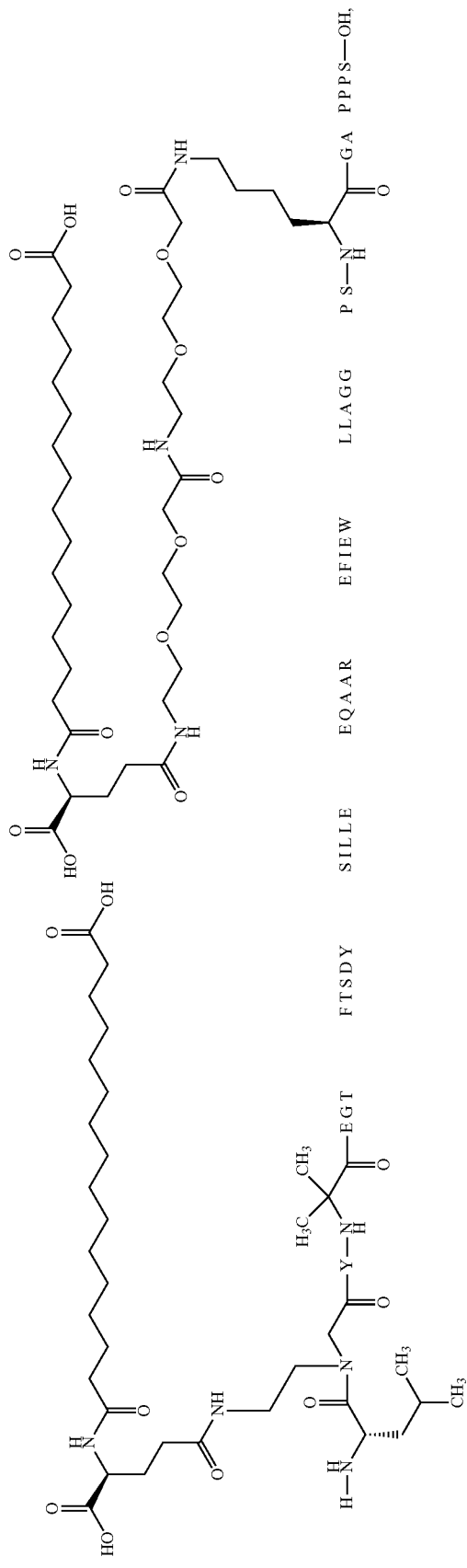
Compound No. 5
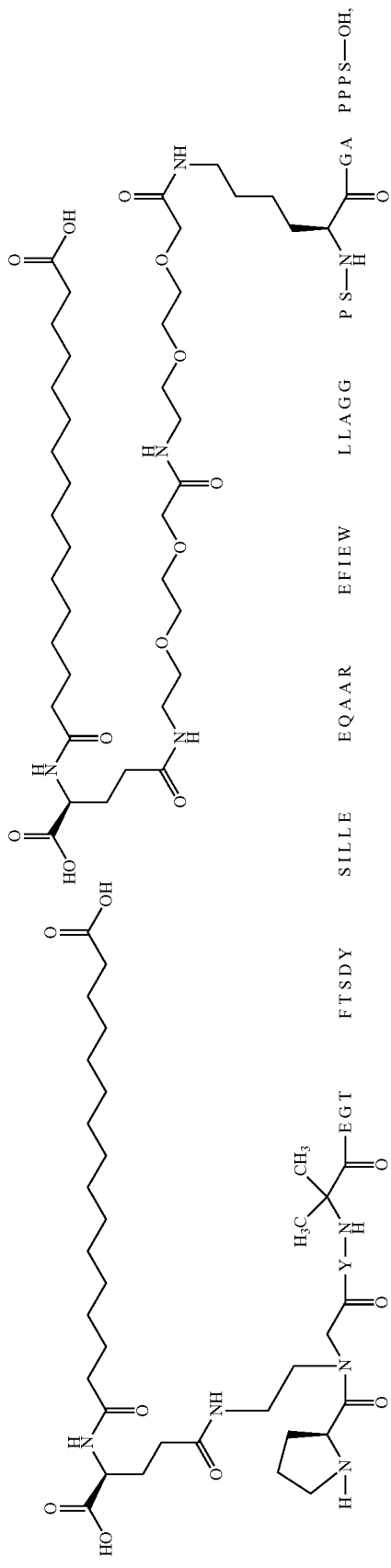
Compound No. 6

-continued
Compound No. 7
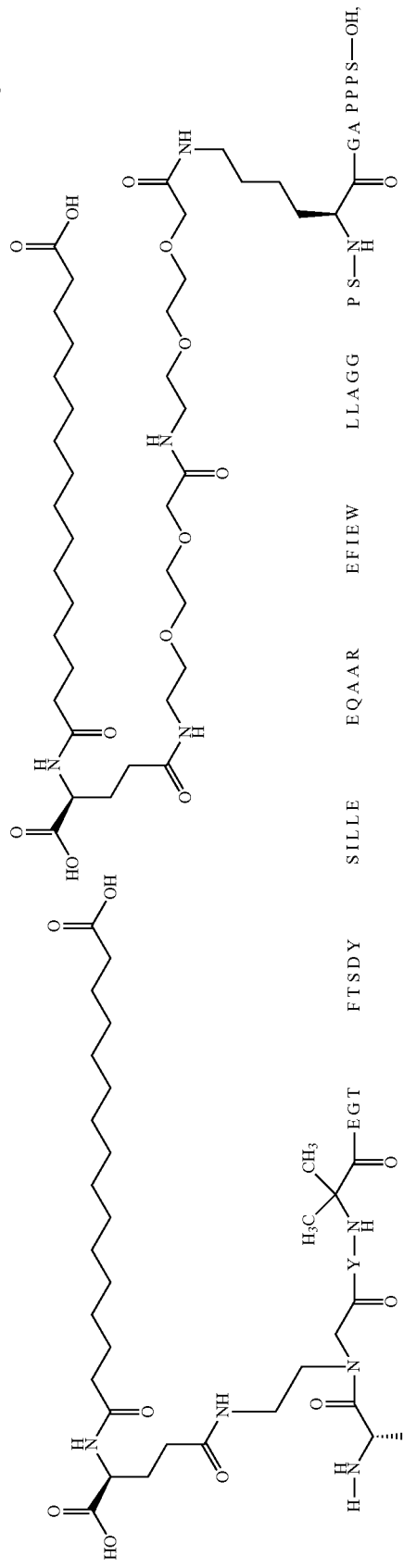
Compound No. 8
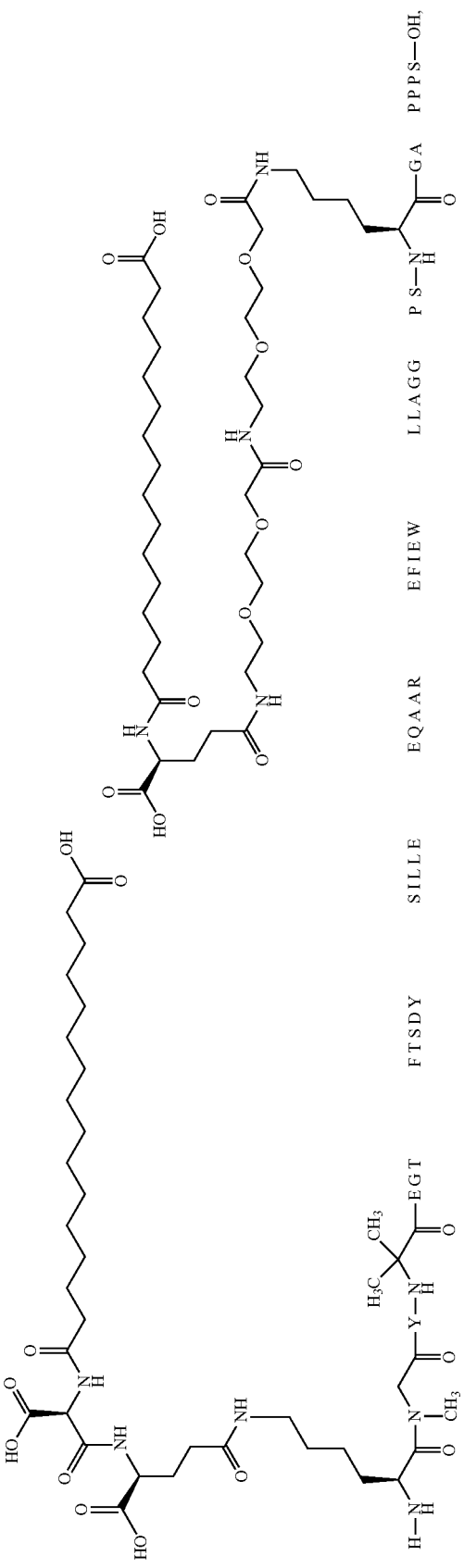

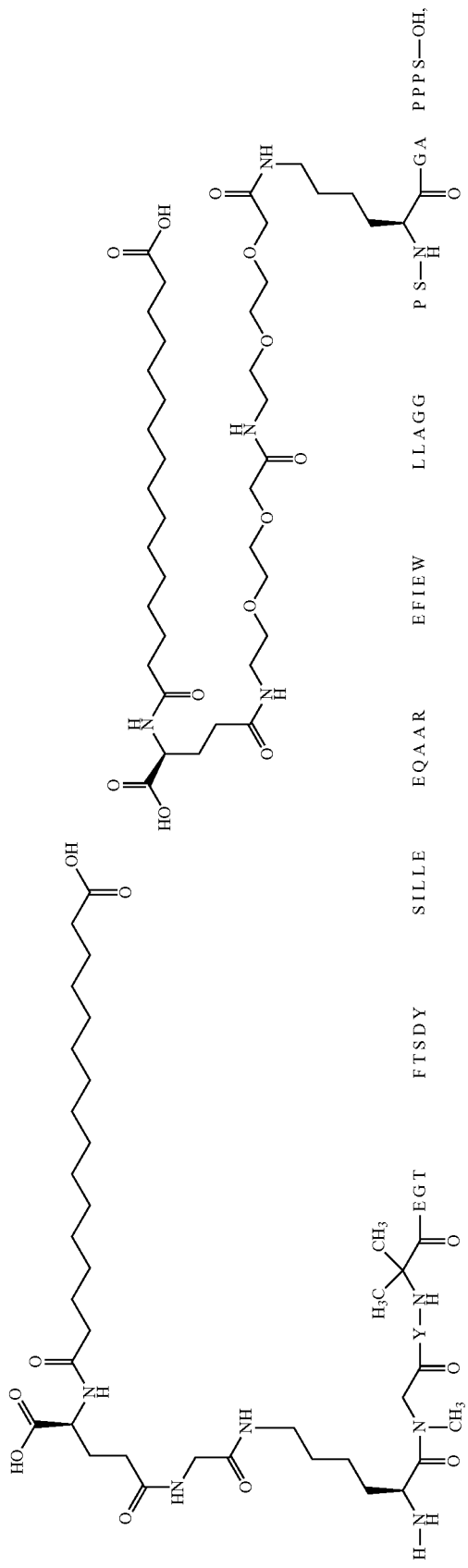
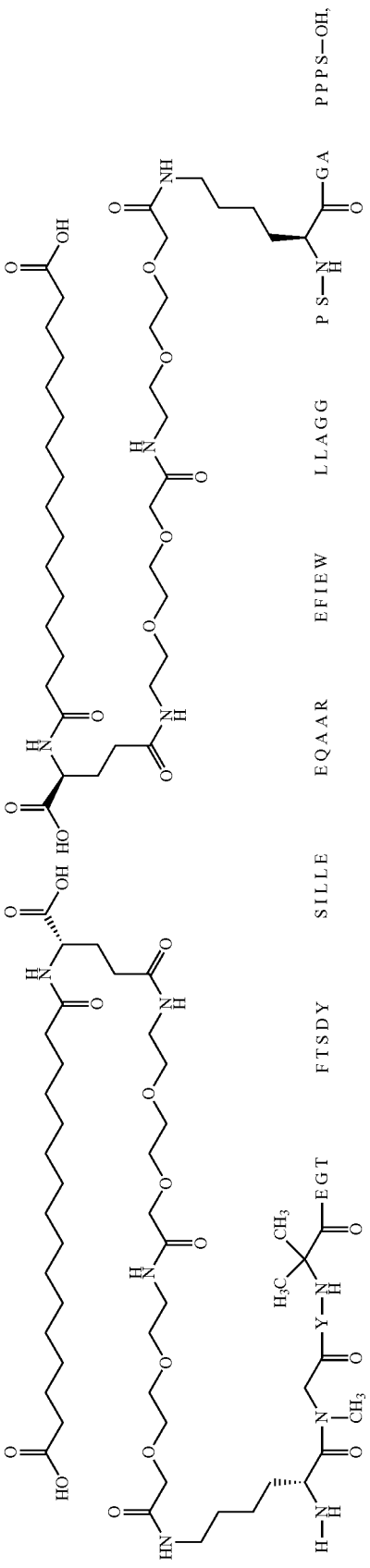

Compound No. 11
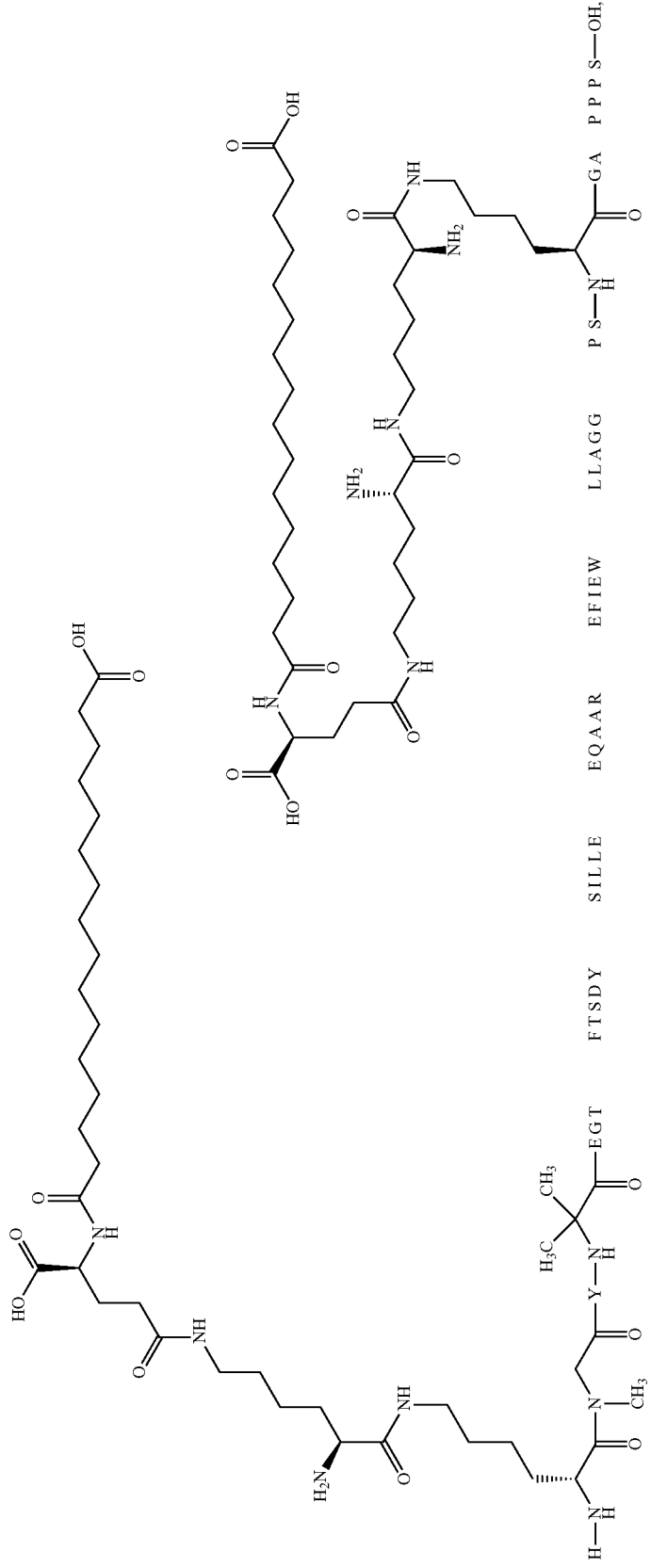

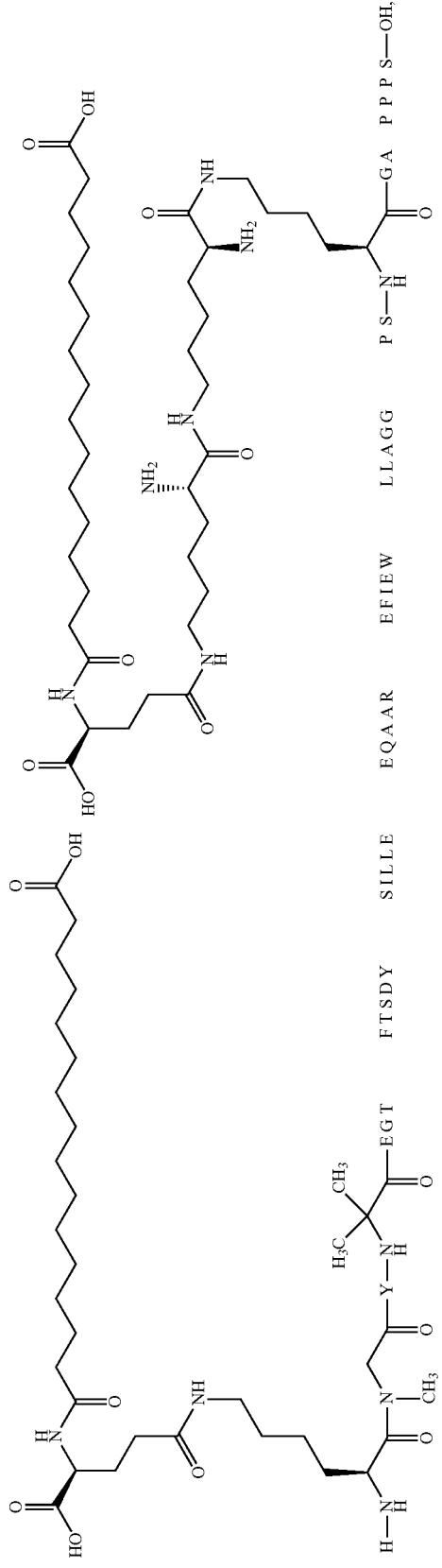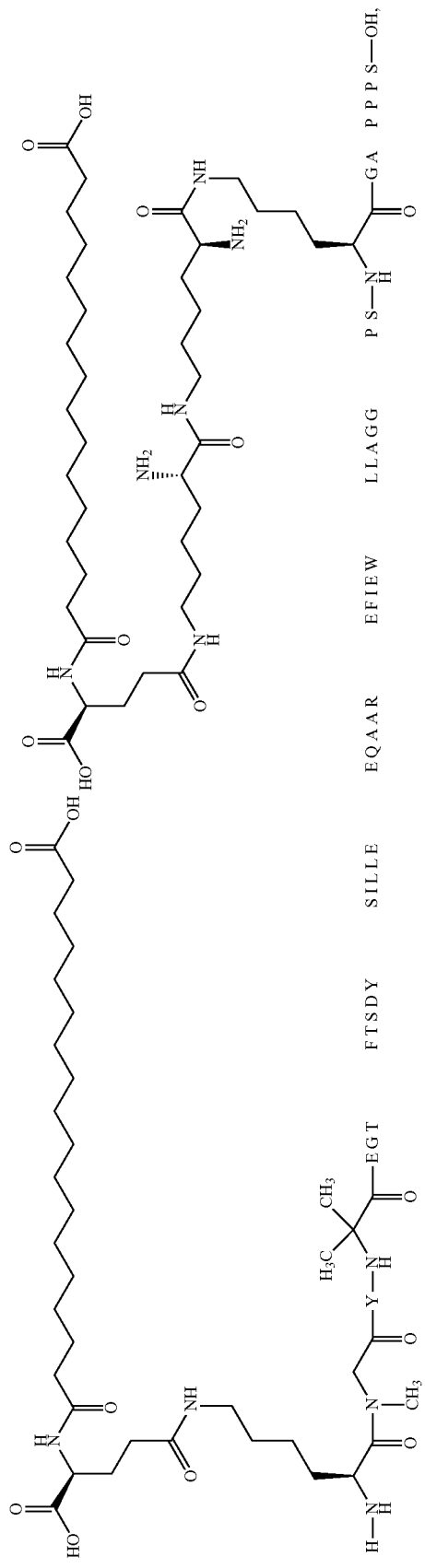

Compound No. 14
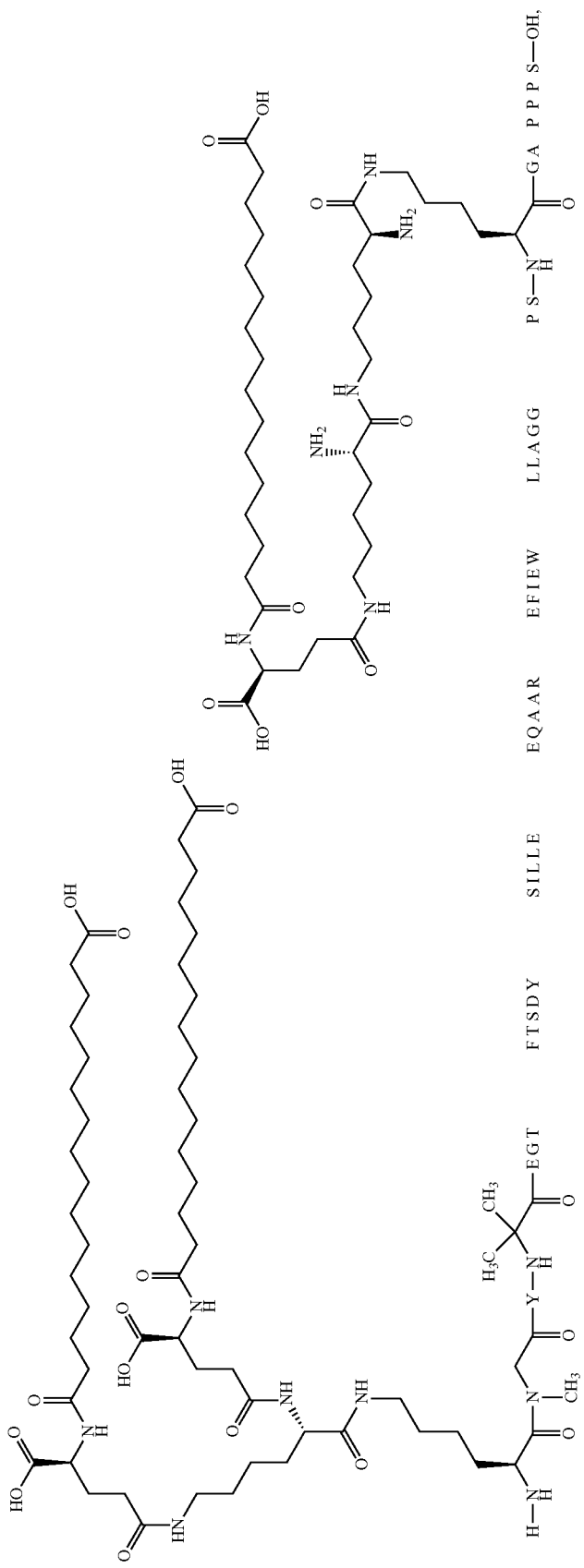

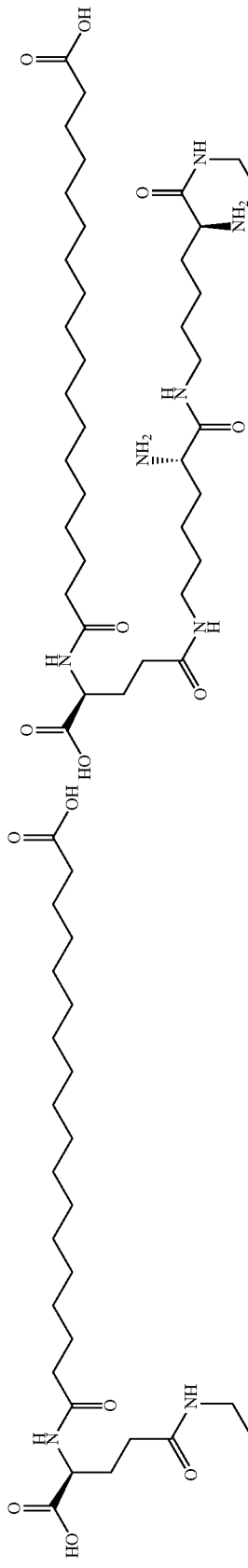
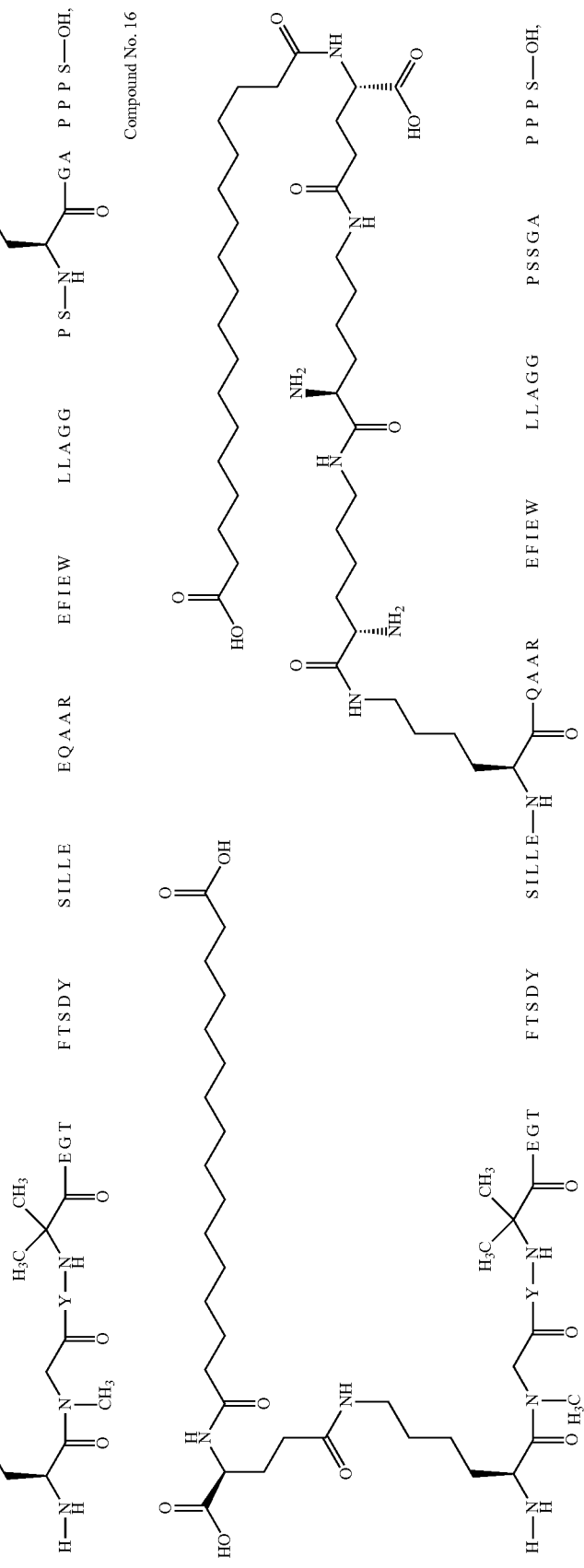

Compound No. 17
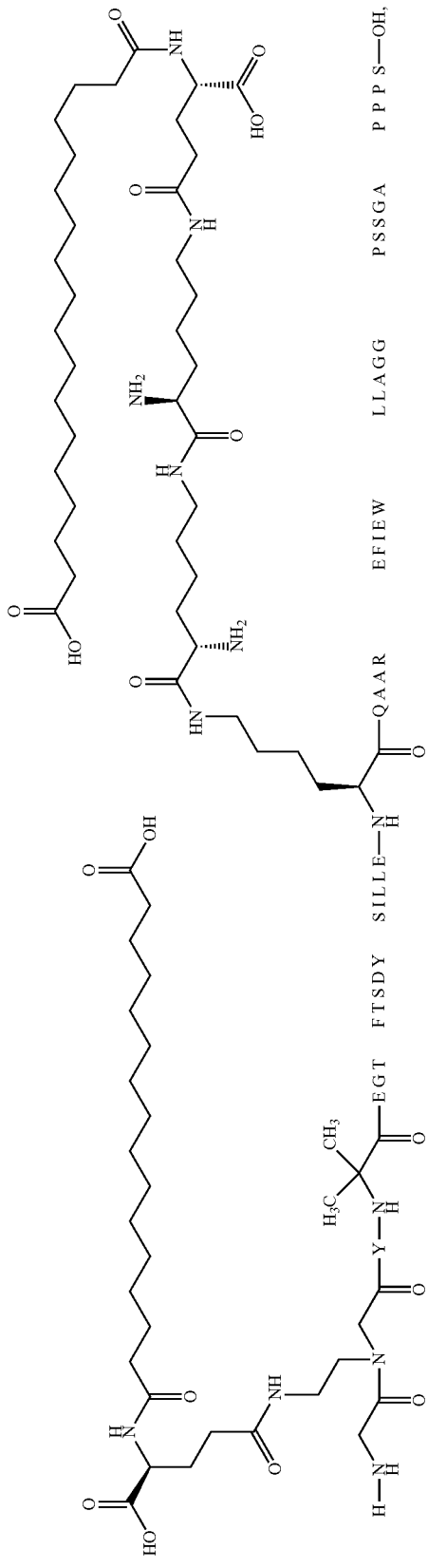
Compound No. 18
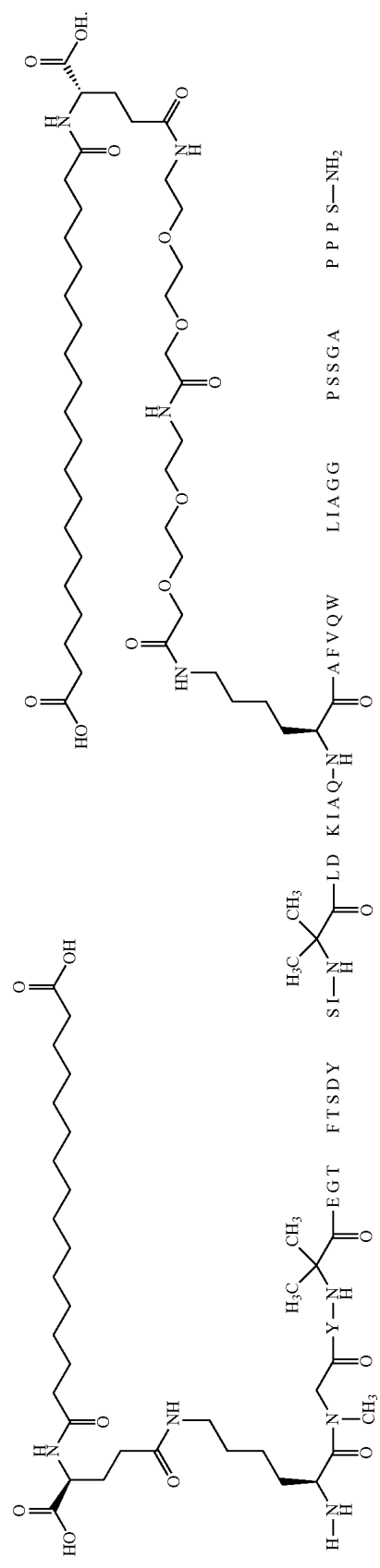

43. The compound according to any one of embodiments 1 to 42, or a pharmaceutically acceptable salt, ester or amide thereof, wherein the compound is selected from the group consisting of compound no. 1, 2, 3, 9, and 10.
44. The compound according to any one of embodiments 1 to 43, or a pharmaceutically acceptable salt, ester or amide thereof, wherein the compound is compound no. 1.
45. The compound according to any one of embodiments 1 to 43, or a pharmaceutically acceptable salt, ester or amide thereof, wherein the compound is compound no. 2.
46. The compound according to any one of embodiments 1 to 43, or a pharmaceutically acceptable salt, ester or amide thereof, wherein the compound is compound no. 3.
47. The compound according to any one of embodiments 1 to 43, or a pharmaceutically acceptable salt, ester or amide thereof, wherein the compound is compound no. 4.
48. The compound according to any one of embodiments 1 to 43, or a pharmaceutically acceptable salt, ester or amide thereof, wherein the compound is compound no. 5.
49. The compound according to any one of embodiments 1 to 48, or a pharmaceutically acceptable salt, ester or amide thereof, wherein the compound is a prodrug and does not exert any significant potency in vitro.
50. The compound according to any one of embodiments 1 to 49, or a pharmaceutically acceptable salt, ester or amide thereof, wherein the compound is a prodrug and has a conversion half-life.
51. The compound according to embodiment 50, or a pharmaceutically acceptable salt, ester or amide thereof, wherein the conversion half-life is measured in vitro at pH 7.4 at 37° C.
52. The compound according to embodiments 50 or 51, or a pharmaceutically acceptable salt, ester or amide thereof, wherein the conversion half-life is measured as described herein in General Methods for Measuring Conversion Half-life.
53. The compound according to any one of embodiments 50 to 52 or a pharmaceutically acceptable salt, ester or amide thereof, wherein the conversion half-life is suitable for once daily administration.
54. The compound according to any one of embodiments 50 to 52 or a pharmaceutically acceptable salt, ester or amide thereof, wherein the conversion half-life is suitable for weekly daily administration.
55. The compound according to any one of embodiments 50 to 52 or a pharmaceutically acceptable salt, ester or amide thereof, wherein the conversion half-life measured in vitro is 90-4300 hours.
56. The compound according to any one of embodiments 50 to 52 or a pharmaceutically acceptable salt, ester or amide thereof, wherein the conversion half-life measured in vitro is 90-4300 hours.
57. The compound according to any one of embodiments 50 to 52 or a pharmaceutically acceptable salt, ester or amide thereof, wherein the conversion half-life measured in vitro is 300-1100 hours.
58. The compound according to any one of embodiments 50 to 52 or a pharmaceutically acceptable salt, ester or amide thereof, wherein the conversion half-life measured in vitro is 450-650 hours.
59. The compound according to any one of embodiments 50 to 52 or a pharmaceutically acceptable salt, ester or amide thereof, wherein the conversion half-life measured in vitro is at least 100 hours.
60. The compound according to any one of embodiments 50 to 52 or a pharmaceutically acceptable salt, ester or amide thereof, wherein the conversion half-life measured in vitro is at least 200 hours.
61. The compound according to any one of embodiments 50 to 52 or a pharmaceutically acceptable salt, ester or amide thereof, wherein the conversion half-life measured in vitro is at least 300 hours.
62. The compound according to any one of embodiments 1 to 61, or a pharmaceutically acceptable salt, ester or amide thereof, wherein the compound has a terminal half-life.
63. The compound according to any one of embodiments 1 to 61, or a pharmaceutically acceptable salt, ester or amide thereof, wherein the compound has a terminal half-life and the terminal half-life is suitable for once daily administration.
64. The compound according to any one of embodiments 1 to 61, or a pharmaceutically acceptable salt, ester or amide thereof, wherein the compound has a terminal half-life and the terminal half-life is suitable for once weekly administration.
65. The compound according to any one of embodiments 62 to 64, or a pharmaceutically acceptable salt, ester or amide thereof, wherein the terminal half-life is determined in minipigs and measured as described herein in General Methods for Measuring Terminal Half-Life in Minipigs.
66. The compound according to any one of embodiments 62 to 65, or a pharmaceutically acceptable salt, ester or amide thereof, wherein the terminal half-life is >90 hours when determined in minipigs.
67. The compound according to any one of embodiments 62 to 65, or a pharmaceutically acceptable salt, ester or amide thereof, wherein the terminal half-life is >110 hours when determined in minipigs.
68. The compound according to any one of embodiments 62 to 65, or a pharmaceutically acceptable salt, ester or amide thereof, wherein the terminal half-life is >250 hours when determined in minipigs.
69. The compound according to any one of embodiments 62 to 65, or a pharmaceutically acceptable salt, ester or amide thereof, wherein the terminal half-life is >180 hours when determined in minipigs.
70. The compound according to any one of embodiments 62 to 65, or a pharmaceutically acceptable salt, ester or amide thereof, wherein the terminal half-life is 80-240 hours when determined in minipigs.
71. The compound according to any one of embodiments 62 to 65, or a pharmaceutically acceptable salt, ester or amide thereof, wherein the terminal half-life is 110-191 hours when determined in minipigs.
72. A pharmaceutical composition comprising a compound according to any one of embodiments 1 to 71 and at least one pharmaceutically acceptable excipient.
73. The pharmaceutical composition according to embodiment 72, wherein the pharmaceutical composition is a liquid formulation.
74. The pharmaceutical composition according to embodiment 72, wherein the pharmaceutical composition is a solid formulation.
75. The pharmaceutical composition according to embodiment 72, wherein the pharmaceutical composition is for oral administration.

76. The pharmaceutical composition according to any one of embodiments 74 to 76, wherein the composition if in form of a tablet.
77. The pharmaceutical composition according to any one of embodiments 74 to 77, wherein at least one pharmaceutical acceptable excipient is a salt of N-(8-(2-hydroxybenzoyl)amino)caprylic acid such as N-(8-(2 hydroxybenzoyl)amino)caprylic acid is sodium N-(8-(2-hydroxybenzoyl)amino)caprylate (SNAC).
78. The pharmaceutical composition according to any one of embodiments 74 to 78, further comprising a lubricant such as magnesium stearate.
79. A tablet comprising a compound according to any one of embodiments 1-71, a salt of N-(8-(2-hydroxybenzoyl)amino)caprylic acid, a lubricant, and optionally one or more pharmaceutically acceptable excipients.
80. The tablet according to embodiment 79, wherein the salt of N-(8-(2 hydroxybenzoyl)amino)caprylic acid is sodium N-(8-(2-hydroxybenzoyl)amino)caprylate (SNAC).
81. The tablet according to embodiment 79 or embodiment 80, wherein the lubricant is magnesium stearate.
82. A compound according to any one of embodiments 1 to 71 or a pharmaceutical composition according to any one of embodiments 72 to 78 or a tablet according to any one of embodiments 79 to 81 for use as a medicament.
83. A compound according to any one of embodiments 1 to 71 or a pharmaceutical composition according to any one of embodiments 72 to 78 or a tablet according to any one of embodiments 79 to 81 for use in the treatment of type 2 diabetes.
84. A compound according to any one of embodiments 1 to 71 or a pharmaceutical composition according to any one of embodiments 72 to 78 or a tablet according to any one of embodiments 79 to 81 for use in the treatment of obesity.
85. A compound according to any one of embodiments 1 to 71 or a pharmaceutical composition according to any one of embodiments 72 to 78 or a tablet according to any one of embodiments 79 to 81 for use in the treatment of liver diseases. such as hepatic steatosis, non-alcoholic fatty liver disease (NAFLD), non-alcoholic steatohepatitis (NASH), liver inflammation, and/or fatty liver.
86. Use of a compound according to any one of embodiments 1 to 71 or a pharmaceutical composition according to any one of embodiments 72 to 78 or a tablet according to any one of embodiments 79 to 81 in the manufacture of a medicament for
  a. prevention and/or treatment of liver diseases. such as hepatic steatosis, non-alcoholic fatty liver disease (NAFLD), non-alcoholic steatohepatitis (NASH), liver inflammation, and/or fatty liver;
  b. prevention and/or treatment of obesity; and/or
  c. prevention and/or treatment of type 2 diabetes.
87. Use of a compound according to any one of embodiments 1 to 71 or a pharmaceutical composition according to any one of embodiments 72 to 78 or a tablet according to any one of embodiments 79 to 81 in the manufacture of a medicament for the treatment of type 2 diabetes.
88. Use of a compound according to any one of embodiments 1 to 71 or a pharmaceutical composition according to any one of embodiments 72 to 78 or a tablet according to any one of embodiments 79 to 81 in the manufacture of a medicament for obesity.
89. A method for prevention and/or treatment of type 2 diabetes administering a compound according to any one of embodiments 1 to 71 or a pharmaceutical composition according to any one of embodiments 72 to 78 or a tablet according to any one of embodiments 79 to 81, to a subject in need thereof.
90. A method for prevention and/or treatment of obesity administering a compound according to any one of embodiments 1 to 71 or a pharmaceutical composition according to any one of embodiments 72 to 78 or a tablet according to any one of embodiments 79 to 81, to a subject in need thereof.
91. A method for prevention and/or treatment of liver diseases. such as hepatic steatosis, non-alcoholic fatty liver disease (NAFLD), non-alcoholic steatohepatitis (NASH), liver inflammation, and/or fatty liver administering a compound according to any one of embodiments 1 to 71 or a pharmaceutical composition according to any one of embodiments 72 to 78 or a tablet according to any one of embodiments 79 to 81, to a subject in need thereof.

The invention is further described by the following further non-limiting embodiments:

1. A compound of Formula I:

$$B-Z \qquad \text{(Formula I)}$$

or a pharmaceutical acceptable salt, ester or amide thereof, wherein Z is a GLP-1/GIP receptor co-agonist or derivative thereof;
wherein B is a dipeptide of formula II:

$$X-Y \qquad \text{(Formula II)},$$

wherein X is any alpha-amino acid linked to Y via an amide bond formed between the alpha-carboxylic acid group of X and the alpha-amino group of Y,
  wherein Y is an N-alkylated alpha-amino acid linked to Z via an amide bond formed between the alpha-carboxylic acid group of Y and an amine of Z.
2. The compound according to any one of the preceding embodiments, or a pharmaceutically acceptable salt, ester or amide thereof, wherein Y is selected from the group consisting of sarcosine, N-sec-butylglycine, proline, trans-4-hydroxyproline, N-methylglutamate, N-methylnorleucine, N-methylhomoalanine, N-methylalanine, N-methyllysine, N-(2-aminoethyl)glycine, N-hexylhomoalanine, N-propylalanine, homoproline, N-propylglycine, N-ethylglycine, and N-methylphenylalanine.
3. The compound according to any one of the preceding embodiments, or a pharmaceutically acceptable salt, ester or amide thereof, wherein X is selected from the group consisting of lysine, 4-aminophenylalanine, D-lysine, alanine, glycine, proline, D-valine, homoproline, D-proline, D-homoproline, D-alanine, and azetidine-2-carboxylic acid.
4. The compound according to any one of the preceding embodiments, or a pharmaceutically acceptable salt, ester or amide thereof, wherein Y is selected from the group consisting of sarcosine, N-sec-butylglycine, proline, trans-4-hydroxyproline, N-methylglutamate, N-methylnorleucine, N-methylhomoalanine, N-methylalanine, N-methyllysine, N-hexylhomoalanine, N-propylalanine, homoproline, N-propylglycine, N-ethylglycine, and N-methylphenylalanine.

5. The compound according to any one of the preceding embodiments, or a pharmaceutically acceptable salt, ester or amide thereof, wherein Y is sarcosine or N-(2-aminoethyl)glycine.
6. The compound according to any one of the preceding embodiments, or a pharmaceutically acceptable salt, ester or amide thereof, wherein X is selected from the group consisting of lysine, D-lysine, alanine, leucine, glycine, proline, and aspartic acid.
7. The compound according to any one of the preceding embodiments, or a pharmaceutically acceptable salt, ester or amide thereof, wherein X is selected from the group consisting of lysine, D-lysine, and glycine.
8. The compound according to any one of the preceding embodiments, or a pharmaceutically acceptable salt, ester or amide thereof, wherein dipeptide is capable of undergoing an intramolecular cyclisation to form a 2,5-diketopiperazine (DKP) such that the amide bond between B and Z is cleaved.
9. The compound according to any one of the preceding embodiments, or a pharmaceutically acceptable salt, ester or amide thereof, wherein the dipeptide comprises a substituent b.
10. The compound according to any one of the preceding embodiments, or a pharmaceutically acceptable salt, ester or amide thereof, wherein the dipeptide has a substituent b.
11. The compound according to any one of the preceding embodiments, or a pharmaceutically acceptable salt, ester or amide thereof, wherein a substituent b is covalently attached to X optionally via an amide bond.
12. The compound according to any one of the preceding embodiments, or a pharmaceutically acceptable salt, ester or amide thereof, wherein the substituent b comprises or consists of a protractor and optionally a linker.
13. The compound according to any one of the preceding embodiments, or a pharmaceutically acceptable salt, ester or amide thereof, wherein the protractor is Chem. 1.
14. The compound according to any one of the preceding embodiments, or a pharmaceutically acceptable salt, ester or amide thereof, wherein the substituent b is selected from the group consisting of Chem. 16, Chem. 17, Chem. 18, Chem. 19, Chem. 20, Chem. 21, and Chem. 22.
15. The compound according to any one of the preceding embodiments, or a pharmaceutically acceptable salt, ester or amide thereof, wherein the amino acid sequence of the GLP-1/GIP receptor co-agonist is YX$_2$EGTX$_6$TSDYSX$_{12}$X$_{13}$LX$_{15}$X$_{16}$X$_{17}$AX$_{19}$X$_{20}$X$_{21}$FX$_{23}$X$_{24}$WLX$_{27}$X$_{28}$GX$_3$X$_{31}$X$_{32}$X$_{33}$X$_{34}$X$_{35}$X$_{36}$X$_{37}$X$_{38}$X$_{39}$ (SEQ ID NO.: 1), wherein
X$_2$ is Aib or A
X$_6$ is F or V
X$_{12}$ is I or Y
X$_{13}$ is Y, A, L, I or Aib
X$_{15}$ is D or E
X$_{16}$ is K or E
X$_{17}$ is Q or I
X$_{19}$ is A or Q
X$_{20}$ is Q, R, E, H, or K
X$_{21}$ is A or E
X$_{23}$ is I or V
X$_{24}$ is E, Q or N
X$_{27}$ is L or I
X$_{28}$ is A or R
X$_{30}$ is G or absent
X$_{31}$ is P or absent
X$_{32}$ is E, S or absent
X$_{33}$ is S, K or absent
X$_{34}$ is G or absent
X$_{35}$ is A or absent
X$_{36}$ is P or absent
X$_{37}$ is P or absent
X$_{38}$ is P or absent
X$_{39}$ is S or absent.
16. The compound according to any one of the preceding embodiments, or a pharmaceutically acceptable salt, ester or amide thereof, wherein the amino acid sequence of the GLP-1/GIP receptor co-agonist is Y-Aib-EGTFTSDYSIX$_{13}$LX$_{15}$X$_{16}$X$_{17}$AX$_{19}$X$_{20}$X$_{21}$FX$_{23}$X$_{24}$WLX$_{27}$AGGPSX$_{33}$GAPPPS (SEQ ID NO.: 2), wherein
X$_{13}$ is L or Aib,
X$_{15}$ is D or E,
X$_{16}$ is K or E,
X$_{17}$ is Q or I,
X$_{19}$ is A or Q,
X$_{20}$ is R or K
X$_{21}$ is A or E
X$_{23}$ is I or V
X$_{24}$ is E or Q
X$_{27}$ is L or I;
X$_{33}$ is S or K.
17. The compound according to any one of the preceding embodiments, or a pharmaceutically acceptable salt, ester or amide thereof, the amino acid sequence of the GLP-1/GIP receptor co-agonist is Y-Aib-EGTFTSDYSILLEX$_{16}$QAAREFIEWLLAGGPSX33GAPPPS (SEQ ID NO.: 3), wherein
X$_{16}$ is K or E,
X$_{33}$ is S or K.
18. The compound according to any one of the preceding embodiments, or a pharmaceutically acceptable salt, ester or amide thereof, wherein X$_{16}$ is E and X$_{33}$ is K.
19. The compound according to any one of the preceding embodiments, or a pharmaceutically acceptable salt, ester or amide thereof, wherein X$_{16}$ is K and X$_{33}$ is S.
20. The compound according to any one of the preceding embodiments, or a pharmaceutically acceptable salt, ester or amide thereof, wherein the amino acid sequence of the GLP-1/GIP receptor co-agonist is selected from the group consisting of Y-Aib-EGTFTSDYSI-Aib-LDKIAQKAFVQWLIAGGPSS GAPPPS (SEQ ID NO.: 4), Y-Aib-EGTFTSDYSILLE-EQAAREFIEWLLAGGPSKGAPPPS (SEQ ID NO.: 5), and Y-Aib-EGTFTSDYSILLEKQAAREFIEWL-LAGGPSSGAPPPS (SEQ ID NO.: 6).
21. The compound according to any one of the preceding embodiments, or a pharmaceutically acceptable salt, ester or amide thereof, wherein the GLP-1/GIP receptor co-agonist comprises a substituent z, and wherein the substituent z is attached to the GLP-1/GIP receptor co-agonist via a lysine (K).
22. The compound according to any one of the preceding embodiments, or a pharmaceutically acceptable salt, ester or amide thereof, wherein the substituent z is attached to the GLP-1/GIP receptor co-agonist via a lysine (K) at position 16, 20 or 33.
23. The compound according to any one of the preceding embodiments, or a pharmaceutically acceptable salt, ester or amide thereof, wherein the compound is selected from the group consisting of compound no. 1, compound no. 2, compound no. 3, compound no. 4, compound no. 5, compound no. 6, compound no. 7, compound no. 8, compound no. 9, compound no. 10, compound no. 11, compound no. 12, compound no. 13, compound no. 14, compound no. 15, compound no. 16, compound no. 17, and compound no. 18.

24. The compound according to any one of the preceding embodiments, or a pharmaceutically acceptable salt, ester or amide thereof, wherein the compound is selected from the group consisting of compound no. 1, 2, 3, 9, and 10.

25. A pharmaceutical composition comprising a compound any one of the preceding embodiments and at least one pharmaceutically acceptable excipient.

26. The pharmaceutical composition according to any one of the preceding embodiments, wherein the pharmaceutical composition is a liquid formulation.

27. The pharmaceutical composition according to any one of the preceding embodiments, wherein the pharmaceutical composition is a solid formulation.

28. The pharmaceutical composition according to any one of the preceding embodiments, wherein the pharmaceutical composition is for oral administration.

29. The pharmaceutical composition according to any one of the preceding embodiments, wherein the pharmaceutical composition is for parenteral administration.

30. The pharmaceutical composition according to any one of the preceding embodiments, wherein the pharmaceutical composition is in form of a tablet.

31. A compound according to any one of the preceding embodiments for use as a medicament.

32. A compound according to any one of the preceding embodiments for use in the prevention and/or treatment of type 2 diabetes.

33. A compound according to any one of the preceding embodiments for use in the prevention and/or treatment of obesity.

34. A compound according to any one of the preceding embodiments for use in the prevention and/or treatment of liver diseases. such as hepatic steatosis, non-alcoholic fatty liver disease (NAFLD), non-alcoholic steatohepatitis (NASH), liver inflammation, and/or fatty liver.

EXAMPLES

This experimental part starts with a list of abbreviations and is followed by a section on the general methods for compound preparation and a section on the methods for measuring properties relevant for the exposure profile. A number of specific examples have been included in each of the sections to illustrate the invention. All example compounds were prepared according to the general methods described herein. Where appropriate, chemical names of substituents were generated using Accelrys Draw version 4.1 SP1 software and IUPAC nomenclature.

Abbreviations

The following abbreviations are used in the following, in alphabetical order:
Ado: 8-amino-3,6-dioxaoctanoic acid
Aeg: N-(2-aminoethyl)glycine
Aib: α-aminoisobutyric acid
Alloc: allyloxycarbonxyl
API: atmospheric pressure ionization
AUC: area under the curve
BHK: baby hamster kidney
Boc: t-butyloxycarbonyl
Cl-HOBt: 6-chloro-1-hydroxybenzotriazole
DCM: dichloromethane
DIC: diisopropylcarbodiimide
DIPEA: N,N-diisopropylethylamine
DKP: 2,5-diketopiperazine
DMEM: Dulbecco's Modified Eagle's Medium
DPBS: Dulbecco's phosphate buffered saline
EDTA: ethylenediaminetetraacetic acid
ELISA: enzyme linked immunosorbent assay
equiv: molar equivalent
FBS: fetal bovine serum
Fmoc: 9-fluorenylmethyloxycarbonyl
GIP: glucose-dependent insulinotropic polypeptide
GIPR: glucose-dependent insulinotropic polypeptide receptor
GLP-1: glucagon-like peptide 1
GLP-1R: glucagon-like peptide 1 receptor
h: hours
HEPES: 4-(2-hydroxyethyl)-1-piperazineethanesulfonic acid
HFIP: 1,1,1,3,3,3-hexafluoro-2-propanol or hexafluoroisopropanol
HPLC: high performance liquid chromatography
HSA: human serum albumin
i.v. intravenously
LCMS: liquid chromatography mass spectroscopy
MeCN: acetonitrile
MeOH: methanol
mM: millimolar
mmol: millimoles
min: minutes
Mtt: 4-methyltrityl
NMP: 1-methyl-pyrrolidin-2-one
OtBu: tert-butyl ester
Oxyma Pure®: cyano-hydroxyimino-acetic acid ethyl ester
Pbf: 2,2,4,6,7-pentamethyldihydrobenzofuran-5-sulfonyl
PBS: phosphate buffered saline
PK: pharmacokinetic
pM: picomolar
p.o.: oral
rpm: rounds per minute
Rt: retention time
Sar: sarcosine
s.c.: subcutaneous
SNAC: sodium N-[8-(2-hydroxybenzoyl)amino]caprylate
SPPS: solid phase peptide synthesis
tBu: tert-butyl
T2D: type 2 diabetes mellitus
TFA: trifluoroacetic acid
TIS: triisopropylsilane
Trt: triphenylmethyl or trityl
UPLC: ultra-performance liquid chromatography General Methods for Preparation of the Compounds of the Invention Methods for solid phase peptide synthesis (SPPS methods, including methods for de-protection of amino acids, methods for cleaving the peptide from the resin, and for its purification), as well as methods for detecting and characterising the resulting peptide (LCMS methods) are described here below.

Resins employed for the preparation of C-terminal peptide amides were H-Rink Amide-ChemMatrix resin (loading e.g. 0.5 mmol/g). Resins employed for the preparation of C-terminal peptide acids were Wang-polystyrene resin preloaded with the suitably protected C-terminal amino acid derivative (loading e.g. 0.5 mmol/g). All operations stated below were performed within a 0.1-1.0 mmol synthesis scale range. The Fmoc-protected amino acid derivatives used, unless specifically stated otherwise, were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Fmoc-Lys(Mtt)-OH, Fmoc-Aib-OH, etc. supplied from e.g. AAPPTEC, Anaspec, Bachem, ChemImpex, Iris Biotech, Midwest Biotech, Gyros Protein Technologies or Novabiochem.

Where nothing else is specified, the proteinogenic L-form of the amino acids are used. For coupling of the N-terminal amino acid of each compound, a reagent was used bearing Boc protected at the alpha-amino group.

In case of dipeptide attachment using SPPS, the following suitably protected building blocks such as but not limited to Alloc-Aeg(Fmoc)-OH, Boc-Ala-OH, Boc-Asp(OtBu)-OH, Boc-Gly-OH, Boc-Leu-OH, Boc-Lys(Fmoc)-OH, Boc-D-Lys(Fmoc)-OH, Boc-Pro-OH, Fmoc-Aeg(N)—OH, and Fmoc-Sar-OH were used. In case of substituent attachment using SPPS, the following suitably protected building blocks such as but not limited to Fmoc-8-amino-3,6-dioxaoctanoic acid (Fmoc-Ado-OH), Boc-Lys(Fmoc)-OH, Fmoc-Glu-OtBu, Fmoc-Gly-OH, hexadecanedioic acid mono-tert-butyl ester, octadecanedioic acid mono-tert-butyl ester, or eicosanedioic acid mono-tert-butyl ester were used.

1. Synthesis of Resin-Bound Protected Peptide Backbone:
Method: SPPS_A

SPPS was performed using Fmoc based chemistry on a Protein Technologies SymphonyX solid-phase peptide synthesizer, using the manufacturer supplied protocols with minor modifications. Mixing was accomplished by occasional bubbling with nitrogen. The step-wise assembly was performed using the following steps: 1) pre-swelling of resin in DMF; 2) Fmoc-deprotection by the use of 20% (v/v) piperidine in DMF with or without 1% (v/v) TFA for two treatments of 10 min each; 3) washes with DMF to remove piperidine; 4) coupling of Fmoc-amino acid by the addition of 3-12 equiv each of Fmoc-amino acid, Oxyma Pure®, and DIC as a solution in DMF with or without 2,4,6-collidine, then mixing for at least 30 min; 4) washes with DMF to remove excess reagents; 5) final washes with DCM at the completion of the assembly. Some amino acids such as, but not limited to, those following a sterically hindered amino acid (e.g. Aib) were coupled with an extended reaction time (e.g. 4 h or overnight) to ensure reaction completion.
Method: SPPS_B SPPS was performed using Fmoc based chemistry on an Applied Biosystems 431A solid-phase peptide synthesizer, using the manufacturer supplied general Fmoc protocols. Mixing was accomplished by vortexing and occasional bubbling with nitrogen. The step-wise assembly was done using the following steps: 1) activation of Fmoc-amino acid by dissolution of 10 equiv each of solid Fmoc-acid acid in a 1 M solution of Cl-HOBt in NMP, then addition of 10 equiv of DIC as a 1 M solution in NMP, then mixing simultaneously to steps 2-3; 2) Fmoc-deprotection by the use of 20% (v/v) piperidine in NMP for one treatment of 3 min then a second treatment of 15 min; 3) washes with NMP to remove piperidine; 4) addition of activated Fmoc-amino acid solution to resin, then mixing for at least 45 min; 4) washes with NMP to remove excess reagents; 5) final washes with DCM at the completion of the assembly. Some amino acids such as, but not limited to, those following a sterically hindered amino acid (e.g. Aib) were coupled with an extended reach time (eg 4 h) and/or repeatedly treated with fresh coupling reagents to ensure reaction completion.

2. Attachment of Dipeptide and Substituents to Resin-Bound Protected Peptide Backbone
Method: DS_A For compounds containing a substituent-carrying N-terminal Lys or D-Lys, SPPS was continued using the same protocols as in SPPS_A to attach the amino acids of dipeptide B and the elements of substituent b.
Method: DS_B For compounds containing a substituent-carrying Aeg within dipeptide B, SPPS was continued using the same protocols as in SPPS_A to attach Fmoc-Aeg($N_3$)—OH and the Na-Boc-protected N-terminal amino acid. The azido protecting group was reduced to the amine by treating the resin-bound peptide with 5-10 equiv of tris(2-carboxyethyl)phosphine as a solution in 9:1 DMF/water for 2-3 h. The resin was drained and washed with 9:1 DMF/water and DMF, followed by attachment of the elements of substituent b using the same protocols as in SPPS_A.
Method: DS_C As an alternative to DS_B for compounds containing substituent-carrying Aeg within dipeptide B, SPPS was continued using the same protocols as in SPPS_A to attach Alloc-Aeg(Fmoc)-OH and the elements of substituent b. The Alloc protecting group was removed by treating the resin-bound peptide with 10 equiv of borane dimethylamine complex and 20 equiv of morpholine as a solution in DMF for 5 min under an argon atmosphere, then adding 0.1 equiv of palladium-tetrakis(triphenylphosphine) as a solution in DMF and treating for an additional 30 min. The resin was drained and washed with DCM, DMF, MeOH, water, and DMF. The Na-Boc-protected N-terminal amino acid was then attached using the same protocols as in SPPS_A.
Method: DS_D To attach substituent z, the NE-Mtt protection of the substituent-carrying Lys was removed by washing the resin with 30% HFIP in DCM for two treatments of 45 min each or 80% HFIP in DCM for treatments of 5 min, 5 min, 10 min, 10 min, 15 min, 20 min, and 30 min. The resin was drained and washed with DCM, DMF, 10% DIPEA/DCM, DCM, and DMF. SPPS was continued using the same protocols as in SPPS_A to attach the elements of substituent z.

3. Cleavage of Resin-Bound Peptide and Purification:
Method: CP_A

Following completion of the sidechain synthesis, the peptidyl resin was washed with DCM and dried, then treated with 95:2.5:2.5 (v/v/v) TFA/water/TIS or 92.5:5:2.5 (v/v/v) TFA/water/TIS for 2-3 h, followed by precipitation with diethyl ether. The precipitate was isolated (e.g. by filtration or centrifugation), washed with diethyl ether, dissolved in a suitable solvent (e.g. 2:1 water/MeCN), and let stand until all labile adducts decomposed. Purification was performed by reversed-phase preparative HPLC on a Phenomenex Luna C8(2) column (10 μm particle size, 100 Å pore size, 250×21.2 mm dimensions) or a Phenomenex Gemini-NX C18 column (5 μm particle size, 110 Å pore size, 250×50 mm dimensions). Separation of impurities and product elution was accomplished using an increasing gradient of MeCN in water containing 0.1% TFA. Relevant fractions were checked for identity and purity by analytical LCMS. Fractions containing the pure desired product were pooled and freeze-dried to afford the peptide TFA salt as a white solid.

4. Salt Exchange from TFA to Sodium Salt:
Method: SX_A

The freeze-dried peptide isolated from method CP_A was dissolved to 5-20 mg/mL in an appropriate aqueous buffer (e.g. 4:1 water/MeCN, 0.2 M sodium acetate) and adjusted to pH 7-8 with 1 M NaOH if necessary to achieve full solubility. The buffered solutions containing the peptide were salt-exchanged using a Sep-Pak C18 cartridge (0.5-2 g): The cartridge was first equilibrated with 4 column volumes of isopropanol, then 4 column volumes of MeCN, then 8 column volumes of water. The peptide solution was applied to the cartridge, and the flow through was reapplied to ensure complete retention of peptide. The cartridge was washed with 4 column volumes of water, then 10 column volumes of a buffer solution (e.g. pH 7.5) containing such as, but not limited to, $NaHCO_3$, NaOAc, or $Na_2HPO_4$. The column was washed with 4 column volumes of water, and the peptide was eluted with 5-10 column volumes of 50-80% MeCN in water. The peptide-containing eluent was freeze-dried to afford the peptide sodium salt as a white solid, which was used as such.

General Methods of Detection and Characterisation
LCMS Methods:
Method: LCMS_A

The analysis was performed on Agilent 1260 Infinity series HPLC/MS system by injecting an appropriate volume of sample onto a Phenomenex Kinetex C8 column (2.6 μm particle size, 100 Å pore size, 4.6×75 mm dimensions) equilibrated at 37 C. Eluent A was 0.05% TFA in water; eluent B was 0.05% TFA in 9:1 MeCN/water. Elution was achieved with a linear gradient of 20-100% eluent B over 10 min at a flow rate of 1.0 mL/min. UV detection was set to 214 nm. MS ionization was run in API-ES mode and positive polarity with a scan mass range of 500-2000 amu. The most abundant isotope of each m/z is reported.

Method: LCMS_B

The analysis was performed on a Waters ACQUITY UPLC/MS system by injecting an appropriate volume of sample onto a ACQUITY UPLC BEH130 column (1.7 μm particle size, 130 Å pore size, 2.1×150 mm dimensions) equilibrated at 40 C. Eluent A was 0.05% TFA in water; eluent B was 0.05% TFA in MeCN. Elution was achieved with a linear gradient of 5-95% eluent B over 16 min at a flow rate of 0.4 mL/min for UV detection and a linear gradient of 5-60% eluent B over 4 min at a flow rate of 0.45 mL/min for MS detection. UV detection was set to 214 nm. MS ionization was run in API-ES mode and positive polarity with a scan mass range of 100-2000 amu. The most abundant isotope of each m/z is reported.

Example 1: Synthesis of Compounds

The compounds are in the following described using single letter amino acid codes, except for Aeg, Aib, D-Lys, and Sar. Each substituent is included in brackets after the residue to which it is attached.

Parent Compound No. 1
Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

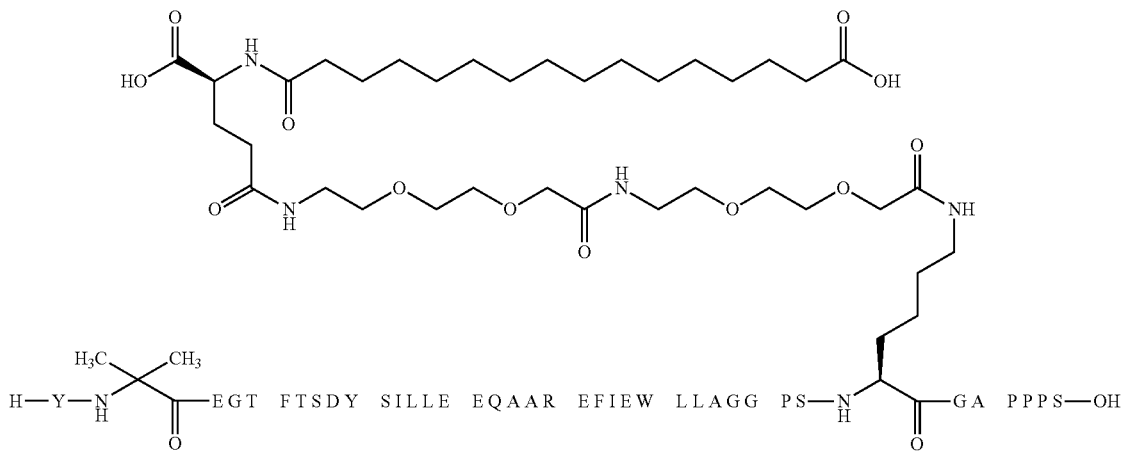

SEQ ID NO.: 5; substituent: Chem. 8 attached to Lys33
Synthesis methods: SPPS_A; DS_D; CP_A
Molecular weight (average) calculated: 4901.4 Da
LCMS_A: Rt=6.3 min; found $[M+3H]^{3+}$ 1634.6, $[M+4H]^{4+}$ 1226.1

Parent Compound No. 2
Y-Aib-EGTFTSDYSILLEEQAAREFIEWLLAGGPS-K
[(2S)-2-amino-6-[[(2S)-2-amino-6-[[(4S)-4-carboxy-4-(15-
carboxypentadecanoylamino)butanoyl]amino]hexanoyl]
amino]hexanoyl]-GAPPPS-OH

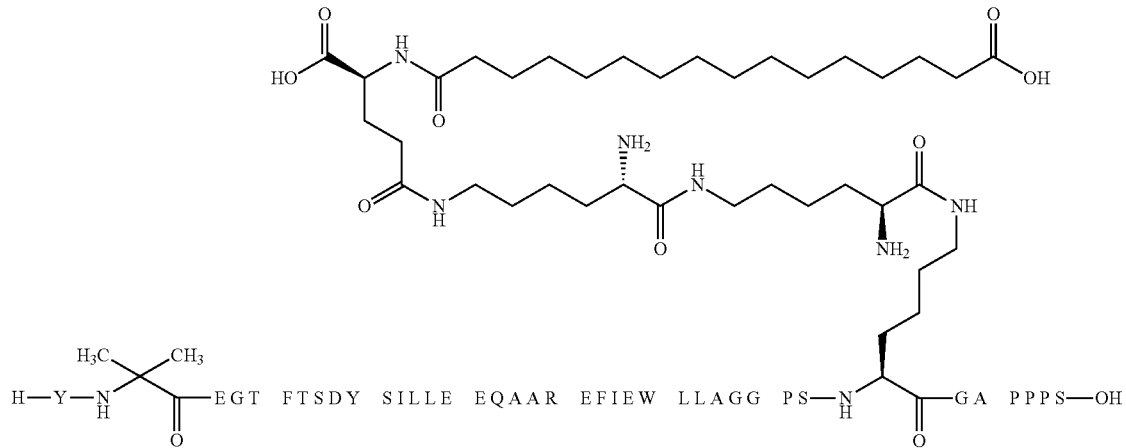

SEQ ID NO: 5; Substituent: Chem. 10 attached to Lys33
Synthesis methods: SPPS_A; DS_D; CP_A
Molecular weight (average) calculated: 4867.5 Da
LCMS_A: Rt=6.1 min; found $[M+3H]^{3+}$ 1623.1, $[M+4H]^{4+}$ 1217.6

Parent Compound No. 3
Y-Aib-EGTFTSDYSILLEEQAAREFIEWLLAGGPS-K
[(2S)-2-amino-6-[[(2S)-2-amino-6-[[(4S)-4-carboxy-4-(17-
carboxyheptadecanoylamino)butanoyl]amino]hexanoyl]
amino]hexanoyl]-GAPPPS-OH

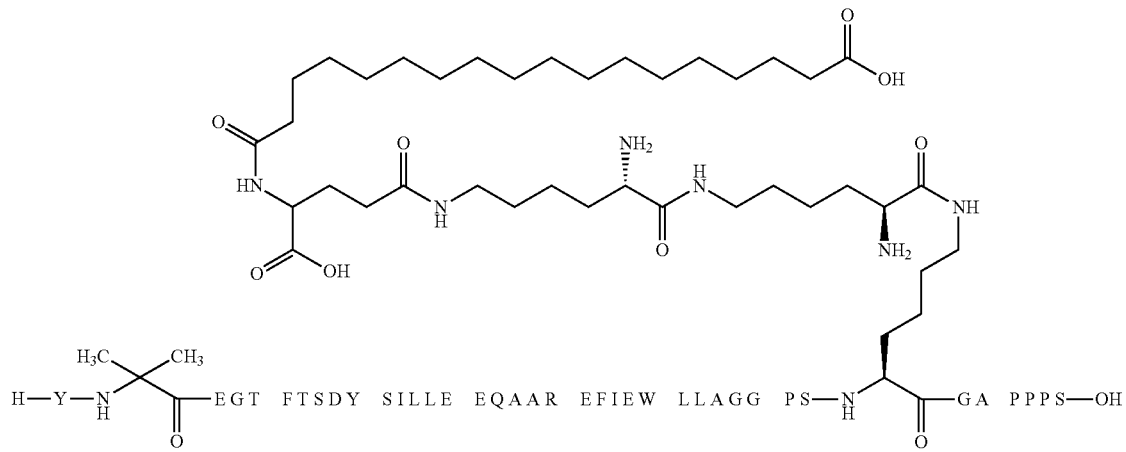

SEQ ID NO: 5; Substituent: Chem. 7 attached to Lys33
Synthesis methods: SPPS_A; DS_D; CP_A
Molecular weight (average) calculated: 4895.5 Da
LCMS_A: Rt=6.3 min; found $[M+3H]^{3+}$ 1632.4, $[M+4H]^{4+}$ 1224.6

Parent Compound No. 4
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLAGGPSSGAPPPS-OH

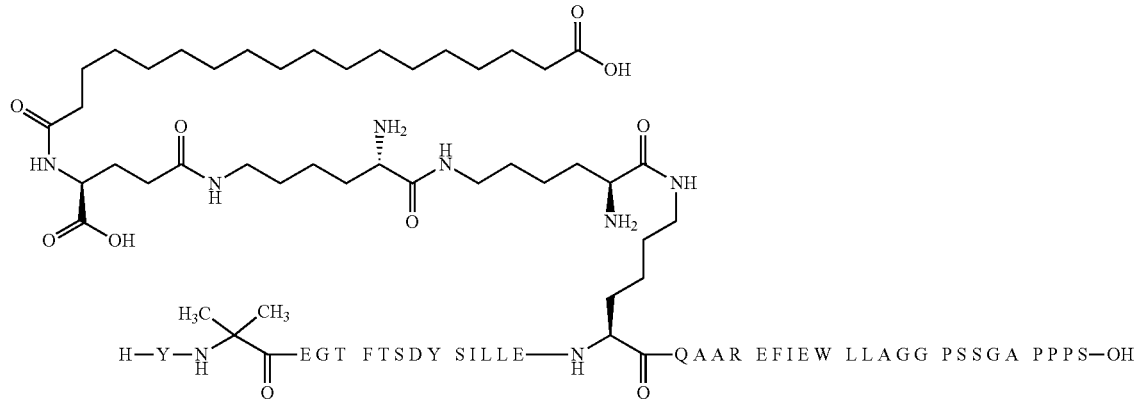

SEQ ID NO: 6; Substituent: Chem. 7 attached to Lys16
Synthesis methods: SPPS_A; DS_D; CP_A
Molecular weight (average) calculated: 4853.5 Da
LCMS_A: Rt=5.9 min; found $[M+3H]^{3+}$ 1618.5, $[M+4H]^{4+}$ 1214.2

Parent Compound No. 5
Y-Aib-EGTFTSDYSI-Aib-LDKIAQK[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-AFVQWLIAGGPSSGAPPPS-NH$_2$

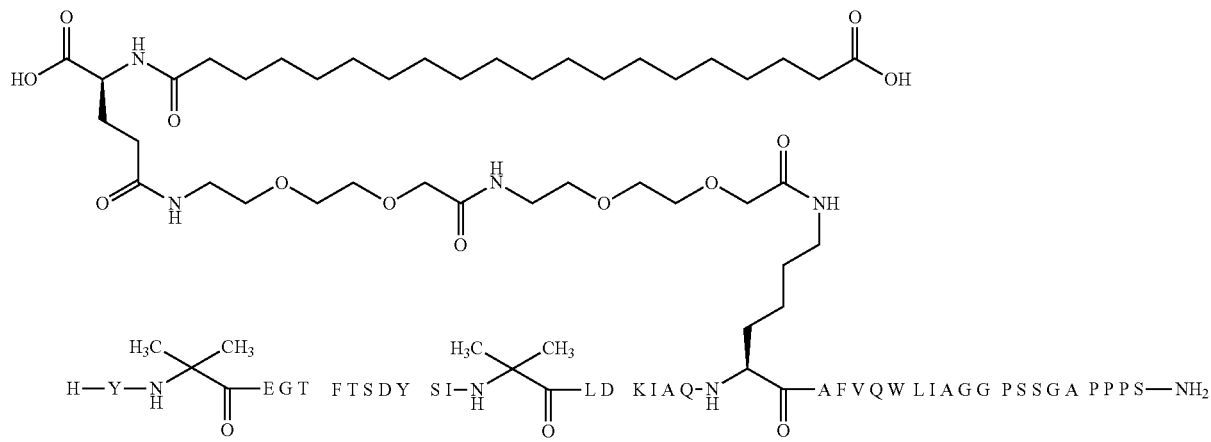

SEQ ID NO.: 4 with C-terminal amide modification; substituent: Chem. 11 attached to Lys20
Synthesis methods: SPPS_A; DS_D; CP_A
Molecular weight (average) calculated: 4813.5 Da
LCMS_A: Rt=6.2 min; found $[M+3H]^{3+}$ 1605.2, $[M+4H]^{4+}$ 1204.3

Compound No. 1
(D-Lys)[(4S)-4-carboxy-4-(15-carboxypentadecanoylamino)butanoyl]-Sar-Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

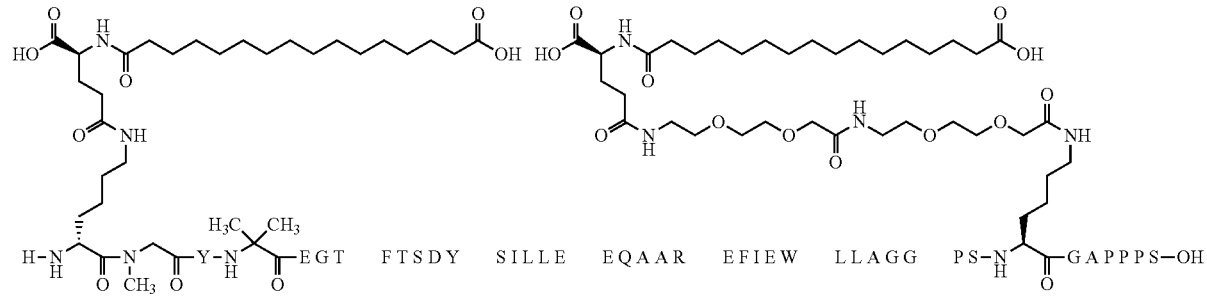

Z: Parent compound no. 1; X=D-Lys; Y=Sar; substituent b: Chem. 16 attached to X; substituent z: Chem. 8 attached to Lys33 of Z.
Synthesis methods: SPPS_A; DS_A; DS_D; CP_A
Molecular weight (average) calculated: 5498.2 Da
LCMS_A: Rt=6.8 min; found [M+3H]$^{3+}$ 1833.4, [M+4H]$^{4+}$ 1375.3

Compound No. 2
G-Aeg[(4S)-4-carboxy-4-(15-carboxypentadecanoylamino)butanoyl]-Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

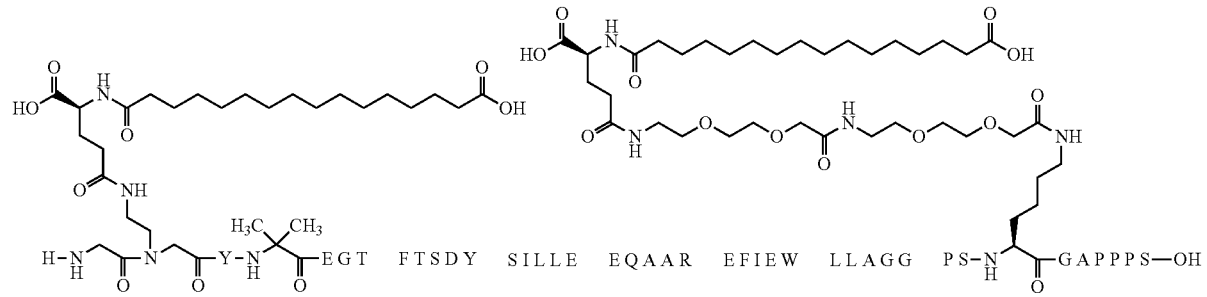

Z: Parent compound no. 1; X=Gly; Y=Aeg; substituent b: Chem. 16 attached to Y; substituent
z: Chem. 8 attached to Lys33 of Z
Synthesis methods: SPPS_B; DS_B; DS_D; CP_A
Molecular weight (average) calculated: 5456.1 Da
LCMS_A: Rt=7.0 min; found [M+3H]$^{3+}$ 1819.4, [M+4H]$^{4+}$ 1364.8

Compound No. 3
K[(4S)-4-carboxy-4-(15-carboxypentadecanoylamino)butanoyl]-Sar-Y-Aib-EGTFTSDYSILLEEQAAREFIEWL-LAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

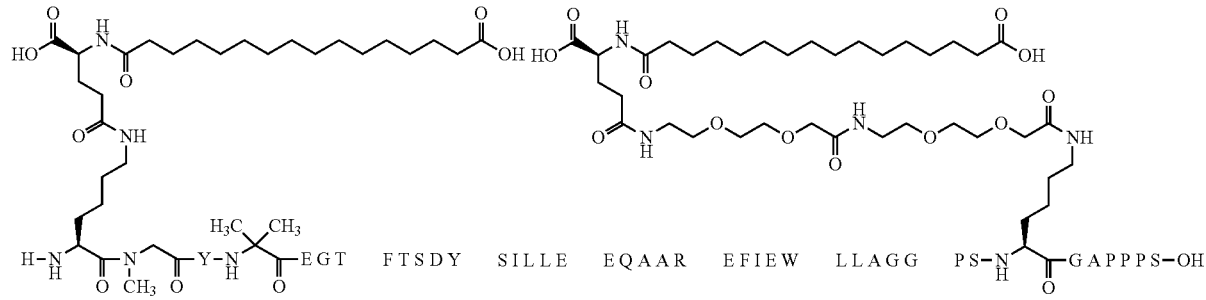

Z: Parent compound no. 1; X=Lys; Y=Sar; substituent b:
Chem. 16 attached to X; substituent
z: Chem. 8 attached to Lys33 of Z
Synthesis methods: SPPS_A; DS_A; DS_D; CP_A
Molecular weight (average) calculated: 5498.2 Da
LCMS_A: Rt=6.9 min; found $[M+3H]^{3+}$ 1833.7, $[M+4H]^{4+}$ 1375.6

Compound No. 4
A-Aeg[(4S)-4-carboxy-4-(15-carboxypentadecanoylamino)butanoyl]-Y-Aib-EGTFTSDYSILLEEQAAREFIEWL-LAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

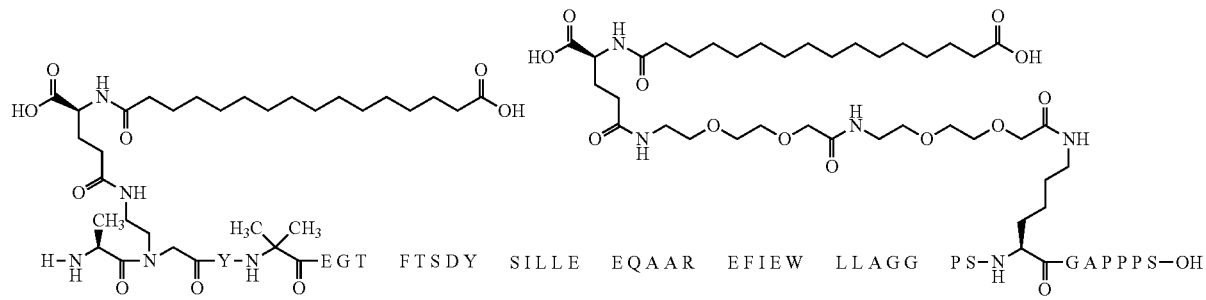

Z: Parent compound no. 1; X=Ala; Y=Aeg; substituent b:
Chem. 16 attached to Y; substituent
z: Chem. 8 attached to Lys33 of Z
Synthesis methods: SPPS_B; DS_B; DS_D; CP_A
Molecular weight (average) calculated: 5470.1 Da
LCMS_A: Rt=7.0 min; found $[M+3H]^{3+}$ 1823.8, $[M+4H]^{4+}$ 1368.2

Compound No. 5
L-Aeg[(4S)-4-carboxy-4-(15-carboxypentadecanoylamino)
butanoyl]-Y-Aib-EGTFTSDYSILLEEQAAREFIEWL-
LAGGPS-K[2-[2-[2-[[2-[2-[2-[[(4S)-4-carboxy-4-(15-car-
boxypentadecanoylamino)butanoyl]amino]ethoxy]ethoxy]
acetyl]amino]ethoxy]ethoxy]acetyl]-GAPPPS-OH

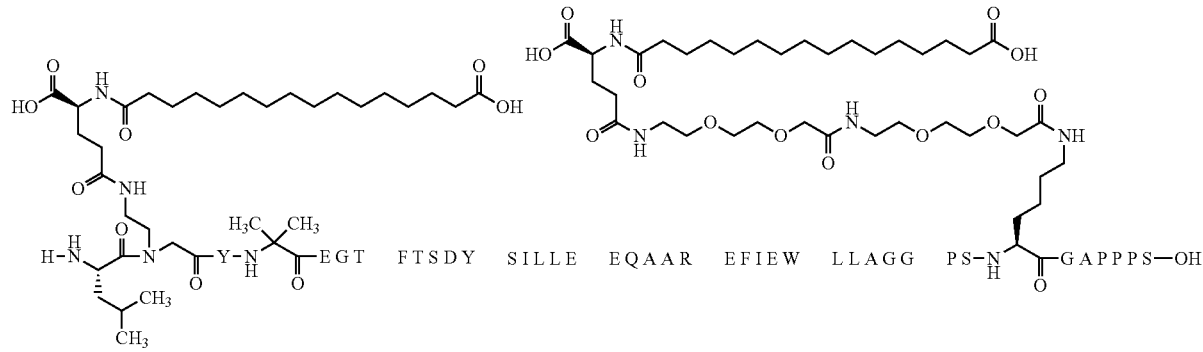

Z: Parent compound no. 1; X=Leu; Y=Aeg; substituent b: Chem. 16 attached to Y; substituent
z: Chem. 8 attached to Lys33 of Z
Synthesis methods: SPPS_B; DS_B; DS_D; CP_A
Molecular weight (average) calculated: 5512.2 Da
LCMS_A: Rt=7.1 min; found [M+3H]$^{3+}$ 1838.1, [M+4H]$^{4+}$ 1378.9

Compound No. 6
P-Aeg[(4S)-4-carboxy-4-(15-carboxypentadecanoylamino)
butanoyl]-Y-Aib-EGTFTSDYSILLEEQAAREFIEWL-
LAGGPS-K[2-[2-[2-[[2-[2-[2-[[(4S)-4-carboxy-4-(15-car-
boxypentadecanoylamino)butanoyl]amino]ethoxy]ethoxy]
acetyl]amino]ethoxy]ethoxy]acetyl]-GAPPPS-OH

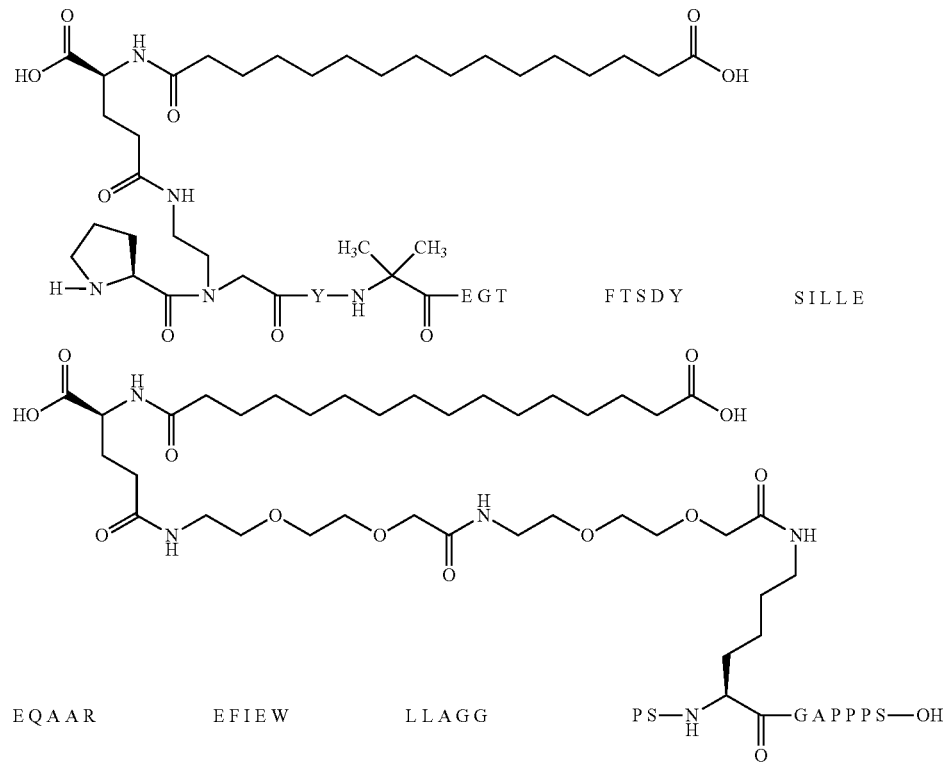

Z: Parent compound no. 1; X=Pro; Y=Aeg; substituent b: Chem. 16 attached to Y; substituent
z: Chem. 8 attached to Lys33 of Z
Synthesis methods: SPPS_B; DS_B; DS_D; CP_A
Molecular weight (average) calculated: 5496.2 Da
LCMS_A: Rt=7.0 min; found [M+3H]$^{3+}$ 1832.4, [M+4H]$^{4+}$ 1374.6

Compound No. 7
D-Aeg[(4S)-4-carboxy-4-(15-carboxypentadecanoylamino)butanoyl]-Y-Aib-EGTFTSDYSILLEEQAAREFIEWL-LAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

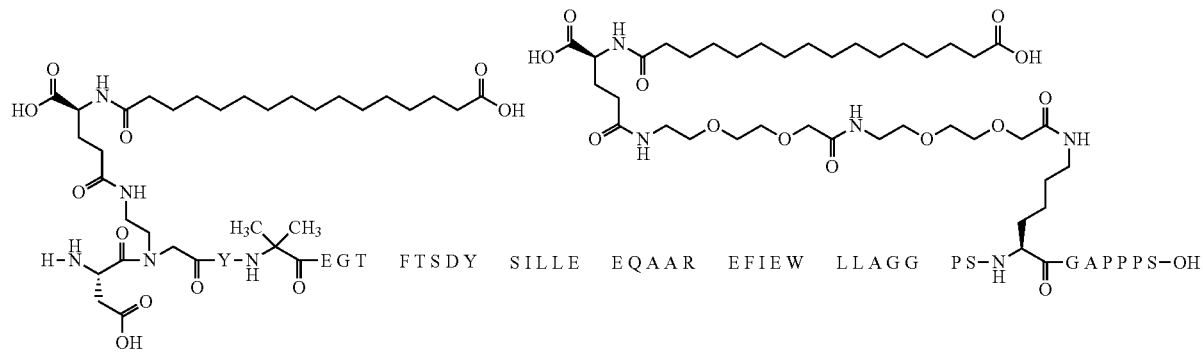

Z: Parent compound no. 1; X=Asp; Y=Aeg; substituent b: Chem. 16 attached to Y; substituent
z: Chem. 8 attached to Lys33 of Z
Synthesis methods: SPPS_A; DS_C; DS_D; CP_A
Molecular weight (average) calculated: 5514.1 Da
LCMS_B: Rt=10.2 min; found $[M+3H]^{3+}$ 1838.8, $[M+4H]^{4+}$ 1379.3.

Compound No. 8
K[(4S)-4-carboxy-4-[[(4S)-4-carboxy-4-(15-carboxypentadecanoylamino)butanoyl]amino]butanoyl]-Sar-Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

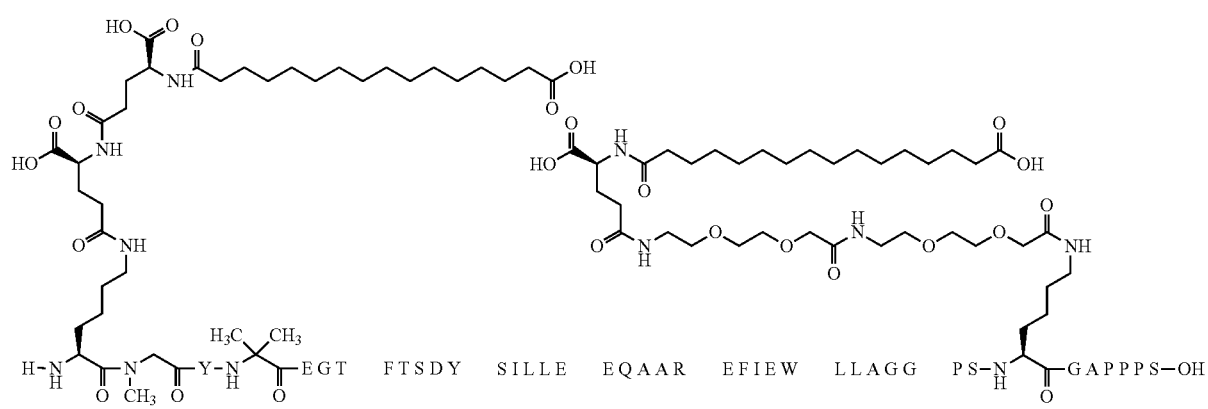

Z: Parent compound no. 1; X=Lys; Y=Sar; substituent b: Chem. 18 attached to X; substituent
z: Chem. 8 attached to Lys33 of Z
Synthesis methods: SPPS_B; DS_A; DS_D; CP_A
Molecular weight (average) calculated: 5627.3 Da
LCMS_A: Rt=6.9 min; found $[M+3H]^{3+}$ 1876.3, $[M+4H]^{4+}$ 1407.6

Compound No. 9
K[2-[[(4S)-4-carboxy-4-(15-carboxypentadecanoylamino)butanoyl]amino]acetyl]-Sar-Y-Aib-EGTFTSDYSILLE-EQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

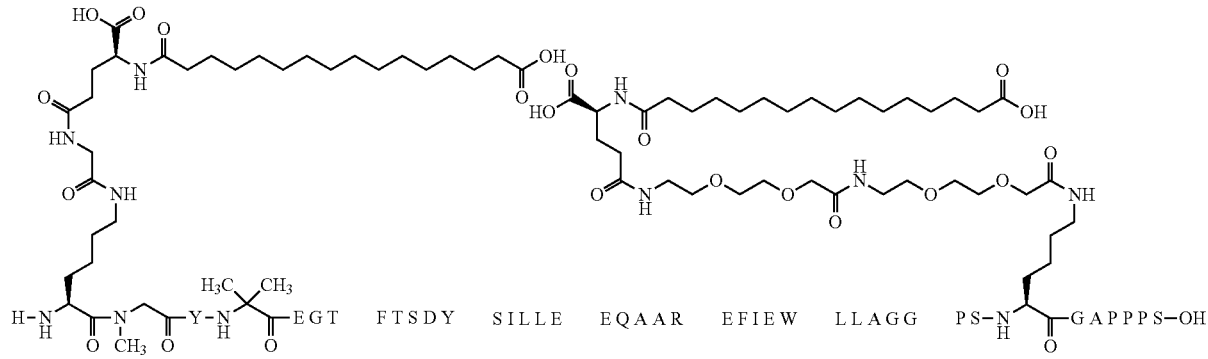

Z: Parent compound no. 1; X=Lys; Y=Sar; substituent b: Chem. 19 attached to X; substituent
z: Chem. 8 attached to Lys33 of Z
Synthesis methods: SPPS_B; DS_A; DS_D; CP_A
Molecular weight (average) calculated: 5555.2 Da
LCMS_A: Rt=6.9 min; found [M+3H]$^{3+}$ 1852.3, [M+4H]$^{4+}$ 1389.7

Compound No. 10
(D-Lys)[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]acetyl]-Sar-Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-GAPPPS-OH

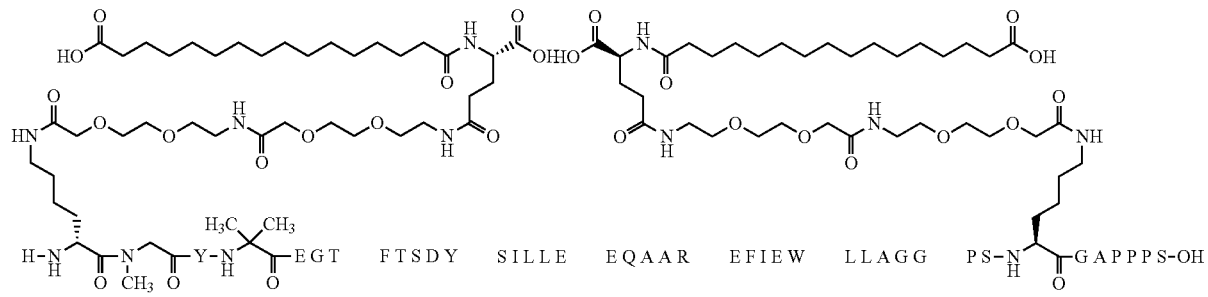

Z: Parent compound no. 1; X=D-Lys; Y=Sar; substituent b: Chem. 21 attached to X;
substituent z: Chem. 8 attached to Lys33 of Z
Synthesis methods: SPPS_B; DS_A; DS_D; CP_A
Molecular weight (average) calculated: 5788.5 Da
LCMS_A: Rt=6.9 min; found [M+3H]3$^{+}$ 1930.3, [M+4H]4$^{+}$ 1447.8

Compound No. 11
(D-Lys)[(2S)-2-amino-6-[[(4S)-4-carboxy-4-(15-carboxy-pentadecanoylamino)butanoyl]amino]hexanoyl]-Sar-Y-Aib-EGTFTSDYSILLEEQAAREFIEWLLAGGPS-K[2-[2-[2-[[2-[2-[2-[[(4S)-4-carboxy-4-(15-carboxypent-adecanoylamino)butanoyl]amino]ethoxy]ethoxy]acetyl]amino]ethoxy]ethoxy]acetyl]-GAPPPS-OH

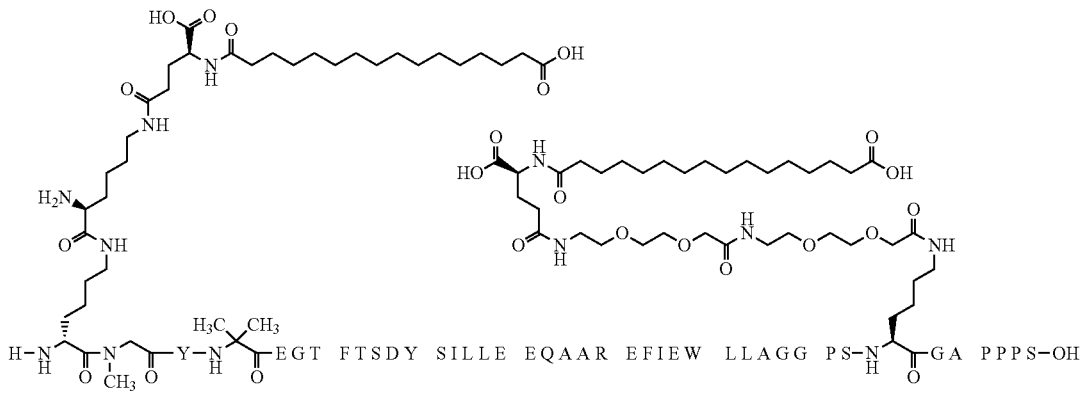

Z: Parent compound no. 1; X=D-Lys; Y=Sar; substituent b: Chem. 20 attached to X;
substituent z: Chem. 8 attached to Lys33 of Z
Synthesis methods: SPPS_B; DS_A; DS_D; CP_A
Molecular weight (average) calculated: 5626.4 Da
LCMS_A: Rt=6.7 min; found [M+3H]$^{3+}$ 1876.2, [M+4H]$^{4+}$ 1407.2

Compound No. 12
K[(4S)-4-carboxy-4-(15-carboxypentadecanoylamino)bu-tanoyl]-Sar-Y-Aib-EGTFTSDYSILLEEQAAREFIEWL-LAGGPS-K[(2S)-2-amino-6-[[(2S)-2-amino-6-[[(4S)-4-carboxy-4-(15-carboxypentadecanoylamino)butanoyl]amino]hexanoyl]amino]hexanoyl]-GAPPPS-OH

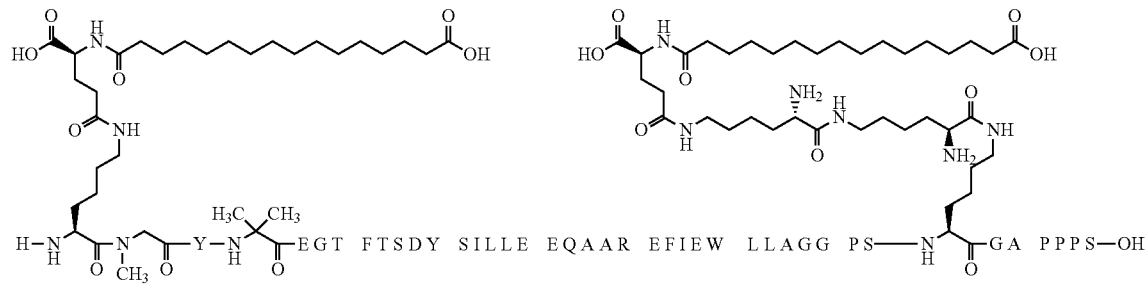

Z: Parent compound no. 2; X=Lys; Y=Sar; substituent b: Chem. 16 attached to X; substituent
z: Chem. 10 attached to Lys33 of Z
Synthesis methods: SPPS_A; DS_A; DS_D; CP_A
Molecular weight (average) calculated: 5464.2 Da
LCMS_A: Rt=6.6 min; found [M+3H]$^{3+}$ 1822.2, [M+4H]$^{4+}$ 1366.7

Compound No. 13
K[(4S)-4-carboxy-4-(17-carboxyheptadecanoylamino)bu-
tanoyl]-Sar-Y-Aib-EGTFTSDYSILLEEQAAREFIEWL-
LAGGPS-K[(2S)-2-amino-6-[[(2S)-2-amino-6-[[(4S)-4-
carboxy-4-(15-carboxypentadecanoylamino)butanoyl]
amino]hexanoyl]amino]hexanoyl]-GAPPPS-OH

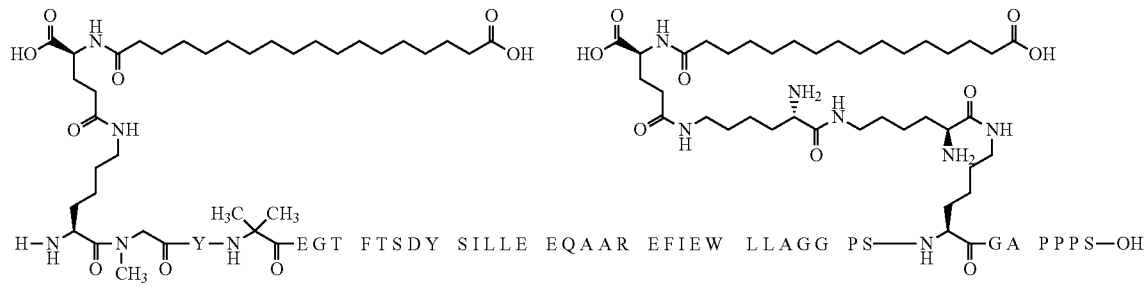

Z: Parent compound no. 2; X=Lys; Y=Sar; substituent b: Chem. 17 attached to X; substituent
z: Chem. 10 attached to Lys33 of Z
Synthesis methods: SPPS_B; DS_A; DS_D; CP_A
Molecular weight (average) calculated: 5492.3 Da
LCMS_A: Rt=6.8 min; found [M+3H]$^{3+}$ 1831.4, [M+4H]$^{4+}$ 1373.7

Compound No. 14
K[(2S)-2,6-bis[[(4S)-4-carboxy-4-(15-carboxypentade-
canoylamino)butanoyl]amino]hexanoyl]-Sar-Y-Aib-
EGTFTSDYSILLEEQAAREFIEWLLAGGPS-K[(2S)-2-
amino-6-[[(2S)-2-amino-6-[[(4S)-4-carboxy-4-(15-
carboxypentadecanoylamino)butanoyl]amino]hexanoyl]
amino]hexanoyl]-GAPPPS-OH

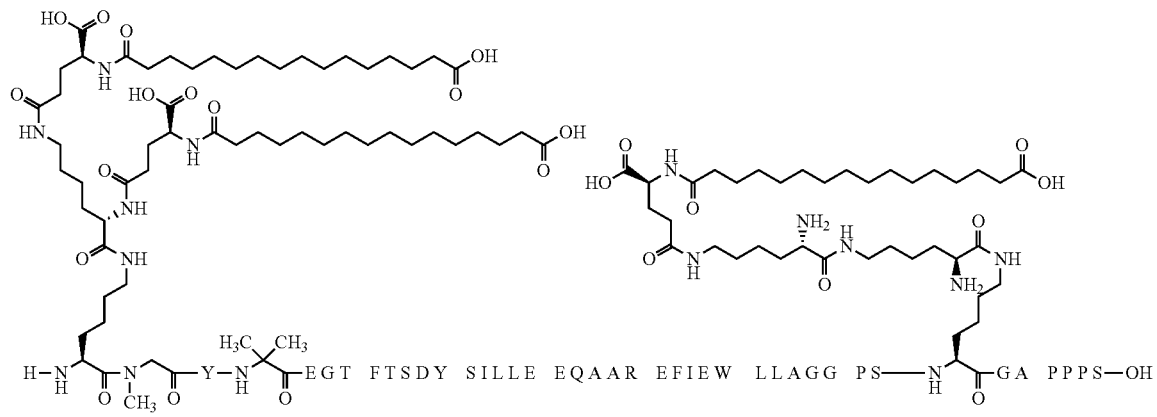

Z: Parent compound no. 2; X=Lys; Y=Sar; substituent b:
Chem. 22 attached to X; substituent
z: Chem. 10 attached to Lys33 of Z
Synthesis methods: SPPS_A; DS_A; DS_D; CP_A
Molecular weight (average) calculated: 5989.9 Da
LCMS_A: Rt=7.0 min; found [M+3H]$^{3+}$ 1997.1, [M+4H]$^{4+}$ 1498.0

Compound No. 15
K[(4S)-4-carboxy-4-(17-carboxyheptadecanoylamino)bu-tanoyl]-Sar-Y-Aib-EGTFTSDYSILLEEQAAREFIEWL-LAGGPS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-GAPPPS-OH

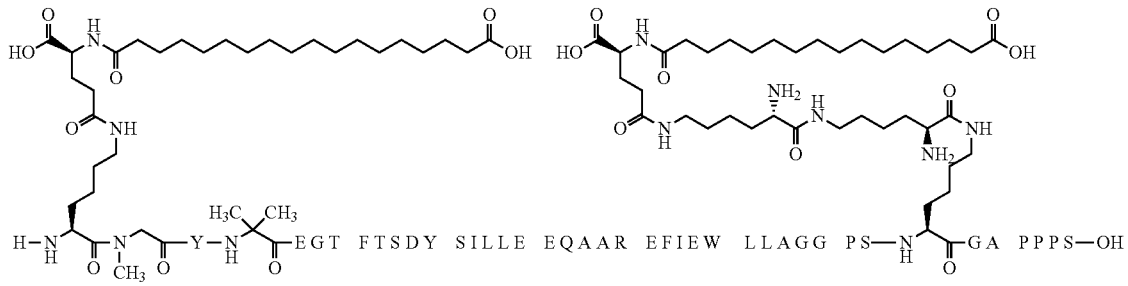

Z: Parent compound no. 3; X=Lys; Y=Sar; substituent b: Chem. 17 attached to X; substituent
z: Chem. 7 attached to Lys33 of Z
Synthesis methods: SPPS_A; DS_A; DS_D; CP_A
Molecular weight (average) calculated: 5520.3 Da
LCMS_A: Rt=7.0 min; found $[M+3H]^{3+}$ 1840.9, $[M+4H]^{4+}$ 1380.9

Compound No. 16
K[(4S)-4-carboxy-4-(15-carboxypentadecanoylamino)bu-tanoyl]-Sar-Y-Aib-EGTFTSDYSILLE-K[(2S)-2-amino-6-[[(2S)-2-amino-6-[[(4S)-4-carboxy-4-(17-carboxyheptade-canoylamino)butanoyl]amino]hexanoyl]amino]hexanoyl]-QAAREFIEWLLAGGPSSGAPPPS-OH Z: Parent compound no. 4; X=Lys; Y=Sar; substituent b: Chem. 16 attached to X; substituent
z: Chem. 7 attached to Lys16 of Z
Synthesis methods: SPPS_A; DS_A; DS_D; CP_A
Molecular weight (average) calculated: 5450.2 Da
LCMS_A: Rt=6.3 min; found $[M+3H]^{3+}$ 1817.3, $[M+4H]^{4+}$ 1363.1

Compound No. 17
G-Aeg[(4S)-4-carboxy-4-(15-carboxypentadecanoylamino)butanoyl]-Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLAGGPSSGAPPPS-OH

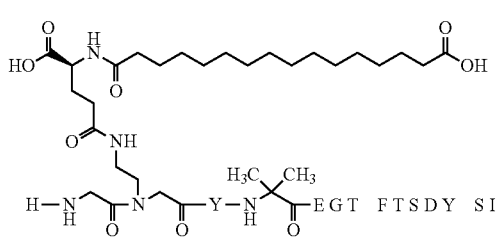
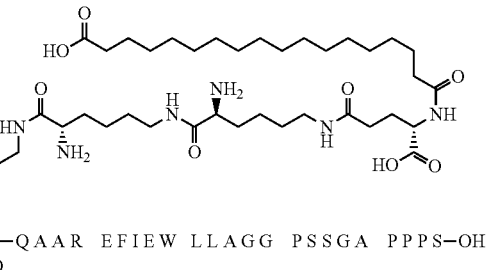

Z: Parent compound no. 4; X=Gly; Y=Aeg; substituent b: Chem. 16 attached to Y; substituent
z: Chem. 7 attached to Lys16 of Z
Synthesis methods: SPPS_A; DS_C; DS_D; CP_A
Molecular weight (average) calculated: 5408.2 Da
LCMS_B: Rt=9.5 min; found [M+3H]$^{3+}$ 1803.6, [M+4H]$^{4+}$ 1353.0

Compound No. 18
K[(4S)-4-carboxy-4-(15-carboxypentadecanoylamino)butanoyl]-Sar-Y-Aib-EGTFTSDYSI-Aib-LDKIAQK[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-AFVQWLIAGGPSSGAPPPS-NH$_2$

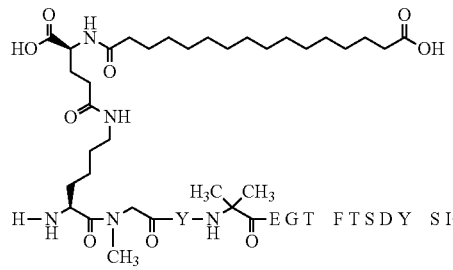
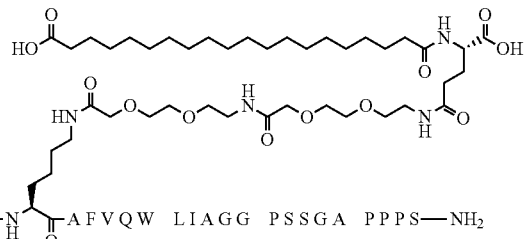

Z: Parent compound no. 5; X=Lys; Y=Sar; substituent b: Chem. 16 attached to X; substituent
z: Chem. 11 attached to Lys20 of Z
Synthesis methods: SPPS_A; DS_A; DS_D; CP_A
Molecular weight (average) calculated: 5410.2 Da
LCMS_A: Rt=6.6 min; found [M+3H]$^{3+}$ 1804.0, [M+4H]$^{4+}$ 1353.5

Non-Converting Compound No. 1
K[(4S)-4-carboxy-4-(15-carboxypentadecanoylamino)bu-
tanoyl]-Val-Y-Aib-EGTFTSDYSILLEEQAAREFIEWL-
LAGGPS-K[2-[2-[2-[[2-[2-[2-[[(4S)-4-carboxy-4-(15-car-
boxypentadecanoylamino)butanoyl]amino]ethoxy]ethoxy]
acetyl]amino]ethoxy]ethoxy]acetyl]-GAPPPS-OH

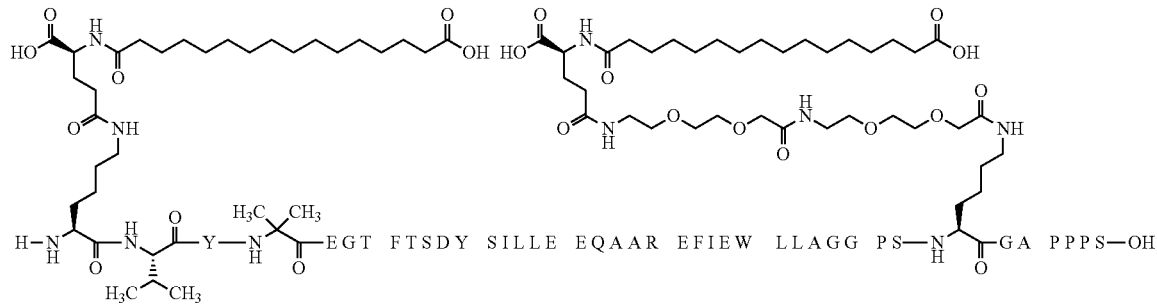

Z: Parent compound no. 1; X=Lys; Y=Val; substituent b:
Chem. 16 attached to X; substituent
z: Chem. 8 attached to Lys33 of Z
Synthesis methods: SPPS_A; DS_A; DS_D; CP_A
Molecular weight (average) calculated: 5526.2 Da
LCMS_A: Rt=6.9 min; found [M+3H]$^{3+}$ 1842.8, [M+4H]$^{4+}$ 1382.2

Non-Converting Compound No. 2
K[(4S)-4-carboxy-4-(15-carboxypentadecanoylamino)bu-
tanoyl]-Val-Y-Aib-EGTFTSDYSILLEEQAAREFIEWL-
LAGGPS-K[(2S)-2-amino-6-[[(2S)-2-amino-6-[[(4S)-4-
carboxy-4-(15-carboxypentadecanoylamino)butanoyl]
amino]hexanoyl]amino]hexanoyl]-GAPPPS-OH

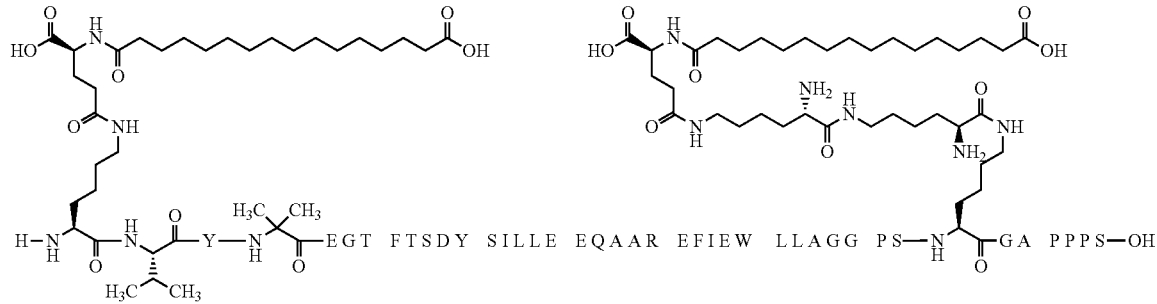

Z: Parent compound no. 2; X=Lys; Y=Val; substituent b:
Chem. 16 attached to X; substituent
z: Chem. 10 attached to Lys33 of Z
Synthesis methods: SPPS_A; DS_A; DS_D; CP_A
Molecular weight (average) calculated: 5492.3 Da
LCMS_A: Rt=6.6 min; found [M+3H]$^{3+}$ 1831.4, [M+4H]$^{4+}$ 1373.9

Non-Converting Compound No. 3
K[(4S)-4-carboxy-4-(15-carboxypentadecanoylamino)butanoyl]-Val-Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLAGGPSSGAPPPS-OH

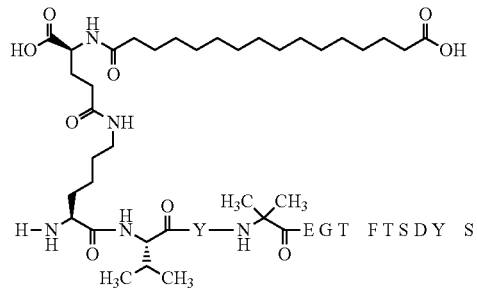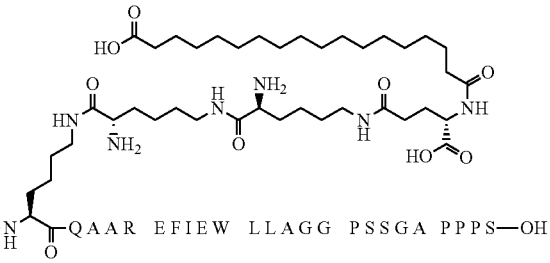

Z: Parent compound no. 4; X=Lys; Y=Val; substituent b: Chem. 16 attached to X; substituent
z: Chem. 7 attached to Lys16 of Z
Synthesis methods: SPPS_A; DS_A; DS_D; CP_A
Molecular weight (average) calculated: 5478.3 Da
LCMS_A: Rt=6.1 min; found $[M+3H]^{3+}$ 1826.7, $[M+4H]^{4+}$ 1370.3

Non-converting compound No. 4
K[(4S)-4-carboxy-4-(15-carboxypentadecanoylamino)butanoyl]-Val-Y-Aib-EGTFTSDYSI-Aib-LDKIAQK[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-AFVQWLIAGGPSSGAPPPS-$NH_2$

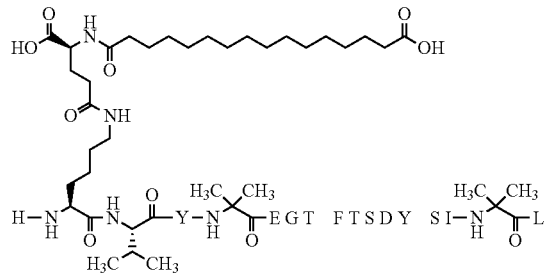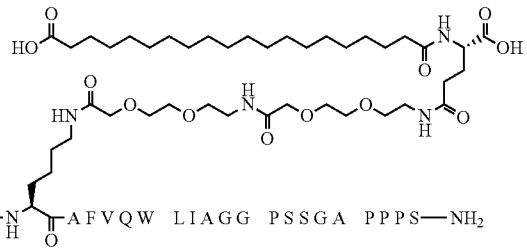

Z: Parent compound no. 5; X=Lys; Y=Val; substituent b: Chem. 16 attached to X; substituent
z: Chem. 11 attached to Lys20 of Z
Synthesis methods: SPPS_A: DS_A: DS_D; CP_A
Molecular weight (average) calculated: 5438.3 Da
LCMS_A: Rt=6.6 min; found $[M+3H]^{3+}$ 1813.4, $[M+4H]^{4+}$ 1360.2

General Methods for Measuring Conversion Half-Life

The assay was performed to investigate the conversion half-life of prodrug to drug of the prodrugs of the invention. The conversion half-life was investigated in vitro at pH 7.4 upon incubation at 37° C.

Preparation of Formulation and Sampling

Test compounds were dissolved to a concentration of 100 μM in phosphate-buffered saline (140 mM NaCl, 2.07 mM KCl, 8.05 mM $Na_2HPO_4$, 1.96 mM $KH_2PO_4$, pH 7.4). Solution pH was measured after dissolution and adjusted to pH 7.4 with aqueous NaOH if necessary. The solution was filtered through a 0.22 μm syringe filter, then incubated in a water bath at 37° C. Aliquots were withdrawn at defined timepoints, e.g. every 24-72 hours, for LCMS analysis.

Analysis and Calculations

LCMS analysis was performed using the procedure defined in LCMS_A above. The AUC of the prodrug, active drug, and DKP were determined using UV detection at 214 nm, and the ratio of prodrug AUC over total AUC of prodrug plus active drug plus DKP was calculated. The negative natural logarithm of this ratio was plotted over time, and a linear regression of this relationship was then performed. The conversion half-life was calculated from this linear regression as the time at which the AUC ratio=0.5.

Example 2

The prodrug to drug conversion half-life of the compounds of the invention was measured as described in General Methods for Measuring Conversion Half-life. The results are presented in Table 6. The compounds of the invention are associated with surprisingly long conversion half-lives, which can be tuned through subtle modifications of the chemical structure of the DKP moiety.

TABLE 6

Prodrug conversion half-life in PBS buffer at pH 7.4 and 37° C.

| Compound No. | Conversion half-life [h] |
| --- | --- |
| 1 | 244 |
| 2 | 363 |
| 3 | 111 |
| 4 | 97 |
| 5 | 74 |
| 6 | 440 |
| 7 | 38 |
| 8 | 125 |
| 9 | 132 |

TABLE 6-continued

Prodrug conversion half-life in PBS buffer at pH 7.4 and 37° C.

| Compound No. | Conversion half-life [h] |
| --- | --- |
| 10 | 195 |
| 11 | 182 |
| 12 | 129 |
| 13 | 137 |
| 14 | 166 |
| 15 | 127 |
| 16 | 117 |
| 18 | 101 |

General Methods for Measuring Terminal Half-Life in Minipigs

The purpose of this method is to determine the half-life in vivo of the derivatives of the present invention after i.v. administration to minipigs, i.e. the prolongation of their time in the body and thereby their time of action. This is done in a pharmacokinetic (PK) study, where the terminal half-life of the derivative in question is determined. By terminal half-life is generally meant the period of time it takes to halve a certain plasma concentration, measured after the initial distribution phase.

Study

Female Göttingen minipigs were obtained from Ellegaard Göttingen Minipigs (Dalmose, Denmark) approximately 7-14 months of age and weighing from approximately 16-35 kg were used in the studies. The minipigs were housed individually and fed restrictedly once daily with SDS minipig diet (Special Diets Services, Essex, UK).

After at 3 weeks of acclimatisation two permanent central venous catheters were implanted in vena cava caudalis in each animal. The animals were allowed 1 week recovery after the surgery, and were then used for repeated pharmacokinetic studies with a suitable wash-out period between successive derivative dosing.

The animals were fasted for approximately 18 hours before dosing and from 0 to 4 hours after dosing but had ad libitum access to water during the whole period.

The sodium salts of compounds of Examples 1 were prepared using method SX_A under General Methods for preparation of the compounds of the invention. The resulting sodium salts were dissolved to a concentration of 50-300 nmol/mL in a buffer containing 0.007% polysorbate 20, 50 mM sodium phosphate, 70 mM sodium chloride, pH 7.4. Intravenous injections (the volume corresponding to usually 1-20 nmol/kg, for example 0.02-0.05 mL/kg) of the compounds were given through one catheter, and blood was sampled at predefined time points for up to 21 days post dosing (preferably through the other catheter). Blood samples (for example 0.8 mL) were collected in 8 mM EDTA buffer and then centrifuged at 4° C. and 1942 g for 10 minutes.

Sampling and Analysis

Plasma was pipetted into Micronic tubes on dry ice and kept at −20° C. until analysed for plasma concentration of the compounds using ELISA, or a similar antibody-based assay, or LCMS. Individual plasma concentration-time profiles were analysed by a non-compartmental model in Phoenix WinNonLin ver. 6.4. (Pharsight Inc., Mountain View, CA, USA), and the resulting terminal half-lives (harmonic mean) determined.

Example 3

The terminal half-lives and/or the observed terminal half-lives, measured as described herein in General Methods for Measuring Terminal Half-Life in Minipigs are shown in Table 7. Parent compound Nos. 1, 2, and 4, administered in their free form, are associated with surprisingly high observed terminal half-lives, which is extended further by addition of a non-converting dipeptide and substituent (eg Non-converting compound No. 1). The use of a converting prodrug (eg. compound Nos. 1, 3, 9, and 10) results in a shorter half-life than the non-converting counterpart (eg Non-converting compound No. 1), since conversion contributes to the elimination of the converting prodrug but not to the non-converting compound, and conversion cannot be differentiated from other mechanisms of elimination. This provides evidence that conversion of prodrug to parent compound is occurring in vivo. The terminal half-life of the prodrug may be faster or slower than the corresponding parent compound due to the contribution of conversion on the terminal half-life of the prodrug.

TABLE 7

Terminal half-life as measured after i.v. administration to minipigs

| Compound No. | Dose of test compound (nmol/kg) | Terminal $t_{1/2}$ (h) |
| --- | --- | --- |
| Parent compound 1 | 2 | 121 |
| Parent compound 2 | 1 | 104 |
| Parent compound 4 | 1 | 106 |
| Non-converting compound 1 | 2 | 170 |
| Compound 1 | 20 | 118 |
| Compound 3 | 2 | 119 |
| Compound 9 | 20 | 102 |
| Compound 10 | 20 | 118 |

General Methods for Measuring Oral Bioavailability in Beagle Dogs

The purpose of this method is to determine the terminal half-life and plasma exposure in vivo of the compounds of the present invention after p.o. administration to beagle dogs, i.e. the terminal half-life and concentration of test substance that reaches circulation with time. This is done in a pharmacokinetic (PK) study, where these parameters of the compound in question are determined. By terminal half-life is generally meant the period of time it takes to halve a certain plasma concentration, measured after the initial distribution phase.

Preparation of Tablet Compositions

Tablet compositions comprising the test compounds obtained from Example 1 and SNAC (sodium N-(8-(2-hydroxybenzoyl)amino)caprylate) were prepared according to methods known to the person skilled in the art by mixing test substance with roller compacted SNAC and magnesium stearate as e.g. described in WO 2019/149880. Each tablet was comprised of 7.7 mg magnesium stearate, 2-4 mg of each compound tested, and 300 mg SNAC.

Animals, Dosing, and Sampling

Male beagle dogs, 1-7 years of age and weighing 9-17 kg during the study period, were included in the study. The dogs were dosed in a fasting state. The dogs were group housed in pens (12 hours light: 12 hours dark), and fed individually and restrictedly once daily with Royal Canin Medium Adult dog food (Royal Canin Products, China Branch, or Brogaarden A/S, Denmark). The dogs were used for repeated PK studies with a suitable wash-out period between successive dosing. An appropriate acclimatisation period was given prior to initiation of the first PK study. All handling, dosing, and blood sampling of the animals were performed by trained and skilled staff. Before the studies, the dogs were fasted overnight and from 0 to 4 hours after dosing. The dogs were restricted to water 1 hour before dosing until 4 hours after dosing, but otherwise had adlibitum access to water during the whole period.

The compositions were administered by a single oral dosing to the dogs in groups of 6-8 dogs. The tablets were administered in the following manner: 10 min prior to tablet administration, the dogs may be dosed subcutaneously with approximately 3 nmol/kg of SEQ ID NO.: 7 (HSQGTFTSDYSKYLDSRRAQDFVQWLMNT), then tablets were placed in the back of the mouth of the dog to prevent chewing. The mouth was then closed, and 10 mL of tap water was given by syringe or gavage to facilitate swallowing of the tablet.

One blood sample was drawn before dosing, and additional samples were drawn at predefined time points after dosing, such as for up to 600 hours, to adequately cover the full plasma concentration-time absorption profile of the test substance. For each blood sample time point, approximately 0.8 mL of whole blood was collected in a 1.5 mL EDTA-coated tube, which was gently turned to mix the sample with EDTA. Blood samples were collected in EDTA buffer (8 mM) and then centrifuged at 4° C. and 2000 g for 10 minutes. Plasma was pipetted into Micronic tubes on dry ice, and kept at −20° C. or lower until analysis. Blood samples were taken as appropriate, for example from a venflon in the cephalic vein in the front leg for the first 2 hours and then with syringe from the jugular vein for the rest of the time points. The first few drops were allowed to drain from the venflon to avoid heparin saline from the venflon in the sample. All blood samples were collected into test tubes containing EDTA for stabilisation and kept on ice until centrifugation. Plasma was separated from whole blood by centrifugation and the plasma was stored at −20° C. or lower until analysis.

Analysis and Calculations

The plasma was analysed for test substance using LC-MS (Liquid Chromatography-Mass Spectrometry) as known to the person skilled in the art. The system consisted of either: a Thermo Fisher QExactive mass spectrometer equipped with a 10-valve interface module TurboFlow system, CTC HTS PAL autosampler, Accela 1250 pumps, and Hot Pocket column oven; or a Thermo Fisher QExactive Plus mass spectrometer equipped with a valve interface module TurboFlow system, TriPlus RSI autosampler, Dionex UltiMate 3000 pumps, and Hot Pocket column oven. Reversed-phase HPLC separation was achieved using a linear gradient of 1:1 acetonitrile/methanol in 1% aqueous formic acid using either: a Phenomenex Onyx Monolithic C18 column (50× 2.0 mm) and a flow rate of 0.8 mL/min at 30° C.; or an Agilent Poroshell 120 SB-C18 column (50×2.1 mm, 2.7 µm) at a flow rate of 0.4 mL/min at 60° C. The mass spectrometer was operated in either positive ionization SIM mode or positive ionization PRM mode.

For each individual animal, a plasma concentration-time profile was analysed by a non-compartmental model in Pharsight Phoenix WinNonLin ver. 6.4 software or other relevant software for PK analysis, and the resulting terminal half-life ($t_{1/2}$), maximum plasma concentration per dose ($C_{max}/D$), time for maximum plasma concentration ($t_{max}$), and area under the curve to infinity per dose (AUC/D) were determined. Summary statistics of pharmacokinetic results were presented as median (for $t_{max}$), harmonic mean ($t_{1/2}$), or arithmetic mean ($C_{max}$, AUC).

Example 4

The pharmacokinetic properties, measured as described herein in General Methods for Measuring Oral Bioavailability in Beagle Dogs, are shown in Table 8. All tested compounds of the present invention demonstrate oral bioavailability in this model, as concentrations of the compounds in plasma were detected ($C_{max}/D>0$ and AUC/D>0) following oral administration. All tested compounds are also associated with surprisingly high observed terminal half-lives as observed in Example 3.

TABLE 8

Pharmacokinetic parameters as measured after p.o. administration to Beagle dogs

| Compound No. | Dose of test compound (mg/tablet) | $T_{max}$ (h) | Terminal $t_{1/2}$ (h) | $C_{max}/$ Dose (kg/L) | AUC/ Dose (kg*h/L) |
|---|---|---|---|---|---|
| Parent compound 1 | 3 | 1.5 | 104 | 0.67 | 60.7 |
| Parent compound 3 | 2.9 | 1.5 | 131 | 0.22 | 21.4 |
| Parent compound 4 | 2.9* | 1.3* | 56* | 0.35* | 17.9* |
| Parent compound 5 | 3 | 1.0 | 134 | 0.22 | 13.0 |
| Non-converting compound 1 | 2.8 | 1.5 | 137 | 0.21 | 20.1 |
| Non-converting compound 2 | 3.5 | 1.3 | 130 | 0.13 | 10.8 |
| Non-converting compound 3 | 3.0 | 4.0 | 115 | 0.27 | 31.4 |
| Non-converting compound 4 ( | 3.0 | 7.0 | 136 | 0.16 | 18.9 |
| Compound 1 | 3.1 | 4.0 | 146 | 0.66 | 41.2 |
| Compound 2 | 2.9 | 4.0 | 142 | 0.18 | 22.9 |
| Compound 3 | 3.0 | 7.0 | 139 | 0.32 | 38.5 |
| Compound 5 | 2.8 | 7.0 | 106 | 0.25 | 23.4 |
| Compound 12 | 2.7 | 1.3 | 143 | 0.46 | 50.8 |
| Compound 13 | 2.8 | 4.3 | 121 | 0.36 | 41.3 |
| Compound 14 | 3.2 | 5.5 | 119 | 0.38 | 43.6 |
| Compound 15 | 2.0 | 1.5 | 124 | 0.20 | 21.7 |
| Compound 16 | 2.9 | 4.0 | 96 | 0.73 | 67.6 |
| Compound 17 | 3.2 | 1.5 | 105 | 0.30 | 30.4 |
| Compound 18 | 2.9 | 4.0 | 88 | 0.15 | 13.3 |

* = averaged data from three experiments

General Methods for Measuring In Vitro Functional Potency

The purpose of this example is to test the functional activity, or potency, of the compounds in vitro at the human GLP-1 and GIP receptors. The in vitro functional potency is the measure of target receptor activation in a whole cell assay. The potencies of parent compound Nos. 1-5 of Example 1 were determined as described below. Human GLP-1(7-37) (HAEGT FTSDV SSYLE GQAAK EFIAW LVKGR G; SEQ ID NO.: 8) and human GIP (YAEGT FISDY SIAMD KIHQQ DFVNW LLAQK GKKND WKHNI TQ; SEQ ID NO.: 9) were included as reference compounds in appropriate assays for comparison.

Principle

In vitro functional potency was determined by measuring the response of the target receptor in a reporter gene assay in individual cell lines. The assay was performed in stably transfected BHK cell lines that expresses one of the following G-protein coupled receptors: human GLP-1 receptor or human GIP receptor; and where each cell line contains the DNA for the cAMP response element (CRE) coupled to a promoter and the gene for firefly luciferase (CRE luciferase). When the respective receptor is activated, it results in the production of cAMP, which in turn results in expression of the luciferase protein. When assay incubation is completed, luciferase substrate (luciferin) is added resulting in the enzymatic conversion of luciferin to oxyluciferin and producing bioluminescence. The luminescence is measured as the readout for the assay.

Cell Culture and Preparation

The cells lines used in these assays were BHK cells with BHKTS13 as a parent cell line. The cell lines were derived from a clone containing the CRE luciferase element and were established by further transfection with the respective human receptor to obtain the relevant cell line: BHK CRE luc2P hGLP-1R or BHK CRE luc2P hGIPR. The cells were cultured at 37° C. with 5% $CO_2$ in Cell Culture Medium. They were aliquoted and stored in liquid nitrogen. The cells were kept in continuous culture and were seeded out the day before each assay.

Materials

The following chemicals were used in the assay: Pluronic F-68 10% (Gibco 2404), human serum albumin (HSA; Sigma A9511), 10% fetal bovine serum (FBS; Invitrogen 16140-071), chicken egg white ovalbumin (Sigma A5503), DMEM w/o phenol red (Gibco 21063-029), DMEM (Gibco 12430-054), 1 M Hepes (Gibco 15630), Glutamax 100× (Gibco 35050), G418 (Invitrogen 10131-027), hygromycin (Invitrogen 10687-010), and steadylite plus (PerkinElmer 6016757).

Buffers

GLP-1R Cell Culture Medium consisted of DMEM medium with 10% FBS, 500 µg/mL G418, and 300 µg/mL hygromycin. GIPR Cell Culture Medium consisted of DMEM medium with 10% FBS, 400 µg/mL G418, and 300 µg/mL hygromycin. Assay Buffer consisted of DMEM w/o phenol red, 10 mM Hepes, 1× Glutamax, 1% ovalbumin, and 0.1% Pluronic F-68 with the addition of HSA at twice the final assay concentration. The Assay Buffer was mixed 1:1 with an equal volume of the test compound in Assay Buffer to give the final assay concentration of HSA.

Procedure

1) Cells were plated at 5000 cells/well and incubated overnight in the assay plate.
2) Cells were washed once in DPBS.
3) Stocks of the test compounds and reference compounds in concentrations ranging from 100-300 µM were diluted 1:150 in Assay Buffer. Compounds were then diluted 1:10 in column 1 of a 96 deep well dilution plate and then carried across the row creating a 3.5 fold, 12 point dilution curve.
4) Assay Buffer (50 µl aliquot) with or without HSA was added to each well in the assay plate.
5) A 50 µl aliquot of compound or blank was transferred from the dilution plate to the assay plate containing the Assay Buffer with or without HSA.
6) The assay plate was incubated for 3 h in a 5% $CO_2$ incubator at 37° C.
7) The cells were washed once with DPBS.
8) A 100 µl aliquot of DPBS was added to each well of the assay plate.
9) A 100 µl aliquot of steadylite plus reagent (light sensitive) was added to each well of the assay plate.
10) Each assay plate was covered with aluminum foil to protect it from light and shaken at 250 rpm for 30 min at room temperature.
11) Each assay plate was read in a microtiter plate reader.

Calculations and Results

The data from the microtiter plate reader was first regressed in an Excel in order to calculate the x-axis, log scale concentrations based on the individual test compound's stock concentration and the dilutions of the assay. This data was then transferred to GraphPad Prism software for graphing and statistical analysis. The software performs a non-linear regression (log(agonist) vs response). $EC_{50}$ values which were calculated by the software and reported in pM are shown in Table 9 below. A minimum of two replicates was measured for each sample. The reported values are averages of the replicates. The compounds of the present invention display potent functional activation of the human GLP-1R and human GIPR receptors under the given conditions.

Example 5

The GLP-1 and GIP receptor functional potencies, measured as described herein in General methods for measuring in vitro functional potency, are shown in Table 9. Parent compounds 1-5, administered in their free form, display potent functional activation of the human GLP-1 receptor and human GIP receptor under the given conditions.

TABLE 9

Functional potencies at human GLP-1R and GIPR in the presence of 0% and 1% HSA.

| Compound No. | hGLP-1R, CRE Luc 0% HSA $EC_{50}$ (pM) | hGLP-1R, CRE Luc 1% HSA $EC_{50}$ (pM) | hGIPR, CRE Luc 0% HSA $EC_{50}$ (pM) | hGIPR, CRE Luc 1% HSA $EC_{50}$ (pM) |
|---|---|---|---|---|
| hGLP-1(7-37) | 8.4 | 6.7 | nd | nd |
| hGIP | nd | nd | 11.3 | 6.4 |
| Parent compound 1 | 2.1 | 154.5 | 3.1 | 155.7 |
| Parent compound 2 | 1.5 | 110.8 | 1.8 | 97.0 |
| Parent compound 3 | 4.0 | 359.5 | 5.6 | 444.5 |
| Parent compound 4 | 4.2 | 202.0 | 4.7 | 188.5 |
| Parent compound 5 | 9.7 | 530.9 | 4.2 | 136.8 | nd = not determined.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A compound of
(compund no. 3; SEQ ID NO: 5)
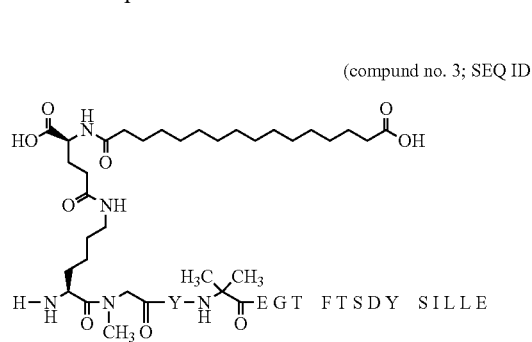
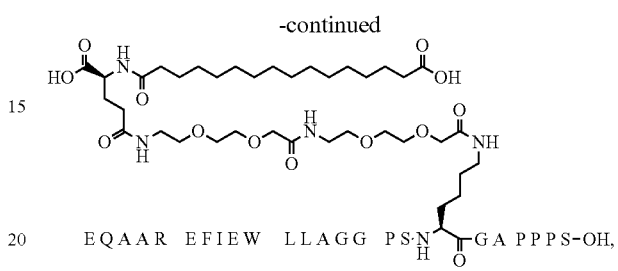
EQAAR EFIEW LLAGG PS-N(H)-GA PPPS-OH,
or a pharmaceutical acceptable salt, ester or amide thereof.
\* \* \* \* \*

SEQUENCE LISTING

```
Sequence total quantity: 9
SEQ ID NO: 1          moltype = AA  length = 39
FEATURE               Location/Qualifiers
REGION                1..39
                      note = Synthetic
source                1..39
                      mol_type = protein
                      organism = synthetic construct
```

| | |
|---|---|
| VAR_SEQ | 15<br>note = Xaa - Xaa15 is D or E |
| VAR_SEQ | 21<br>note = Xaa - Xaa21 is A or E |
| VAR_SEQ | 31<br>note = Xaa - Xaa31 is P or absent |
| VAR_SEQ | 33<br>note = Xaa - Xaa33 is S, K or absent |
| VAR_SEQ | 24<br>note = Xaa - Xaa24 is E, Q or N |
| VAR_SEQ | 36<br>note = Xaa - Xaa36 is P or absent |
| VAR_SEQ | 6<br>note = Xaa - Xaa6 is F or V |
| VAR_SEQ | 2<br>note = Xaa - Xaa2 is Aib or A |
| VAR_SEQ | 19<br>note = Xaa - Xaa19 is A or Q |
| VAR_SEQ | 32<br>note = Xaa - Xaa32 is E, S or absent |
| VAR_SEQ | 17<br>note = Xaa - Xaa17 is Q or I |
| VAR_SEQ | 20<br>note = Xaa - Xaa20 is Q, R, E, H or K |
| VAR_SEQ | 13<br>note = Xaa - Xaa13 is Y, A, L or Aib |
| VAR_SEQ | 23<br>note = Xaa - Xaa23 is I or V |
| VAR_SEQ | 35<br>note = Xaa - Xaa35 is A or absent |
| VAR_SEQ | 37<br>note = Xaa - Xaa37 is P or absent |
| VAR_SEQ | 39<br>note = Xaa - Xaa39 is S or absent |
| VAR_SEQ | 27<br>note = Xaa - Xaa27 is L or I |
| VAR_SEQ | 34<br>note = Xaa - Xaa34 is G or absent |
| VAR_SEQ | 12<br>note = Xaa - Xaa12 is I or Y |
| VAR_SEQ | 28<br>note = Xaa - Xaa28 is A or R |
| VAR_SEQ | 16<br>note = Xaa - Xaa16 is K or E |
| VAR_SEQ | 30<br>note = Xaa - Xaa30 is G or absent |
| VAR_SEQ | 38<br>note = Xaa - Xaa38 is P or absent |

SEQUENCE: 1
YXEGTXTSDY SXXLXXXAXX XFXXWLXXGX XXXXXXXXX 39

| | |
|---|---|
| SEQ ID NO: 2 | moltype = AA length = 39 |
| FEATURE | Location/Qualifiers |
| REGION | 1..39<br>note = Synthetic |
| source | 1..39<br>mol_type = protein<br>organism = synthetic construct |
| VAR_SEQ | 16<br>note = Xaa - Xaa16 is K or E |
| VAR_SEQ | 15<br>note = Xaa - Xaa15 is D or E |
| MOD_RES | 2<br>note = Xaa - Xaa2 is Aib |
| VAR_SEQ | 23<br>note = Xaa - Xaa23 is I or V |
| VAR_SEQ | 20<br>note = Xaa - Xaa20 is R or K |
| VAR_SEQ | 17<br>note = Xaa - Xaa17 is Q or I |
| VAR_SEQ | 19<br>note = Xaa - Xaa19 is A or Q |
| VAR_SEQ | 27<br>note = Xaa - Xaa27 is L or I |
| VAR_SEQ | 13<br>note = Xaa - Xaa13 is L or Aib |
| VAR_SEQ | 21<br>note = Xaa - Xaa21 is A or E |

```
VAR_SEQ                 24
                        note = Xaa - Xaa24 is E or Q
VAR_SEQ                 33
                        note = Xaa - Xaa33 is S or K
SEQUENCE: 2
YXEGTFTSDY SIXLXXXAXX XFXXWLXAGG PSXGAPPPS                         39

SEQ ID NO: 3            moltype = AA  length = 39
FEATURE                 Location/Qualifiers
REGION                  1..39
                        note = Synthetic
source                  1..39
                        mol_type = protein
                        organism = synthetic construct
MOD_RES                 2
                        note = Xaa - Xaa2 is Aib
VAR_SEQ                 33
                        note = Xaa - Xaa33 is S or K
VAR_SEQ                 16
                        note = Xaa - Xaa16 is K or E
SEQUENCE: 3
YXEGTFTSDY SILLEXQAAR EFIEWLLAGG PSXGAPPPS                         39

SEQ ID NO: 4            moltype = AA  length = 39
FEATURE                 Location/Qualifiers
REGION                  1..39
                        note = Synthetic
source                  1..39
                        mol_type = protein
                        organism = synthetic construct
MOD_RES                 2
                        note = Xaa - Xaa2 is Aib
MOD_RES                 13
                        note = Xaa - Xaa13 is Aib
SEQUENCE: 4
YXEGTFTSDY SIXLDKIAQK AFVQWLIAGG PSSGAPPPS                         39

SEQ ID NO: 5            moltype = AA  length = 39
FEATURE                 Location/Qualifiers
REGION                  1..39
                        note = Synthetic
source                  1..39
                        mol_type = protein
                        organism = synthetic construct
MOD_RES                 2
                        note = Xaa - Xaa is Aib
SEQUENCE: 5
YXEGTFTSDY SILLEEQAAR EFIEWLLAGG PSKGAPPPS                         39

SEQ ID NO: 6            moltype = AA  length = 39
FEATURE                 Location/Qualifiers
REGION                  1..39
                        note = Synthetic
source                  1..39
                        mol_type = protein
                        organism = synthetic construct
MOD_RES                 2
                        note = Xaa - Xaa2 is Aib
SEQUENCE: 6
YXEGTFTSDY SILLEKQAAR EFIEWLLAGG PSSGAPPPS                         39

SEQ ID NO: 7            moltype = AA  length = 29
FEATURE                 Location/Qualifiers
source                  1..29
                        mol_type = protein
                        organism = Homo sapiens
SEQUENCE: 7
HSQGTFTSDY SKYLDSRRAQ DFVQWLMNT                                    29

SEQ ID NO: 8            moltype = AA  length = 31
FEATURE                 Location/Qualifiers
source                  1..31
                        mol_type = protein
                        organism = Homo sapiens
SEQUENCE: 8
HAEGTFTSDV SSYLEGQAAK EFIAWLVKGR G                                 31
```

```
SEQ ID NO: 9          moltype = AA  length = 42
FEATURE               Location/Qualifiers
source                1..42
                      mol_type = protein
                      organism = Homo sapiens
SEQUENCE: 9
YAEGTFISDY SIAMDKIHQQ DFVNWLLAQK GKKNDWKHNI TQ                              42
```